US012252542B2

United States Patent
Zhang et al.

(10) Patent No.: US 12,252,542 B2
(45) Date of Patent: Mar. 18, 2025

(54) ANTI-CD137 ANTIBODIES AND METHOD OF TREATING COLORECTAL CANCER USING THEM

(71) Applicant: SHIHUIDA PHARMACEUTICAL GROUP (JILIN) CO., LTD., Baishan (CN)

(72) Inventors: Xin Zhang, Suzhou (CN); Jianjian Peng, Suzhou (CN); Kai Fu, Suzhou (CN); Hui Ma, Suzhou (CN); Xiaolong Pan, Suzhou (CN); Shilong Fu, Suzhou (CN); Shuli Ma, Suzhou (CN); Jian Ding, Suzhou (CN)

(73) Assignee: Shihuida Pharmaceutical Group (Jilin) Co., Ltd., Baishan (CN)

( * ) Notice: Subject to any disclaimer, the term of this patent is extended or adjusted under 35 U.S.C. 154(b) by 1008 days.

(21) Appl. No.: 17/285,760

(22) PCT Filed: Sep. 12, 2019

(86) PCT No.: PCT/CN2019/105537
§ 371 (c)(1),
(2) Date: Apr. 15, 2021

(87) PCT Pub. No.: WO2020/078149
PCT Pub. Date: Apr. 23, 2020

(65) Prior Publication Data
US 2021/0380708 A1    Dec. 9, 2021

(30) Foreign Application Priority Data
Oct. 19, 2018    (WO) ................. PCT/CN2018/111086

(51) Int. Cl.
*C07K 16/28*    (2006.01)
*A61K 39/00*    (2006.01)
*A61P 35/00*    (2006.01)

(52) U.S. Cl.
CPC .......... *C07K 16/2878* (2013.01); *A61P 35/00* (2018.01); *A61K 2039/505* (2013.01); *C07K 2317/31* (2013.01); *C07K 2317/56* (2013.01); *C07K 2317/74* (2013.01)

(58) Field of Classification Search
CPC .................................................. C07K 16/2878
See application file for complete search history.

(56) References Cited

U.S. PATENT DOCUMENTS

| 10,174,122 B2 | 1/2019 | Kwon et al. |
| 2018/0258177 A1 | 9/2018 | Kwon et al. |
| 2018/0282422 A1 | 10/2018 | Xu et al. |
| 2019/0071510 A1 | 3/2019 | Kwon et al. |

FOREIGN PATENT DOCUMENTS

| CN | 1566341 A | 1/2005 |
| EP | 3 354 661 A1 | 8/2018 |
| JP | 2018-527939 A | 9/2018 |
| WO | WO 2017/049452 A1 | 3/2017 |
| WO | WO 2018/011421 A1 | 1/2018 |
| WO | WO 2018/127787 A1 | 7/2018 |

OTHER PUBLICATIONS

Yonezawa et al., Boosting cancer immunotherapy with anti-CD137. Clin. Cancer Res., 21, 3113-3120, 2015. (Year: 2015).*
International Search Report issued Dec. 18, 2019 in PCT/CN2019/105537 (submitting English translation only), 4 pages.
Beifen Shen, "Antibodies for Tumor Therapy and their Modification Strategy" Chinese Journal of Cancer Biotherapy, vol. 14, No. 2, Apr. 30, 2007, pp. 101-104 (with English Abstract).
Jaafar N. Haidar, et al., "A Universal Combinatorial Design of Antibody Framework to Graft Distinct CDR Sequences: A Bioinformatics Approach" Proteins, vol. 80, Nov. 11, 2011, pp. 896-912.
Extended European Search Report issued Aug. 8, 2022 in European Patent Application No. 19873484.0, 8 pages.
Japanese Office Action issued May 9, 2023 in Japanese Patent Application No. 2021-521057, 3 pages.

* cited by examiner

*Primary Examiner* — Elly-Gerald Stoica
(74) *Attorney, Agent, or Firm* — Merchant & Gould P.C.; Daniel J. Pereira

(57) ABSTRACT

An antibody may be capable of specifically binding CD137 or an antigen binding fragment thereof, wherein the light chain variable region and the heavy chain variable region have one or more mutations. The antibody or antigen binding fragment thereof may be used in preparing a drug. The antibody or an antigen binding fragment thereof may specifically bind CD137, and may include a light chain variable region VL and a heavy chain variable region VH, wherein compared to a sequence as shown in SEQ ID NO: 103, the VL comprises one or more VL amino acid mutations, and the VL amino acid mutation occurs at one or more positions: V3, A10, K44, D71, and/or V77.

20 Claims, 11 Drawing Sheets

Specification includes a Sequence Listing.

ANTI-CD137 ANTIBODIES AND METHOD OF TREATING COLORECTAL CANCER USING THEM

CROSS-REFERENCE TO RELATED APPLICATIONS

The present application is the national stage claiming priority under 35 U.S.C. § 371 to international application PCT/CN2019/105537, filed Sep. 12, 2019, which claims the benefit of international application PCT/CN2018/111086, filed Oct. 19, 2018. Priority is claimed to each of these applications, the disclosure of each of which, to the extent allowed, is incorporated by reference herein in its entirety.

FIELD OF THE INVENTION

The present application relates to the field of biomedicine, and particularly to an antibody or an antigen binding fragment thereof capable of specifically binding CD137 protein.

BACKGROUND OF THE INVENTION

CD137 protein (also known as 4-1BB, TNFRSF9, etc.) is a member of the tumor necrosis factor receptor superfamily, belonging to type I transmembrane protein. CD137L is a member of the tumor necrosis factor receptor superfamily, belonging to type II transmembrane protein. The results of the current studies indicate that, CD137L is mainly expressed on activated APC, for example dendritic cells (DC), macrophages and B cells (Pollok, K E et al., 1994, Eur. J. Immunol. 24: 367-374); while T cells may induce the expression of CD137 after receiving antigen-specific signals (Kwon, B. S. et al., 1989, PNAS 86: 1963-67). The function of CD137 on T cells has been confirmed sufficiently. In the presence of a certain amount of CD3 antibody, the activation of CD137 signals may induce the proliferation of T cells and the synthesis of cytokines (mainly IFN-γ), and inhibit the apoptosis of activated T cells, thus extending the life of T cells.

However, the currently developed anti-CD137 antibodies have low stability and limited inhibition on tumors, thereby it is urgent to develop a new anti-CD137 drug for new drug development.

SUMMARY OF THE INVENTION

The present application provides an antibody specifically binding CD137 or an antigen binding fragment thereof and a use thereof. The anti-CD137 antibody of the present application has one or more of the following properties: 1) capable of specifically binding CD137 protein; 2) having the activity of CD137 agonists; 3) having a higher stability; 4) having a higher purity; 5) capable of being used for treating cancer.

In one aspect, the present application comprises an antibody specifically binding CD137 or an antigen binding fragment thereof, comprising a light chain variable region VL and a heavy chain variable region VH, in which compared to a sequence as set forth in SEQ ID NO: 103, the VL comprises one or more VL amino acid mutations occurring at one or more positions selected from a group consisting of: V3, A10, K44, D71 and V77.

In some embodiments, compared to a sequence as set forth in SEQ ID NO: 127, the VH comprises one or more VH amino acid mutations, the VH amino acid mutation occurs at one or more positions selected from a group consisting of: Q13, N78, H84, D86, A90 and F97.

In some embodiments, the VL amino acid mutation comprises VL amino acid mutations occurring at positions A10 and V77.

In some embodiments, the VH amino acid mutation comprises a VH amino acid mutation occurring at position Q13.

In some embodiments, the VH amino acid mutations further comprises a VH amino acid mutation occurring at position N78.

In some embodiments, the VL amino acid mutation comprises VL amino acid mutations at positions of any one of the following groups: 1) V3, D71 and V77; 2) A10 and V77; 3) D71; 4) A10, D71 and V77; 5) D71 and V77; 6) A10 and D71; or 7) V3, A10, K44, D71 and V77.

In some embodiments, the VH amino acid mutation comprises VH amino acid mutations at positions of any one of the following groups: 1) N78; 2) N78, H84, and D86; 3) Q13, N78, H84 and D86; 4) Q13 and N78; 5) Q13, H84, D86, A90 and F97; or 6) Q13, N78, H84, D86, A90 and F97.

In some embodiments, the VL amino acid mutation and the VH amino acid mutation comprise amino acid mutations at positions of any one of the following groups, respectively: 1) VL: V3, D71 and V77, and VH: N78; 2) VL: D71, and VH: N78, H84 and D86; 3) VL: D71 and V77, and VH: N78, H84 and D86; 4) VL: A10, D71 and V77, and VH: N78, H84 and D86; 5) VL: A10 and D71, and VH: Q13, N78, H84 and D86; 6) VL: V3, A10, K44, D71 and V77, and VH: Q13 and N78; 7) VL: A10 and V77, and VH: Q13, H84, D86, A90 and F97; or 8) VL: A10 and V77, and VH: Q13, N78, H84, D86, A90 and F97.

In some embodiments, the VL amino acid mutation at V3 is selected from: V3A, V3M, V3G. In some embodiments, the VL amino acid mutation at A10 is selected from: A10V, A10L, A10I. In some embodiments, the VL amino acid mutation at K44 is selected from: K44T, K44G. In some embodiments, the VL amino acid mutation at D71 is selected from: D71N, D71Q. In some embodiments, the VL amino acid mutation at V77 is selected from: V77I. In some embodiments, the VH amino acid mutation at Q13 is selected from: Q13K, Q13R. In some embodiments, the VH amino acid mutation at N78 is selected from: N78K, N78D, N78Q. In some embodiments, the VH amino acid mutation at H84 is selected from: H84Q, H84E. In some embodiments, the VH amino acid mutation at D86 is selected from: D86N, D86E. In some embodiments, the VH amino acid mutation at A90 is selected from: A90T, A90S. In some embodiments, the VH amino acid mutation at F97 is selected from: F97Y, F97W.

In some embodiments, the VL amino acid mutation comprises VL amino acid mutations of any one of the following groups: 1) V3A, D71N and V77I; 2) A10V and V77I; 3) D71N; 4) A10V, D71N and V77I; 5) D71N and V77I; 6) A10V and D71N; or 7) V3A, A10V, K44T, D71N and V77I.

In some embodiments, the VH amino acid mutation comprises VH amino acid mutations of any one group below: 1) N78K; 2) N78K, H84Q and D86N; 3) Q13K, N78K, H84Q and D86N; 4) Q13K and N78K; 5) Q13K, H84Q, D86N, A90T and F97Y; or 6) Q13K, N78K, H84Q, D86N, A90T and F97Y.

In some embodiments, the VL amino acid mutation and the VH amino acid mutation comprise amino acid mutations of any one of the following groups, respectively: 1) VL: V3A, D71N and V77I, and VH: N78K; 2) VL: D71N, and VH: N78K, H84Q and D86N; 3) VL: D71N and V77I, and VH: N78K, H84Q and D86N; 4) VL: A10V, D71N and V77I, and VH: N78K, H84Q and D86N; 5) VL: A10V and D71N, and VH: Q13K, N78K, H84Q and D86N; 6) VL: V3A, A10V, K44T, D71N and V77I, and VH: Q13K and N78K; 7) VL: A10V and V77I, and VH: Q13K, H84Q, D86N, A90T and F97Y; or 8) VL: A10V and V77I, and VH: Q13K, N78K, H84Q, D86N, A90T and F97Y.

In some embodiments, the VL comprises an amino acid sequence as set forth in any one of SEQ ID NOs: 104, 106, 108 and 110-114.

In some embodiments, the VH comprises an amino acid sequence as set forth in any one of SEQ ID NOs: 128, 130, 132 and 134-138.

In some embodiments, 1) the VL comprises an amino acid sequence as set forth in SEQ ID NO: 104, and the VH comprises an amino acid sequence as set forth in SEQ ID NO: 128; 2) the VL comprises an amino acid sequence as set forth in SEQ ID NO: 106, and the VH comprises an amino acid sequence as set forth in SEQ ID NO: 130; 3) the VL comprises an amino acid sequence as set forth in SEQ ID NO: 108, and the VH comprises an amino acid sequence as set forth in SEQ ID NO: 132; 4) the VL comprises an amino acid sequence as set forth in SEQ ID NO: 110, and the VH comprises an amino acid sequence as set forth in SEQ ID NO: 134; 5) the VL comprises an amino acid sequence as set forth in SEQ ID NO: 111, and the VH comprises an amino acid sequence as set forth in SEQ ID NO: 135; 6) the VL comprises an amino acid sequence as set forth in SEQ ID NO: 112, and the VH comprises an amino acid sequence as set forth in SEQ ID NO: 136; 7) the VL comprises an amino acid sequence as set forth in SEQ ID NO: 113, and the VH comprises an amino acid sequence as set forth in SEQ ID NO: 137; 8) the VL comprises an amino acid sequence as set forth in SEQ ID NO: 114, and the VH comprises an amino acid sequence as set forth in SEQ ID NO: 138.

In some embodiments, the antigen binding fragment is selected from: Fab, Fab', F(ab)$_2$, F(ab')$_2$, Fv and scFv.

In some embodiments, the antibody or the antigen binding fragment thereof further comprises a Fc domain. In some embodiments, the Fc domain comprises an amino acid sequence of a constant region of an immunoglobulin selected from: IgG1, IgG2, IgG3 and IgG4. In some embodiments, the Fc domain is located at a C-terminal of the antibody or the antigen binding fragment thereof. In some embodiments, the Fc domain comprises an amino acid sequence as set forth in SEQ ID NO: 163 or SEQ ID NO: 164.

In some embodiments, the antibody or the antigen binding fragment thereof is a homodimer protein consisting of two polypeptide chains, in which each of the polypeptide chain comprises the light chain variable region VL, the heavy chain variable region VH and the Fc domain, and the Fc domain is located at a C-terminal of the VL.

In some embodiments, the polypeptide chains comprises an amino acid sequence as set forth in any one of SEQ ID NOs: 152, 154, 156 and 158-162.

In another aspect, the present application further provides a multispecific antibody or an antigen binding fragment thereof, comprising a first binding domain specifically binding CD137 and a second binding domain specifically binding a second target other than CD137, in which the first binding domain is the antibody or the antigen binding fragment thereof. In some embodiments, the second target is selected from a tumor associated antigen.

In another aspect, the present application further provides an immunoconjugate, which comprises the antibody or the antigen binding fragment.

In another aspect, the present application further provides an isolated nucleic acid molecule, which encodes the antibody or the antigen binding fragment thereof, or the immunoconjugate.

In another aspect, the present application further provides a vector, which comprises the nucleic acid molecule.

In another aspect, the present application further provides a cell, which comprises the vector.

In another aspect, the present application further provides a pharmaceutical composition, which comprises the antibody or the antigen binding fragment thereof, the immunoconjugate, the nucleic acid molecule, the vector and/or the cell, and optionally, a pharmaceutically acceptable adjuvant.

In another aspect, the present application further provides a use of the antibody or the antigen binding fragment thereof in preparing a drug, and the drug is used for treating cancer. In some embodiments, the cancer is selected from a group consisting of: melanoma, prostatic cancer, colorectal cancer, Merkel cell skin cancer, pancreatic cancer, Non-Hodgkin's lymphoma, squamous cell carcinoma, and breast cancer.

Other aspects and advantages are easily conceived by those skilled in the art from the following detailed description. The following detailed description only shows and describes exemplary embodiments of the present disclosure. As will be recognized by those skilled in the art, the disclosure enables those skilled in the art to make changes to the disclosed specific embodiments without departing from the spirit and scope of the application to which the present application is related. Correspondingly, the attached drawings of the present application and the description of the specification are only exemplary, but not restrictive.

BRIEF DESCRIPTION OF THE DRAWINGS

The specific features related to the present application are shown in the accompanying claims. The characteristics and advantages related to the present application will be better understood with reference to the exemplary embodiments and the attached drawings described in detail below. The attached drawings are illustrated briefly as below:

DETAILED DESCRIPTION OF THE INVENTION

Figure 1:
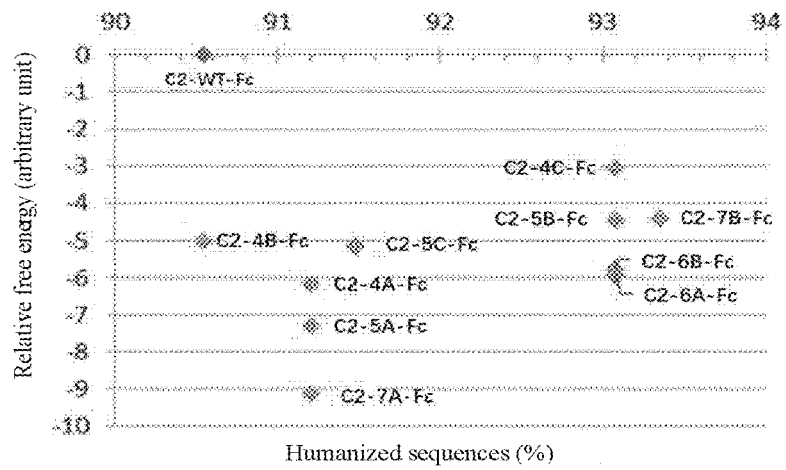
FIG. 1 shows the free energy and homology sequencing results of the mutated anti-CD137 molecule of the present application.

The implementation of the present application will be illustrated in the following specific embodiments, and other advantages and effects of the present application will be easily known by persons familiar with the technology from the disclosures in the specification. The antibody or the antigen binding fragment thereof provided in the present application is capable of specifically binding CD137 protein, and can have the activity of CD137 agonists. In specific embodiments, the antibody or the antigen binding fragment thereof provided in the present application may have a higher stability and a higher purity, which can be used for preparing a pharmaceutical composition and can be used for treating cancers.

The present application will be further described below: In the present application, unless otherwise indicated, scientific and technological terms used in the present application have a meaning as commonly understood by those skilled in the art. In addition, all the protein and nucleic acid chemistry, molecular biology, cell and tissue culture, microbiology, immunology-related terms and laboratory procedures as used in the present application are the terms and conventional steps widely used in corresponding fields. At the same time, in order to better understand the present application, the following definitions and interpretations of related terms are provided below.

In the present application, the term "antibody" generally means a polypeptide molecule capable of specifically recognizing and/or neutralizing a particular antigen. For example, the antibody may comprise an immunoglobulin composed of at least two heavy (H) chains and two light (L) chains linked through a disulfide bond, and comprises any molecules comprising an antigen binding portion thereof. The term "antibody" comprises monoclonal antibodies, antibody fragments or antibody derivatives, comprising but not limited to human antibodies, humanized antibodies, chimeric antibodies, single domain antibodies (e.g., dAb), single chain antibodies (e.g., scFv), and antibody fragments that bind to an antigen (e.g., Fab, Fab' and (Fab)2 fragments). The term "antibody" further comprises all the recombinant forms of the antibody, for example antibodies expressed in prokaryotic cells as well as any antibody fragments that bind to an antigen and derivatives thereof as described herein. Each of the heavy chains may be composed of a heavy chain variable region (VH) and a heavy chain constant region. Each of the light chains may be composed of a light chain variable region (VL) and a light chain constant region. The VH and VL regions may be further distinguished as hypervariable regions known as complementary determining regions (CDR), which are distributed in more conservative regions known as framework regions (FR). Each VH and VL may be composed of three CDRs and four FRs, which are arranged in an order as below from the amino-terminal to the carboxyl-terminal: FR1, CDR1, FR2, CDR2, FR3, CDR3 and FR4. The variable regions of heavy chain and light chain comprise binding domains interacting with antigens. The constant region of the antibody may mediate the binding of the immunoglobulin to the host tissue or factor, and the host tissue or factor comprises various cells (e.g., effector cells) of the immune system and the first component (Clq) of the classical complement system.

In the present application, the term "variable" generally means such a fact that some parts in the sequence of the variable domain of an antibody change strongly, which forms the binding and specificity of various specific antibodies to their specific antigens. However, variability is not uniformly distributed in the whole variable region of the antibody. It focuses in three segments of the light chain and heavy chain variable regions, which is known as a complementary determining region (CDR) or hypervariable region (HVR). More highly conserved parts in the variable domain are known as a framework region (FR). The respective variable domain of a native heavy chain and a light chain comprises four FR regions, most of which have a β-folded configuration connected through three CDRs to form a loop connection, and in some cases form a part of the β-folded configuration. The CDRs in each chain close together through FR regions, and form the antigen binding site of the antibody with the CDR from another chain. In this field, CDR of an antibody may be defined by various methods, for example, 1) Kabat definition rule based on sequence variability (Wu and Kabat, J Exp Med 132:211-50, 1970; Kabat et al., Sequences of Proteins of Immunological Interest, 5th Edition, Public Health Service, National Institutes of Health, Bethesda, Md., 1991), 2) Chothia definition rule based on the location of structural loop areas (Al-Lazikani et al., J Mol Biol 273:927-48, 1997), 3) AbM definition rule for weighing the above two rules using AbM antibody model software of Oxford Molecular, 4) Contact definition rule based on the crystal structure analysis of the resulting complex.

These CDR-labeling methods may be summarized in the following table 1.

TABLE 1

Summarization of different methods for defining CDRs of an antibody in this field

| | CCG Definition | Rabat Definition | AbM Definition | Chothia Definition | Contact Definition |
|---|---|---|---|---|---|
| Light chain CDR1 | L24-L34 | L24-L34 | L24-L34 | L24-L34 | L30-L36 |
| Light chain CDR2 | L50-L56 | L50-L56 | L50-L56 | L50-L56 | L45-L55 |
| Light chain CDR3 | L89-L97 | L89-L97 | L89-L97 | L89-L97 | L89-L96 |
| Heavy chain CDR1 | H26-H35 | H31-H35 | H26-H35 | H26-H32 | H30-H35 |
| Heavy chain CDR2 | H50-H65 | H50-H65 | H50-H58 | H52-H56 | H47-H58 |
| Heavy chain CDR3 | H95-H102 | H95-H102 | H95-H102 | H95-H102 | H93-H101 |

Wherein, Laa-Lbb may refer to an amino acid sequence at positions aa to bb starting from the N-terminal of a light chain of an antibody; Haa-Hbb may refer to an amino acid sequence at positions aa to bb starting from the N-terminal of a heavy chain of an antibody. For example, L24-L34 may refer to the amino acid sequences at positions 24 to 34 starting from the N-terminal of a light chain of an antibody; H26-H35 may refer to the amino acid sequences at positions 26 to 35 starting from the N-terminal of a heavy chain of an antibody. In the present application, amino acid residues in the sequence of the variable domain and the sequence of the full-length antibody are determined using Kabat definition rule.

In the present application, the term "antibody binding fragment" generally means one or more fragments in an antibody that play the function of specifically binding antigens. The antigen-binding function of an antibody may be realized by a full-length fragment of the antibody. The antigen-binding function of an antibody may also be realized by the following fragments: (1) a Fab fragment, i.e., monovalent fragments composed of VL, VH, CL and CH domains; (2) a F(ab')$_2$ fragment, comprising a divalent fragment composed of two Fab fragments linked through a disulfide bond at the hinge region; (3) a Fd fragment composed of VH and CH domains; (4) a Fv fragment composed of single-armed VL and VH domains of an antibody; (5) a dAb fragment composed of VH domains (Ward et al., (1989) Nature 341: 544-546); (6) an isolated complementary determining region (CDR) and (7) a combination of two or more isolated CDRs that may be connected optionally by linkers. In addition, monovalent single-chain molecule Fv (scFv) formed by the matching of VL and VH may be further comprised (see Bird et al. (1988) Science 242: 423-426; and Huston et al. (1988) Proc. Natl. Acad. Sci. 85: 5879-5883). The "antigen binding portion" may further comprises an immunoglobulin fusion protein, the fusion protein comprises a binding domain selected from: (1) a binding domain polypeptide that is fused to an immunoglobulin hinge region polypeptide; (2) an immunoglobulin heavy chain CH2 constant region that is fused to the hinge region; and (3) an immunoglobulin heavy chain CH3 constant region that is fused to the CH2 constant region. For the antibody specifically binding CD137 of the present application, the antibody or the antigen binding fragment thereof is selected from a group consisting of: Fab, scFv, Fab', F(ab)$_2$, F(ab')$_2$ and dAb.

In the present application, the term "CD137 protein", also known as 4-1BB or TNFRS9, generally means a transmembrane protein of the tumor necrosis factor receptor superfamily (TNFRS), which is an activation induced costimulatory molecule and an important regulator of immune response. Studies have demonstrated that the CD137 agonistic monoclonal antibody increases the expression of the costimulatory molecule in many models, and significantly improves the response of cytolytic T lymphocytes, thus playing an anti-tumor effect. The anti-tumor effect of CD137-targeted therapy may be verified through the study on the anti-tumor efficacy of the agonistic anti-mouse CD137 monoclonal antibody in mice. CD137 has become a potent activator of immune cells, and an important candidate antigen for treating various diseases (see Vinay, Dass S., and Byoung S. Kwon. "4-1BB (CD137), an inducible costimulatory receptor, as a specific target for cancer therapy." BMB reports 47.3 (2014): 122.).

In the present application, the term "antibody Fc domain" generally means a Y-shaped base region in the structure of an antibody, also known as a fragment crystallizable region (Fc region). In antibody isotypes of IgG, IgA and IgD, Fc region is composed of two identical protein fragments, which come from the second and the third constant domains of two heavy chains of the antibody; Fc regions of IgM and IgE comprise three heavy chain constant domains in each polypeptide chain. The Fc region of IgG has highly conserved N-glycosylation sites. In the present application, the Fc domain may comprise the Fc domain of IgG4, the sequence of which is as set forth in SEQ ID: 164. In the present application, the Fc domain may further comprises the Fc domain of IgG4 with an S228P mutation in its hinge region, the sequence of which is as set forth in SEQ ID: 163. The S228P mutation may prevent Fab fragments from arm exchange (see Silva, John-Paul et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469). In the present application, the position of S228 in the Fc domain is numbered according to EU Index or EU numbering scheme (Please see Kabat et al., 1991, Sequences of Proteins of Immunological Interest, 5$^{th}$ Edition, United States Public Health Service, National Institutes of Health). EU Index, or the EU Index or EU numbering scheme as in Kabat means the numbering of EU antibodies (Please see Edelman et al., 1969, Proc Natl Acad Sci USA 63:78-85).

In the present application, the term "tumor-associated antigens" (TAAs) means an antigen which is highly expressed during the developing progress of tumorigenesis and is capable of inducing the body's immune responses, they may also be expressed in normal tissues at a small amount. Studies have demonstrated that TAAs occur in various tumors, e.g., lung cancer, liver cancer, breast cancer, prostatic cancer, ovarian cancer, renal cancer, head and neck cancer, esophagus cancer, lymphoma, leukemia, etc. TAA immunogenicity derives from mutated amino acid sequences, abnormal spliceosomes of the protein, reexpression, abnormal apoptosis or necrosis products of embryo protein after adulthood, abnormal distribution of intracellular proteins (e.g., secretion of nucleoprotein), expression of intron sequence, protein phosphorylation and glycosylation and other posttranslational modifications. These abnormal changes of protein may induce the body to produce immune responses, and thereby corresponding autoantibodies may be generated (see Biotechnol, C. M. (2014). Application of detection of tumor-associated antigens and antibodies thereof in the diagnosis of malignant tumors, 8(5), 376-379).

In the present application, the term "immunoconjugate" generally means a fused polypeptide molecule, which may comprise one effector module, at least one antigen binding module and a Fc domain. For example, the immunoconjugate comprises one effector module, two antigen binding modules and a Fc domain. The specific immunoconjugate according to the present application is basically composed of one effector module, two antigen binding modules and Fc domains which are connected through one or more linker sequences. The antigen binding modules and the effector module may be connected to the Fc domains through various interactions and in various constructions. In some embodiments, the two antigen binding module and the Fc domains are connected with each other in the following constructions, so as to form total immunoglobulin molecules.

In the present application, the term "nucleic acid molecule" generally means isolated nucleotides, deoxyribonucleotides or ribonucleotides or analogues thereof in any length isolated from natural environment or synthesized artificially. The nucleic acid molecules of the present application may be isolated. For example, they may be produced or synthesized by the following processes: (i) amplification in vitro, e.g., being produced by amplification through polymerase chain reaction (PCR), (ii) being produced by cloning recombination, (iii) purification, e.g., fractional separation through enzyme digestion and gel electrophoresis, or (iv) synthesis, e.g., through chemical synthesis. In some embodiments, the isolated nucleic acid is a nucleic acid molecule prepared by a recombinant DNA technology. In the present application, a nucleic acid encoding the antibody or the antigen binding fragment thereof may be prepared by various methods well known in this field, comprising but not limited to the overlap extension PCR operated using restrictive fragments or using synthetic oligonucleotides, the specific operations of which may be seen in Sambrook et al., Molecular Cloning, A Laboratory Manual, Cold Spring Harbor Laboratory Press, Cold Spring Harbor, N.Y., 1989; and Ausube et al. Current Protocols in Molecular Biology, Greene Publishing and Wiley-Interscience, New York N.Y., 1993.

In the present application, the term "vector" generally means a nucleic acid molecule capable of self-replicating in appropriate hosts, which transfers the inserted nucleic acid molecules into and/or between host cells. The vector may comprise a vector mainly used for inserting DNA or RNA into cells, a vector mainly used for replicating DNA or RNA, and a vector mainly used for expressing the transcription and/or translation of DNA or RNA. The vector further comprises a vector with various functions mentioned above. The vector may be a polynucleotide which may be transcribed and translated into a polypeptide when introduced into an appropriate host cell. Generally, desired expression products may be produced from the vector by cultivating an appropriate host cell comprising the vector. In the present application, the vector may comprise one or more of the nucleic acid molecules. In addition, the vector may further comprise other genes, e.g., a marker gene allowing to select the vector in appropriate host cells and under suitable conditions. In addition, the vector may further comprise an expression control element allowing the coding region to be properly expressed in an appropriate host. Such control elements are well known to those skilled in the art, for example comprising promoters, ribosome binding sites, enhancers and other control elements for regulating gene transcription or mRNA translation. In some embodiments, the expression control sequences are regulatable elements. The specific structures of the expression control sequences may vary depending on the species or the cell-type functions, but they generally comprises 5'non-transcriptional sequences and 5' and 3' non-translational sequences respectively participating in the initiation of transcription and translation, such as TATA cassettes, capped sequences, CAAT sequences, etc. For example, 5' non-transcriptional expression control sequences may comprise promoter regions, which may comprise promoter sequences for transcribing and controlling functionally-linked nucleic acids. In the present application, the vector may be a pTM vector.

In the present application, the term "cell" generally means those that may or have comprised the immunoconjugate of the present application, those that may or have comprised a plasmid or vector comprising the nucleic acid molecule of the present application, or an individual cell, a cell line or a cell culture capable of expressing the antibody or the antigen binding fragment thereof of the present application. The cell may be a prokaryotic cell (e.g., Escherichia coil), and also may be a eukaryotic cell (e.g., yeast cell, COS cell, Chinese hamster ovary (CHO) cell, HeLa cell, HEK293 cell, COS-1 cell, NSO cell or myeloma cell). In some embodiments, the cell is a mammalian cell.

In the present application, the term "pharmaceutically acceptable adjuvant" means a pharmaceutically acceptable preparation vector, solution or additive for strengthening the properties of the preparation. Such additive is well known to those skilled in the art.

In the present application, the term "cancer" generally means or describes physiological conditions of mammals, the typical characteristics of which are cell proliferation or survival disorder. In the present application, hyperproliferative disease is known as cancer comprises but not limited to a solid tumor, such as cancer occurring at breast, respiratory tract, brain, reproductive organs, digestive tract, urethra, eyes, liver, skin, head and neck, thyroid, and parathyroid, as well as distant metastases thereof. Such disease further comprises lymphoma, sarcoma and leukemia. Examples of breast cancer comprises but not limited to infiltrating ductal carcinoma, infiltrating lobular carcinoma, breast ductal carcinoma in situ and breast lobular carcinoma in situ. Examples of respiratory cancer comprises but not limited to small cell lung cancer and non-small cell lung cancer, and bronchial adenoma and pleuropulmonary blastoma. Examples of brain cancer comprises but not limited to brain stem and hypothalamic gliomas, cerebellar and cerebral astrocytoma, medulloblastoma, ependymoma, and neuroectodermal and pineal tumors. Tumor of male genital organs comprises but not limited to prostate cancer and testicular cancer. Tumor of female genital organs comprises but not limited to endometrial carcinoma, cervical cancer, ovarian cancer, vaginal cancer and vulvar cancer, and hysteroma. Gastrointestinal cancer comprises but not limited to anal carcinoma, colon cancer, colorectal cancer, esophagus cancer, gallbladder carcinoma, gastric cancer, pancreatic cancer, rectal cancer, small intestine cancer and salivary gland cancer. Uninary tract tumor comprises but not limited to bladder cancer, penile cancer, kidney cancer, renal pelvic cancer, ureteral carcinoma and urinary tract cancer. Eye cancer comprises but not limited to intraocular melanoma and retinoblastoma. Examples of liver cancer comprises but not limited to hepatocellular carcinoma (hepatoma with or without fibrolamellar variations), bile duct carcinoma (intrahepatic bile duct carcinoma) and mixed hepatocellular and cholangiocellular carcinoma. Skin cancer comprises but not limited to squamous cell carcinoma, Kaposi's sarcoma, malignant melanoma, Merkel cell skin cancer and non-melanoma skin cancer. Head and neck cancer comprises but not limited to throat/hypopharyngeal/nasopharyngeal/oropharyngeal cancer, and lip and oral cavity cancer. Lymphoma comprises but not limited to AIDS-related lymphoma, Non-Hodgkin's lymphoma, cutaneous T-cell lymphoma, Hodgkin's disease, and central nervous system lymphoma. Sarcoma comprises but not limited to soft tissue sarcoma, osteosarcoma, malignant fibrous histiotoma, lymphosarcoma and rhabdomyosarcoma. Leukemia comprises but not limited to acute myeloid leukemia, acute lymphocytic leukemia, chronic lymphocytic leukemia, chronic lymphocytic leukemia and hairy cell leukemia.

In the present application, the term "about" generally means variations within a range of 0.5%-10% above or below a specified numeric value, for example, variations within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below a specified numeric value.

In the present application, the term "comprises" generally means the meaning of comprising, embracing, comprising or encompassing. In some cases, it also indicates the meaning of "is/are" or "is/are composed of".

Antibody or an Antigen Binding Fragment Thereof

In one aspect, the present application provides an antibody specifically binding CD137 or an antigen binding fragment thereof, comprising a light chain variable region VL and a heavy chain variable region VH, in which compared to a sequence as set forth in SEQ ID NO: 103, the VL comprises one or more VL amino acid mutations occurring at one or more positions selected from a group consisting of: V3, A10, K44, D71 and V77.

In the present application, the VL amino acid mutations may comprise VL amino acid mutations occurring at positions A10 and V77. For example, the VL amino acid mutations may comprise VL amino acid mutations at positions of any one group below: 1) V3, D71 and V77; 2) A10 and V77; 3) D71; 4) A10, D71 and V77; 5) D71 and V77; 6) A10 and D71; or 7) V3, A10, K44, D71 and V77.

In the present application, compared to a sequence as set forth in SEQ ID NO: 127, the VH may comprise one or more VH amino acid mutations occurring at one or more positions selected from a group consisting of: Q13, N78, H84, D86, A90 and F97.

In the present application, the VH amino acid mutations may comprise a VH amino acid mutation occurring at position Q13. In the present application, the VH amino acid mutations may further comprise a VH amino acid mutation occurring at position N78.

For example, the VH amino acid mutation comprises VH amino acid mutations at positions of any one group below: 1) N78; 2) N78, H84, and D86; 3) Q13, N78, H84 and D86; 4) Q13 and N78; 5) Q13, H84, D86, A90 and F97; or 6) Q13, N78, H84, D86, A90 and F97.

For another example, in the antibody or the antigen binding fragment thereof of the present application, the VL amino acid mutation and the VH amino acid mutation may respectively comprises amino acid mutations at positions of any one of the following groups, respectively: 1) VL: V3, D71 and V77, and VH: N78; 2) VL: D71, and VH: N78, H84 and D86; 3) VL: D71 and V77, and VH: N78, H84 and D86; 4) VL: A10, D71 and V77, and VH: N78, H84 and D86; 5) VL: A10 and D71, and VH: Q13, N78, H84 and D86; 6) VL: V3, A10, K44, D71 and V77, and VH: Q13 and N78; 7) VL: A10 and V77, and VH: Q13, H84, D86, A90 and F97; or 8) VL: A10 and V77, and VH: Q13, N78, H84, D86, A90 and F97.

In the present application, the VL amino acid mutation at V3 may be selected from: V3A, V3M, V3G. In the present application, the VL amino acid mutation at A10 may be selected from: A10V, A10L, A10I. In the present application, the VL amino acid mutation at K44 may be selected from: K44T, K44G. In the present application, the VL amino acid mutation at D71 may be selected from: D71N, D71Q. In the present application, the VL amino acid mutation at V77 may be selected from: V77I. In the present application, the VH amino acid mutation at Q13 may be selected from: Q13K, Q13R. In the present application, the VH amino acid mutation at N78 may be selected from: N78K, N78D. In the present application, the VH amino acid mutation at H84 may be selected from: H84Q, H84E. In the present application, the VH amino acid mutation at D86 may be selected from: D86N, D86E. In the present application, the VH amino acid mutation at A90 may be selected from: A90T, A90S. In the present application, the VH amino acid mutation at F97 may be selected from: F97Y, F97W.

In the present application, the VL amino acid mutations may comprise VL amino acid mutations of any one group below: 1) V3A, D71N and V77I; 2) A10V and V77I; 3) D71N; 4) A10V, D71N and V77I; 5) D71N and V77I; 6) A10V and D71N; or 7) V3A, A10V, K44T, D71N and V77I.

In the present application, the VH amino acid mutations may comprise VH amino acid mutations of any one group below: 1) N78K; 2) N78K, H84Q and D86N; 3) Q13K, N78K, H84Q and D86N; 4) Q13K and N78K; or 5) Q13K, H84Q, D86N, A90T and F97Y.

For example, the VL amino acid mutations and the VH amino acid mutations may respectively comprise amino acid mutations of any one group below: 1) VL: V3A, D71N and V77I, and VH: N78K; 2) VL: D71N, and VH: N78K, H84Q and D86N; 3) VL: D71N and V77I, and VH: N78K, H84Q and D86N; 4) VL: A10V, D71N and V77I, and VH: N78K, H84Q and D86N; 5) VL: A10V and D71N, and VH: Q13K, N78K, H84Q and D86N; 6) VL: V3A, A10V, K44T, D71N and V77I, and VH: Q13K and N78K; 7) VL: A10V and V77I, and VH: Q13K, H84Q, D86N, A90T and F97Y; or 8) VL: A10V and V77I, and VH: Q13K, N78K, H84Q, D86N, A90T and F97Y.

In the present application, the VL may comprise an amino acid sequence as set forth in any one of SEQ ID NOs: 104-114. In the present application, the VL may comprise an amino acid sequence as set forth in any one of SEQ ID NOs: 104, 106, 108 and 110-114.

In the present application, the VH may comprise an amino acid sequence as set forth in any one of SEQ ID NOs: 128-138. In the present application, the VH may comprise an amino acid sequence as set forth in any one of SEQ ID NOs: 128, 130, 132 and 134-138.

For example, in the antibody of the present application: 1) the VL may comprise an amino acid sequence as set forth in SEQ ID NO: 104, and the VH may comprise an amino acid sequence as set forth in SEQ ID NO: 128; 2) the VL may comprise an amino acid sequence as set forth in SEQ ID NO: 106, and the VH may comprise an amino acid sequence as set forth in SEQ ID NO: 130; 3) the VL may comprise an amino acid sequence as set forth in SEQ ID NO: 108, and the VH may comprise an amino acid sequence as set forth in SEQ ID NO: 132; 4) the VL may comprise an amino acid sequence as set forth in SEQ ID NO: 110, and the VH may comprise an amino acid sequence as set forth in SEQ ID NO: 134; 5) the VL may comprise an amino acid sequence as set forth in SEQ ID NO: 111, and the VH may comprise an amino acid sequence as set forth in SEQ ID NO: 135; 6) the VL may comprise an amino acid sequence as set forth in SEQ ID NO: 112, and the VH may comprise an amino acid sequence as set forth in SEQ ID NO: 136; 7) the VL may comprise an amino acid sequence as set forth in SEQ ID NO: 113, and the VH may comprise an amino acid sequence as set forth in SEQ ID NO: 137; or 8) the VL may comprise an amino acid sequence as set forth in SEQ ID NO: 114, and the VH may comprise an amino acid sequence as set forth in SEQ ID NO: 138.

In the present application, the antibody or the antigen binding fragment thereof may comprise HFR1-4, the sequences of which are as set forth in SEQ ID NOs: 7-10 respectively; the antibody or the antigen binding fragment thereof may comprise LFR1-4, the sequences of which are as set forth in SEQ ID NOs: 11-14 respectively. For example, the antibody or the antigen binding fragment thereof may comprise an antibody C2-WT-Fc or the antibody of the present application having a VL comprising an amino acid sequence as set forth in SEQ ID: 103 and/or a VH comprising an amino acid sequence as set forth in SEQ ID: 127.

In the present application, the antibody or the antigen binding fragment thereof may comprise HFR1-4, the sequences of which are as set forth in SEQ ID NOS: 15-18 respectively; the antibody or the antigen binding fragment thereof may comprise LFR1-4, the sequences of which are as set forth in SEQ ID NOs: 19-22 respectively. For example, the antibody or the antigen binding fragment thereof may comprise an antibody C2-4A-Fc or the antibody of the present application having a VL comprising an amino acid sequence as set forth in SEQ ID: 104 and/or a VH comprising an amino acid sequence as set forth in SEQ 128.

In the present application, the antibody or the antigen binding fragment thereof may comprise HFR1-4, the sequences of which are as set forth in SEQ ID NOs: 23-26 respectively; the antibody or the antigen binding fragment thereof may comprise LFR1-4, the sequences of which are as set forth in SEQ ID NOs: 27-30 respectively. For example, the antibody or the antigen binding fragment thereof may comprise an antibody C2-4B-Fc or/and the antibody of the present application having a VL comprising an amino acid sequence as set forth in SEQ ID: 105 and/or a VH comprising an amino acid sequence as set forth in SEQ 129.

In the present application, the antibody or the antigen binding fragment thereof may comprise HFR1-4, the sequences of which are as set forth in SEQ ID NOs: 31-34 respectively; the antibody or the antigen binding fragment thereof may comprise LFR1-4, the sequences of which are as set forth in SEQ ID NOs: 35-38 respectively. For example, the antibody or the antigen binding fragment thereof may comprise an antibody C2-4C-Fc or the antibody of the present application having a VL comprising an amino acid sequence as set forth in SEQ ID: 106 and/or a VH comprising an amino acid sequence as set forth in SEQ ID: 130.

In the present application, the antibody or the antigen binding fragment thereof may comprise HFR1-4, the sequences of which are as set forth in SEQ ID NOs: 39-42 respectively; the antibody or the antigen binding fragment thereof may comprise LFR1-4, the sequences of which are as set forth in SEQ ID NOs: 43-46 respectively. For example, the antibody or the antigen binding fragment thereof may comprise an antibody C2-5A-Fc or the antibody of the present application having a VL comprising an amino acid sequence as set forth in SEQ ID: 107 and/or a VH comprising an amino acid sequence as set forth in SEQ ID: 131.

In the present application, the antibody or the antigen binding fragment thereof may comprise HFR1-4, the sequences of which are as set forth in SEQ ID NOs: 47-50 respectively; the antibody or the antigen binding fragment thereof may comprise LFR1-4, the sequences of which are as set forth in SEQ ID NOs: 51-54 respectively. For example, the antibody or the antigen binding fragment thereof may comprise an antibody C2-5B-Fc or the antibody of the present application having a VL comprising an amino acid sequence as set forth in SEQ ID: 108 and/or a VH comprising an amino acid sequence as set forth in SEQ ID: 132.

In the present application, the antibody or the antigen binding fragment thereof may comprise HFR1-4, the sequences of which are as set forth in SEQ ID NOs: 55-58 respectively; the antibody or the antigen binding fragment thereof may comprise LFR1-4, the sequences of which are as set forth in SEQ ID NOs: 59-62 respectively. For example, the antibody or the antigen binding fragment thereof may comprise an antibody C2-5C-Fc or the antibody of the present application having a VL comprising an amino acid sequence as set forth in SEQ ID: 109 and/or a VH comprising an amino acid sequence as set forth in SEQ 133.

In the present application, the antibody or the antigen binding fragment thereof may comprise HFR1-4, the sequences of which are as set forth in SEQ ID NOs: 63-66 respectively; the antibody or the antigen binding fragment thereof may comprise LFR1-4, the sequences of which are as set forth in SEQ ID NOs: 67-70 respectively. For example, the antibody or the antigen binding fragment thereof may comprise an antibody C2-6A-Fc or the antibody of the present application having a VL comprising an amino acid sequence as set forth in SEQ ID: 110 and/or a VH comprising an amino acid sequence as set forth in SEQ ID: 134.

In the present application, the antibody or the antigen binding fragment thereof may comprise HFR1-4, the sequences of which are as set forth in SEQ ID NOs: 71-74 respectively; the antibody or the antigen binding fragment thereof may comprise LFR1-4, the sequences of which are as set forth in SEQ ID NOs: 75-78 respectively. For example, the antibody or the antigen binding fragment thereof may comprise an antibody C2-6B-Fc or the antibody of the present application having a VL comprising an amino acid sequence as set forth in SEQ ID: 111 and/or a VH comprising an amino acid sequence as set forth in SEQ 135.

In the present application, the antibody or the antigen binding fragment thereof may comprise HFR1-4, the sequences of which are as set forth in SEQ ID NOs: 79-82 respectively; the antibody or the antigen binding fragment thereof may comprise LFR1-4, the sequences of which are as set forth in SEQ ID NOs: 83-86 respectively. For example, the antibody or the antigen binding fragment thereof may comprise an antibody C2-7A-Fc or the antibody of the present application having a VL comprising an amino acid sequence as set forth in SEQ ID: 112 and/or a VH comprising an amino acid sequence as set forth in SEQ 136.

In the present application, the antibody or the antigen binding fragment thereof may comprise HFR1-4, the sequences of which are as set forth in SEQ ID NOs: 87-90 respectively; the antibody or the antigen binding fragment thereof may comprise LFR1-4, the sequences of which are as set forth in SEQ ID NOs: 91-94 respectively. For example, the antibody or the antigen binding fragment thereof may comprise an antibody C2-7B-Fc or the antibody of the present application having a VL comprising an amino acid sequence as set forth in SEQ ID: 113 and/or a VH comprising an amino acid sequence as set forth in SEQ 137.

In the present application, the antibody or the antigen binding fragment thereof may comprise HFR1-4, the sequences of which are as set forth in SEQ ID NOs: 95-98 respectively; the antibody or the antigen binding fragment thereof may comprise LFR1-4, the sequences of which are as set forth in SEQ ID NOs: 99-102 respectively. For example, the antibody or the antigen binding fragment thereof may comprise an antibody C2-7BN78K-Fc or the antibody of the present application having a VL comprising an amino acid sequence as set forth in SEQ ID: 114 and/or a VH comprising an amino acid sequence as set forth in SEQ 138.

In the present application, the amino acid sequence of LCDR1 in the antibody or the antigen binding fragment thereof of the present application may comprise SEQ ID NO: 1 or a variant thereof; the amino acid sequence of LCDR2 may comprise SEQ ID NO: 2 or a variant thereof; the amino acid sequence of LCDR3 may comprise SEQ ID NO: 3 or a variant thereof; and the amino acid sequence of HCDR1 may comprise SEQ ID NO: 4 or a variant thereof; the amino acid sequence of HCDR2 may comprise SEQ ID NO: 5 or a variant thereof the amino acid sequence of HCDR3 may comprise SEQ ID NO: 6 or a variant thereof. For example, the antibody or the antigen binding fragment thereof may comprise antibodies C2-WT-Fc, C2-4A-Fc, C2-4B-Fc, C2-4C-Fc, C2-5A-Fc, C2-5B-Fc, C2-5C-Fc, C2-6A-Fc, C2-6B-Fc, C2-7A-Fc, C2-7B-Fc, C2-7BN78K-Fc or the antibody of the present application having LCDR1-3 comprising amino acid sequences as set forth in SEQ IDs: 1-3 and/or HCDR1-3 comprising amino acid sequences as set forth in SEQ IDs: 4-6.

In the present application, the sequence of Fc in the antibody or the antigen binding fragment thereof of the present application comprises SEQ ID NO: 163, SEQ ID NO: 164 or a variant thereof. For example, the antibody or the antigen binding fragment thereof may comprise antibodies C2-WT-Fc, C2-4A-Fc, C2-4B-Fc, C2-4C-Fc, C2-5A-Fc, C2-5B-Fc, C2-5C-Fc, C2-6A-Fc, C2-6B-Fc, C2-7A-Fc, C2-7B-Fc, C2-7BN78K or the antibody of the present application having a Fc comprising an amino acid sequence as set forth in SEQ ID: 164.

In the present application, a linker peptide is further comprised between the light chain variable region and the heavy chain variable region in the antibody or the antigen binding fragment thereof of the present application, which may comprise SEQ ID NO: 165 or a variant thereof. For example, a linker peptide may comprise (G4S)3. A linker peptide may be further comprised between the light chain variable region and Fc in the antibody or the antigen binding fragment thereof of the present application, which may comprise SEQ ID NO: 166 or a variant thereof. For example, the linker peptide may comprise G4S. For example, the antibody or the antigen binding fragment thereof may comprise antibodies C2-WT-Fc, C2-4A-Fc, C2-4B-Fc, C2-4C-Fc, C2-5A-Fc, C2-5B-Fc, C2-5C-Fc, C2-6A-Fc, C2-6B-Fc, C2-7A-Fc, C2-7B-Fc, C2-7BN78K-Fc or/and the antibody of the present application having the linker peptide (G4S)3 comprising an amino acid sequence as set forth in SEQ ID: 165 and/or the linker peptide G4S comprising an amino acid sequence as set forth in SEQ ID: 166.

In some embodiments, the light chain in the antibody or the antigen binding fragment thereof of the present application may comprise a light chain variable region, the amino acid sequence of the light chain variable region may comprise SEQ ID NO: 103 or a variant thereof; and in which the heavy chain may comprise a heavy chain variable region, the amino acid sequence of the heavy chain variable region may comprise SEQ ID NO: 127 or a variant thereof. For example, the antibody or the antigen binding fragment thereof may comprise an antibody C2-WT-Fc or the antibody of the present application having the same light chain variable region and the same heavy chain variable region as those in the antibody C2-WT-Fc.

For example, the antibody of the present application may be C2-WT-Fc. The amino acid sequences of LCDR1-3 in the antibody C2-WT-Fc are as set forth in SEQ ID NOs: 1-3 respectively; the amino acid sequences of LFR1-4 are as set forth in SEQ ID NOs: 11-14 respectively; the amino acid sequence of VL is as set forth in SEQ ID NO: 103; the amino acid sequences of HCDR1-3 are as set forth in SEQ ID NOs: 4-6 respectively; the amino acid sequences of HFR1-4 are as set forth in SEQ ID NOs: 7-10 respectively; the amino acid sequence of VH is as set forth in SEQ ID NO: 127; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 104 or a variant thereof; and in which the heavy chain may comprise a heavy chain variable region, the amino acid sequence of the heavy chain variable region may comprise an amino acid sequence as set forth in SEQ ID NO: 128 or a variant thereof. For example, the antibody or the antigen binding fragment thereof may comprise an antibody C2-4A-Fc or the antibody of the present application having the same light chain variable region and the same heavy chain variable region as those in the antibody C2-4A-Fc.

For example, the antibody of the present application may be C2-4A-Fc. The amino acid sequences of LCDR1-3 in the antibody C2-4A-Fc are as set forth in SEQ ID NOs: 1-3 respectively; the amino acid sequences of LFR1-4 are as set forth in SEQ ID NOs: 19-22 respectively; the amino acid sequence of VL is as set forth in SEQ ID NO: 104; the amino acid sequences of HCDR1-3 are as set forth in SEQ ID NOs: 4-6 respectively; the amino acid sequences of HFR1-4 are as set forth in SEQ ID NOs: 15-18 respectively; the amino acid sequence of VH is as set forth in SEQ ID NO: 128; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 105 or a variant thereof; and in which the heavy chain may comprise a heavy chain variable region, the amino acid sequence of the heavy chain variable region may comprise an amino acid sequence as set forth in SEQ ID NO: 129 or a variant thereof. For example, the antibody or the antigen binding fragment thereof may comprise an antibody C2-4B-Fc or the antibody of the present application having the same light chain variable region and the same heavy chain variable region as those in the antibody C2-4B-Fc.

For example, the antibody of the present application may be C2-4B-Fc. The amino acid sequences of LCDR1-3 in the antibody C2-4B-Fc are as set forth in SEQ ID NOs: 1-3 respectively; the amino acid sequences of LFR1-4 are as set forth in SEQ ID NOs: 11-14 respectively; the amino acid sequence of VL is as set forth in SEQ ID NO: 105; the amino acid sequences of HCDR1-3 are as set forth in SEQ ID NOs: 4-6 respectively; the amino acid sequences of HFR1-4 are as set forth in SEQ ID NOs: 23-26 respectively; the amino acid sequence of VH is as set forth in SEQ ID NO: 129; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 106 or a variant thereof; and in which the heavy chain may comprise a heavy chain variable region, the amino acid sequence of the heavy chain variable region may comprise an amino acid sequence as set forth in SEQ ID NO: 130 or a variant thereof. For example, the antibody or the antigen binding fragment thereof may comprise an antibody C2-4C-Fc or the antibody of the present application having the same light chain variable region and the same heavy chain variable region as those in the antibody C2-4C-Fc.

For example, the antibody of the present application may be C2-4C-Fc. The amino acid sequences of LCDR1-3 in the antibody C2-4C-Fc are as set forth in SEQ ID NOs: 1-3 respectively; the amino acid sequences of LFR1-4 are as set forth in SEQ ID NOs: 35-38 respectively; the amino acid sequence of VL is as set forth in SEQ ID NO: 106; the amino acid sequences of HCDR1-3 are as set forth in SEQ ID NOs: 4-6 respectively; the amino acid sequences of HFR1-4 are as set forth in SEQ ID NOs: 31-34 respectively; the amino acid sequence of VH is as set forth in SEQ ID NO: 130; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 107 or a variant thereof; and in which the heavy chain may comprise a heavy chain variable region, the amino acid sequence of the heavy chain variable region may comprise an amino acid sequence as set forth in SEQ ID NO: 131 or a variant thereof. For example, the antibody or the antigen binding fragment thereof may comprise an antibody C2-5A-Fc or the antibody of the present application having the same light chain variable region and the same heavy chain variable region as those in the antibody C2-5A-Fc.

For example, the antibody of the present application may be C2-5A-Fc. The amino acid sequences of LCDR1-3 in the antibody C2-5A-Fc are as set forth in SEQ ID NOs: 1-3 respectively; the amino acid sequences of LFR1-4 are as set forth in SEQ ID NOs: 43-46 respectively; the amino acid sequence of VL is as set forth in SEQ ID NO: 107; the amino acid sequences of HCDR1-3 are as set forth in SEQ ID NOs: 4-6 respectively; the amino acid sequences of HFR1-4 are as set forth in SEQ ID NOs: 39-42 respectively; the amino acid sequence of VH is as set forth in SEQ ID NO: 131; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 108 or a variant thereof; and in which the heavy chain may comprise a heavy chain variable region, the amino acid sequence of the heavy chain variable region may comprise an amino acid sequence as set forth in SEQ ID NO: 132 or a variant thereof. For example, the antibody or the antigen binding fragment thereof may comprise an antibody C2-5B-Fc or the antibody of the present application having the same light chain variable region and the same heavy chain variable region as those in the antibody C2-5B-Fc.

For example, the antibody of the present application may be C2-5B-Fc. The amino acid sequences of LCDR1-3 in the antibody C2-5B-Fc are as set forth in SEQ ID NOs: 1-3 respectively; the amino acid sequences of LFR1-4 are as set forth in SEQ ID NOs: 51-54 respectively; the amino acid sequence of VL is as set forth in SEQ ID NO: 108; the amino acid sequences of HCDR1-3 are as set forth in SEQ ID NOs: 4-6 respectively; the amino acid sequences of HFR1-4 are as set forth in SEQ ID NOs: 47-50 respectively; the amino acid sequence of VH is as set forth in SEQ ID NO: 132; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 109 or a variant thereof; and in which the heavy chain may comprise a heavy chain variable region, the amino acid sequence of the heavy chain variable region may comprise an amino acid sequence as set forth in SEQ ID NO: 133 or a variant thereof. For example, the antibody or the antigen binding fragment thereof may comprise an antibody C2-5C-Fc or the antibody of the present application having the same light chain variable region and the same heavy chain variable region as those in the antibody C2-5C-Fc.

For example, the antibody of the present application may be C2-5C-Fc. The amino acid sequences of LCDR1-3 in the antibody C2-5C-Fc are as set forth in SEQ ID NOs: 1-3 respectively; the amino acid sequences of LFR1-4 are as set forth in SEQ ID NOs: 59-62 respectively; the amino acid sequence of VL is as set forth in SEQ ID NO: 109; the amino acid sequences of HCDR1-3 are as set forth in SEQ ID NOs: 4-6 respectively; the amino acid sequences of HFR1-4 are as set forth in SEQ ID NOs: 55-58 respectively; the amino acid sequence of VH is as set forth in SEQ ID NO: 133; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise SEQ ID NO: 110 or a variant thereof; and in which the heavy chain may comprise a heavy chain variable region, the amino acid sequence of the heavy chain variable region may comprise SEQ ID NO: 134 or a variant thereof. For example, the antibody or the antigen binding fragment thereof may comprise an antibody C2-6A-Fc or the antibody of the present application having the same light chain variable region and the same heavy chain variable region as those in the antibody C2-6A-Fc.

For example, the antibody of the present application may be C2-6A-Fc. The amino acid sequences of LCDR1-3 in the antibody C2-6A-Fc are as set forth in SEQ ID NOs: 1-3 respectively; the amino acid sequences of LFR1-4 are as set forth in SEQ ID NOs: 67-70 respectively; the amino acid sequence of VL is as set forth in SEQ ID NO: 110; the amino acid sequences of HCDR1-3 are as set forth in SEQ ID NOs: 4-6 respectively; the amino acid sequences of HFR1-4 are as set forth in SEQ ID NOs: 63-66 respectively; the amino acid sequence of VH is as set forth in SEQ ID NO: 134; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 111 or a variant thereof; and in which the heavy chain may comprise a heavy chain variable region, the amino acid sequence of the heavy chain variable region may comprise an amino acid sequence as set forth in SEQ ID NO: 135 or a variant thereof. For example, the antibody or the antigen binding fragment thereof may comprise an antibody C2-6B-Fc or the antibody of the present application having the same light chain variable region and the same heavy chain variable region as those in the antibody C2-6B-Fc.

For example, the antibody of the present application may be C2-6B-Fc. The amino acid sequences of LCDR1-3 in the antibody C2-6B-Fc are as set forth in SEQ ID NOs: 1-3 respectively; the amino acid sequences of LFR1-4 are as set forth in SEQ ID NOs: 75-78 respectively; the amino acid sequence of VL is as set forth in SEQ ID NO: 111; the amino acid sequences of HCDR1-3 are as set forth in SEQ ID NOs: 4-6 respectively; the amino acid sequences of HFR1-4 are as set forth in SEQ ID NOs: 71-74 respectively; the amino acid sequence of VH is as set forth in SEQ ID NO: 135; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 112 or a variant thereof; and in which the heavy chain may comprise a heavy chain variable region, the amino acid sequence of the heavy chain variable region may comprise an amino acid sequence as set forth in SEQ ID NO: 136 or a variant thereof. For example, the antibody or the antigen binding fragment thereof may comprise an antibody C2-7A-Fc or the antibody of the present application having the same light chain variable region and the same heavy chain variable region as those in the antibody C2-7A-Fc.

For example, the antibody of the present application may be C2-7A-Fc. The amino acid sequences of LCDR1-3 in the antibody C2-7A-Fc are as set forth in SEQ ID NOs: 1-3 respectively; the amino acid sequences of LFR1-4 are as set forth in SEQ ID NOs: 83-86 respectively; the amino acid sequence of VL is as set forth in SEQ ID NO: 112; the amino acid sequences of HCDR1-3 are as set forth in SEQ ID NOs: 4-6 respectively; the amino acid sequences of HFR1-4 are as set forth in SEQ ID NOs: 79-82 respectively; the amino acid sequence of VH is as set forth in SEQ ID NO: 136; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 113 or a variant thereof; and in which the heavy chain may comprise a heavy chain variable region, the amino acid sequence of the heavy chain variable region may comprise an amino acid sequence as set forth in SEQ ID NO: 137 or a variant thereof. For example, the antibody or the antigen binding fragment thereof may comprise an antibody C2-7B-Fc or the antibody of the present application having the same light chain variable region and the same heavy chain variable region as those in the antibody C2-7B-Fc.

For example, the antibody of the present application may be C2-7B-Fc. The amino acid sequences of LCDR1-3 in the antibody C2-7B-Fc are as set forth in SEQ ID NOs: 1-3 respectively; the amino acid sequences of LFR1-4 are as set forth in SEQ ID NOs: 91-94 respectively; the amino acid sequence of VL is as set forth in SEQ ID NO: 113; the amino acid sequences of HCDR1-3 are as set forth in SEQ ID NOs: 4-6 respectively; the amino acid sequences of HFR1-4 are as set forth in SEQ ID NOs: 87-90 respectively; the amino acid sequence of VH is as set forth in SEQ ID NO: 137; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some embodiments, the light chain in the antibody or the antigen binding fragment thereof of the present application may comprise a light chain variable region, the amino acid sequence of the light chain variable region may comprise an amino acid sequence as set forth in SEQ ID NO: 114 or a variant thereof; and in which the heavy chain may comprise a heavy chain variable region, the amino acid sequence of the heavy chain variable region may comprise an amino acid sequence as set forth in SEQ ID NO: 138 or a variant thereof. For example, the antibody or the antigen binding fragment thereof may comprise an antibody C2-7BN78K-Fc or the antibody of the present application having the same light chain variable region and the same heavy chain variable region as those in the antibody C2-7BN78K-Fc.

For example, the antibody of the present application may be C2-7BN78K-Fc. The amino acid sequences of LCDR1-3 in the antibody C2-7BN78K-Fc are as set forth in SEQ ID NOs: 1-3 respectively; the amino acid sequences of LFR1-4 are as set forth in SEQ ID NOs: 99-102 respectively; the amino acid sequence of VL is as set forth in SEQ ID NO: 114; the amino acid sequences of HCDR1-3 are as set forth in SEQ ID NOs: 4-6 respectively; the amino acid sequences of HFR1-4 are as set forth in SEQ ID NOs: 95-98 respectively; the amino acid sequence of VH is as set forth in SEQ ID NO: 138; Fc sequence is as set forth in SEQ ID NO: 163; the linker peptide between VH and VL is (G4S)3, the sequence of which is as set forth in SEQ ID NO: 165; the linker peptide between VL and Fc is G4S, the sequence of which is as set forth in SEQ ID NO: 166.

In some cases, the antibody may be C2-7BN78K-Fc. The antibody C2-7BN78K-Fc may comprise a light chain variable region VL, in which compared to the sequence as set forth in SEQ ID NO: 103, the VL may comprise one or more VL amino acid mutations, comprising amino acid mutations of A10V and V77I. The antibody C2-7BN78K-Fc may comprise LCDR1-3, the amino acid sequences of which are as set forth in SEQ ID NOs: 1-3 respectively; the antibody C2-7BN78K-Fc may comprise LFR1-4, the amino acid sequences of which are as set forth in SEQ ID NOs: 99-102 respectively; the VL of the antibody C2-7BN78K-Fc may comprise an amino acid sequence as set forth in SEQ ID: 114. The antibody C2-7BN78K-Fc may comprise a heavy chain variable region VH, wherein compared to the sequence as set forth in SEQ ID NO: 127, the VH may comprise one or more VH amino acid mutations occurring at Q13K, N78K, H84Q, D86N, A90T and F97Y. The antibody C2-7BN78K-Fc may comprise HCDR1-3, the amino acid sequences of which are as set forth in SEQ ID NOs: 4-6 respectively; the antibody C2-7BN78K-Fc may comprise HFR1-4, the amino acid sequences of which are as set forth in SEQ ID NOs: 95-98 respectively; the VH of the antibody C2-7BN78K-Fc may comprise an amino acid sequence as set forth in SEQ ID: 138. The antibody C2-7BN78K-Fc may further comprise a Fc, the amino acid sequence of which is as set forth in SEQ ID NO: 163. In the antibody C2-7BN78K-Fc, the C-terminal of VH and the N-terminal of VL may be linked through a linker peptide which is (G4S)3 with a sequence as set forth in SEQ ID NO: 165; the C-terminal of VL and the N-terminal of Fc may be linked through a linker peptide which is G4S with a sequence as set forth in SEQ ID NO: 166.

In the present application, the variants of the amino acid sequences may be amino acid sequences having substantially the same functions (e.g., capable of specifically binding CD137 protein), and having sequence identities of at least about 85% (e.g., having sequence identities of at least about 85%, about 90%, about 91%, about 92%, about 93%, about 94%, about 95%, about 96%, about 97%, about 98%, about 99% or higher). In some embodiments, the variants of the amino acid sequences are amino acid sequences having substantially the same functions (e.g., capable of specifically binding CD137 protein), and furthermore comprising additions, deletions or replacements of one or more (e.g., 1-2, 1-3, 1-4, 1-5, 1-6, 1-7, 1-8, 1-9, 1-10 or more) amino acids.

In the present application, the antibody or the antigen binding fragment thereof may further comprise a Fc domain. For example, the antibody Fc region may comprise a Fc region of IgG. For example, the antibody Fc domain may comprise an amino acid sequence of a constant region of an immunoglobulin selected from: IgG1, IgG2, IgG3 and IgG4. In some embodiments, the Fc domain may comprise an amino acid sequence as set forth in SEQ ID NO: 163 or SEQ ID NO: 164.

Immunoconjugate, Nucleic Acid, Vector, Cell

In another aspect, the present application provides an immunoconjugate, which may comprise the antibody or the antigen binding fragment thereof.

In another aspect, the present application provides one or more isolated nucleic acid molecules, which may encode the antibody or the antigen binding fragment thereof of the present application. The nucleic acid molecules of the present application may be isolated. In some embodiments, the present application may comprise one isolated nucleic acid molecule. For example, a nucleic acid molecule encoding the antibody or the antigen binding fragment thereof of the present application may comprise, such as scFv-Fc. In some embodiments, the present application may comprise multiple isolated nucleic acid molecules. In the present application, the nucleic acid molecule of the present application may be produced or synthesized by the following processes: (i) amplification in vitro, e.g., being produced by amplification through polymerase chain reaction (PCR), (ii) being produced by cloning recombination, (iii) purification, e.g., fractional separation through enzyme digestion and gel electrophoresis, or (iv) synthesis, e.g., through chemical synthesis. In some embodiments, the isolated nucleic acid is nucleic acid molecule prepared by a recombinant DNA technology.

In another aspect, the present application provides one or more vectors, which may comprise the nucleic acid molecules of the present application. In addition, the vectors may further comprise other genes, e.g., marker genes allowing to select the vector in appropriate host cells and under suitable conditions. In addition, the vector may further comprise expression control elements allowing the coding region to be properly expressed in appropriate hosts. Such control elements are well known to those skilled in the art, for example comprising promoters, ribosome binding sites, enhancers and other control elements for regulating gene transcription or mRNA translation. In some embodiments, the expression control sequences are regulatable elements. The specific structures of the expression control sequences may vary depending on the species or the cell-type functions, but they generally comprise 5'non-transcriptional sequences and 5' and 3' non-translational sequences respectively participating in the initiation of transcription and translation, such as TATA cassettes, capped sequences, CAAT sequences, etc. For example, 5' non-transcriptional expression control sequences may comprise promoter regions, which may comprise promoter sequences for transcribing and controlling functionally-linked nucleic acids. The one or more nucleic acid molecules of the present application may be operably linked with the expression control elements. The vectors may comprise, for example, plasmids, cosmids, viruses, phages or other vectors commonly used in genetic engineering for example. For example, the vectors are expression vectors.

In another aspect, the present application provides a cell, which may comprise the one or more vectors of the present application. In some embodiments, each kind of or each cell may comprise one or one kind of the vectors of the present application. In some embodiments, each kind of or each cell may comprise multiple (e.g., two or more) or multiple kinds of (e.g., 2 or more kinds of) the vectors of the present application. For example, each cell may comprise one vector, which may comprise the nucleic acid molecules of the present application. For example, each cell may comprise a vector fused with the nucleotide encoding the antibody or the antigen binding fragment thereof of the present application. Further for example, each cell may comprise multiple vectors, which may comprise vectors fused with human IgG4-Fc genes and vectors fused with scFv-Fc molecule genes. In some embodiments of the present application, for example, the vectors of the present application may be introduced into the cells, e.g., eukaryotic cells (e.g., mammalian cells). For example, the mammalian cells may be HEK293 cells. The vector of the present application may be introduced into the cells through the methods well known in the art, e.g., electroporation, lipofectine transfection, lipofectamin transfection, etc.

Pharmaceutical Composition and Pharmaceutical Uses

In another aspect, the present application provides a pharmaceutical composition, which may comprise the antibody or the antigen binding fragment thereof of the present application, the immunoconjugate of the present application, or the nucleic acid molecule of the present application, the cell of the present application, and optionally a pharmaceutically acceptable adjuvant. The pharmaceutically acceptable adjuvant may comprise buffering agents, antioxidants, preservatives, low molecular weight polypeptides, proteins, hydrophilic polymers, amino acids, sugars, chelating agents, counter-ions, metal complexes and/or nonionic surfactants, and the like. In the present application, the pharmaceutical composition may be formulated for oral administration, intravenous administration, intramuscular administration, in situ administration at tumor sites, inhalation, rectal administration, vaginal administration, transdermal administration or administration through subcutaneous reservoir.

In another aspect, the present application provides a use of the antibody or the antigen binding fragment thereof of the present application in preparing a drug, in which the drug is used for treating cancers. In another aspect, the present application provides an application of the antibody or the antigen binding fragment thereof of the present application in treating cancers. In another aspect, the present application provides a method of treating cancers which comprises administrating the antibody or the antigen binding fragment thereof of the present application.

For example, the growth of tumors may be inhibited by preparing a drug comprising the antibody or the antigen binding fragment thereof of the present application and inoculating subcutaneously at regular intervals. For example, the administration may be twice a week, once a week, three times a week, or once every two weeks, etc. The administration dosage for each time may be about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 2.0 mg/kg, about 3.0 mg/kg, about 4.0 mg/kg, about 5.0 mg/kg, etc. In some embodiments, the cancers may be selected from a group consisting of: melanoma, prostatic cancer, colorectal cancer, Merkel cell skin cancer, pancreatic cancer, Non-Hodgkin's lymphoma, squamous cell carcinoma, breast cancer, and the like.

formed in the FR regions of VH and VL respectively according to the model of homology modeling, and the free energies were calculated for the point-mutated sequences. At the same time, the homology between the mutated sequences and human germ lines was compared on the IMGT web site (http://www.imgt.org/). All the mutations were ranked according to the free energies and the homologies with human germ lines, and 10 molecules with the highest stability were sorted based on the free energies and the homology ranking, in which the free energies and the homology ranking are as set forth in FIG. 1. The mutations on the anti-CD137 antibody molecules are specifically shown in Table 1 and FIG. 1.

TABLE 1

Types of anti-CD137 antibody molecule mutations

| Name | VL mutation | VL | VH mutation | VH | Complete sequence |
|---|---|---|---|---|---|
| C2-4A-Fc | V3A + D71N + V77I | SEQ ID No: 104 | N78K | SEQ ID No: 128 | SEQ ID No: 152 |
| C2-4B-Fc | A10V + V77I | SEQ ID No: 105 | G16R + I37F | SEQ ID No: 129 | SEQ ID No: 153 |
| C2-4C-Fc | D71N | SEQ ID No: 106 | N78K + H84Q + D86N | SEQ ID No: 130 | SEQ ID No: 154 |
| C2-5A-Fc | A10V + D71N + V77I | SEQ ID No: 107 | G16R + N78K | SEQ ID No: 131 | SEQ ID No: 155 |
| C2-5B-Fc | D71N + V77I | SEQ ID No: 108 | N78K + H84Q + D86N | SEQ ID No: 132 | SEQ ID No: 156 |
| C2-5C-Fc | A10V + V77I | SEQ ID No: 109 | G16R + I37F + F97Y | SEQ ID No: 133 | SEQ TDNo: 157 |
| C2-6A-Fc | A10V + D71N + V77I | SEQ ID No: 110 | N78K + H84Q + D86N | SEQ ID No: 134 | SEQ ID No: 158 |
| C2-6B-Fc | A10V + D71N | SEQ ID No: 111 | Q13K + N78K + H84Q + D86N | SEQ ID No: 135 | SEQ ID No: 159 |
| C2-7A-Fc | V3A + A10V + K44T + D71N + V77I | SEQ ID No: 112 | Q13K + N78K | SEQ ID No: 136 | SEQ ID No: 160 |
| C2-7B-Fc | A10V + V77I | SEQ ID No: 113 | Q13K + H84Q + D86N + A90T + F97Y | SEQ ID No: 137 | SEQ ID No: 161 |
| C2-7BN78K-Fc | A10V + V77I | SEQ ID No: 114 | Q13K + N78K + H84Q + D86N + A90T + F97Y | SEQ ID No: 138 | SEQ ID No: 162 |

Without intending to be limited by any theories, the examples below are only listed for interpreting the working modes of the antibody or the antigen binding fragment, the vector, the cell and the pharmaceutical composition of the present application, rather than limiting the scope of the present application.

EXAMPLES

Example 1

Construction of Anti-CD137 Antibody Mutant Molecules 1.1 Design of Anti-CD137 Antibody Mutations Amino acid mutations were introduced into specific positions in the VH and VL (as set forth in SEQ ID NOs: 127 and 103 respectively) of the anti-CD137 antibody molecule (C2-WT), and the scFv fragment of the antibody molecule was then fused with a Fc fragment. Homology modeling was performed on C2-WT-Fc with the use of a swiss-model, and the free energy was calculated. Point mutations were per- 1.2 Expression of Recombinant Human CD137 and Preparation of EGFP Cells The amino acid sequence of human CD137 extracellular domain (i.e., residues at positions 1 to 186 of Q07011) was obtained according to the amino acid sequence (Q07011) of human CD137 on the protein database Uniprot; the amino acid sequence of mouse IgG1-Fc (muFc) domain (i.e., residues at positions 98 to 324 of P01868) was obtained according to the amino acid sequence (P01868) of the mouse immunoglobulin gamma (γ) 1 (IgG1) constant region on the protein database Uniprot. With the use of a DNAworks online tool (http://helixweb.nih.gov/dnaworks/), corresponding encoding DNA sequences were designed to get the gene of hCD137-muFc fusion protein. The amino acid sequence (C5MKY7) of enhanced green fluorescent protein (EGFP) was obtained according to the information on the protein database Uniprot, and a DNAworks online tool (http://helixweb.nih.gov/dnaworks/) was employed to design corresponding encoding DNA sequences to get the gene of hCD137-EGFP fusion protein. The desired DNA fragments were obtained by means of artificial synthesis, and the synthesized gene sequences were respectively subcloned into a commercialized vector pcDNA4/myc-HisA (Invitrogen, V863-20) by double digestion with Hind III and EcoR I from Fermentas Co. The accuracy of the constructed plasmids was verified by sequencing to get recombinant plasmid DNA, i.e.: pcDNA4-hCD137-muFc and pcDNA4-hCD137-EGFP. The hCD137-EGFP recombinant plasmid was transfected into HEK 293 (ATCC, CRL-1573™) cells, and 48 hours after transfection, the expression of hCD137 was confirmed through fluorescence activated cell sorting (FACS).

The pcDNA4-hCD137-muFc was transiently transfected into HEK 293 cells for the production of protein. The recombinant expression plasmids were diluted with Freestyle 293 culture medium and added into a PEI (Polyethylenimine) solution required for conversion. Each group of plasmid/PEI mixture was added into the cell suspension respectively and cultured at 90 rpm, at 37° C. and 10% $CO_2$ for 5-6 days. The transiently expressed culture supernatants were collected and purified primarily by Protein A affinity chromatography to get hCD137-muFc protein samples, which are used in the following examples. The obtained protein samples were detected primarily by SDS-PAGE so that the target bands may be observed clearly.

1.3 Expression of Anti-CD137 Antibody

For ease of illustration, C2-WT-Fc, C2-4B-Fc, C2-7A-Fc, C2-7B-Fc, C2-7BN78K-Fc in the above examples were selected for detection in the examples below.

The above obtained amino acid sequences were designed into corresponding encoding DNA sequences with the use of a DNAworks online tool (http://helixweb.nih.gov/dnaworks/); the obtained DNA sequences were fused with human IgG4-Fc genes and cloned into a commercialized vector pcDNA4 by double digestion with Hind III and EcoR I from Fermentas Co. The accuracy of the constructed plasmids was verified by sequencing to get recombinant plasmid DNA, i.e.: pcDNA4-C2-WT-Fc, pcDNA4-C2-4B-Fc, pcDNA4-C2-7A-Fc, pcDNA4-C2-7B-Fc and pcDNA4-C2-7BN78K-Fc. The plasmids were extracted according to the standard operations of molecular cloning. The extracted plasmids were transiently expressed in HEK 293 cells and purified through a Protein A column to get C2-WT-Fc, C2-4B-Fc, C2-7A-Fc, C2-7B-Fc, C2-7BN78K-Fc, which are used in the following examples. The obtained protein samples were detected primarily by SDS-PAGE so that the target bands may be observed clearly.

Example 2

Figure 2:
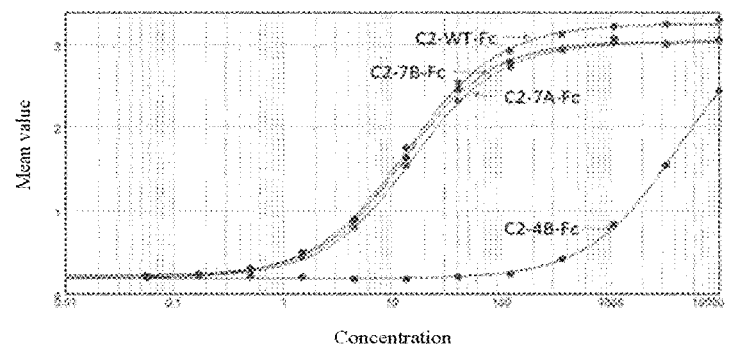
FIG. 2 shows the ELISA binding test results of the anti-CD137 antibody molecule of the present application.

Detection on the Binding Capacity of Anti-CD137 Antibody Molecule 2.1 Detection on the Binding Capacity with Anti-CD137 Protein (ELISA Method):

The CD137-muFc protein was diluted with a coating buffer (50 mM $Na_2CO_3$, $NaHCO_3$ pH 9.6) to 2 μg/ml, 100 μL per well, overnight at 4° C. After washing, the plates were blocked in 3% BSA-PBS at 37° C. for 1 hour. The anti-CD137 antibodies C2-WT-Fc, C2-4A-Fc, C2-7A-Fc and C2-7B-Fc were diluted 3-fold gradiently respectively starting from 10 μg/ml, totally 11 concentrations with the diluting solution (1% BSA-PBS) used as the control, and incubated at 37° C. for 2 hours. Goat anti-human IgG-HRP conjugated was added and incubated at 37° C. for 1 hour. A soluble single component TMB substrate chromogenic solution was added and developed in dark at room temperature for 5-10 minutes. 2N $H_2SO_4$ was added at 50 μL per well to terminate the chromogenic reaction. OD values at 450 nm-650 nm were read on a MD SpectraMax Plus384 microplate reader, and a software Soft Max pro v54 was applied for data treatment and diagraph analysis, with the results being shown in FIG. 2 and Table 2. The mean values shown in FIG. 2 may be obtained through the formula below:

$$\text{Mean value} = D + \frac{A - D}{1 + \left(\frac{x}{C}\right)^B}$$

TABLE 2

Detection on the binding capacities of anti-CD137 proteins

| Sample Name | $EC_{50}$ | $R^2$ | Parameters | Estimated value | Standard deviation | Confidence interval |
|---|---|---|---|---|---|---|
| C2-WT-Fc | 13.58 | 1.000 | A | 0.186 | 0.022 | [0.136, 0.235] |
| | | | B | 1.022 | 0.034 | [0.945, 1.100] |
| | | | C | 13.58 | 0.485 | [12.46, 14.70] |
| | | | D | 3.259 | 0.018 | [3.217, 3.301] |
| C2-7B-Fc | 13.16 | 0.999 | A | 0.218 | 0.023 | [0.165, 0.271] |
| | | | B | 1.096 | 0.044 | [0.995, 1.197] |
| | | | C | 13.16 | 0.535 | [11.93, 14.40] |
| | | | D | 3.046 | 0.019 | [3.001, 3.091] |
| C2-7A-Fc | 15.19 | 1.000 | A | 0.197 | 0.011 | [0.172, 0.222] |
| | | | B | 1.070 | 0.020 | [1.024, 1.116] |
| | | | C | 15.19 | 0.295 | [14.51, 15.87] |
| | | | D | 3.035 | 0.009 | [3.013, 3.056] |
| C2-4B-Fc | 4457 | 0.999 | A | 0.184 | 0.009 | [0.164, 0.205] |
| | | | B | 1.029 | 0.057 | [0.897, 1.161] |
| | | | C | 4457 | 590.1 | [3096, 5818] |
| | | | D | 3.425 | 0.191 | [2.985, 3.865] |

The results showed that, the antigen binding capacities of C2-7B-Fc, C2-7A-Fc and C2-WT-Fc were at the same level, the antigen binding capacity of C2-7B-Fc was slightly stronger than that of C2-7A-Fc, and the binding capacity of C2-4B-Fc was relatively weaker.

Figure 3:
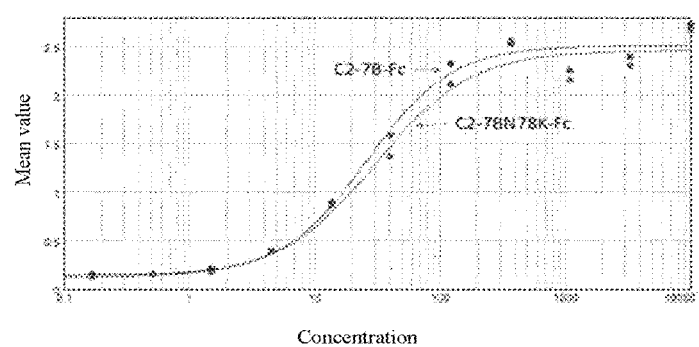
FIG. 3 shows the ELISA binding test results of the anti-CD137 antibody molecule of the present application.

Furthermore, C2-7B-Fc and C2-7BN78K were selected for comparison. The CD137 protein was diluted with a coating buffer (50 mM $Na_2CO_3$, $NaHCO_3$ pH 9.6) to 2 µg/ml, 100 mL per well, overnight at 4° C. After washing, the plates were blocked in 3% BSA-PBS at 37° C. for 1 hour. The anti-CD137 antibodies C2-7B-Fc and C2-7BN78K-Fc were diluted gradiently by 3 times respectively starting from 10 µg/ml, totally 11 concentrations with the diluting solution (1% BSA-PBS) used as the control, and incubated at 37° C. for 2 hours. Goat anti-human IgG-HRP conjugated was added and incubated at 37° C. for 1 hour. A soluble single component TMB substrate chromogenic solution was added and developed in dark at room temperature for 5-10 minutes. 2N $H_2SO_4$ was added at 50 µL per well to terminate the chromogenic reaction. OD values at 450 nm-650 nm were read on a MD SpectraMax Plus384 microplate reader, and a software Soft Max pro v54 was applied for data treatment and diagraph analysis, with the results being shown in FIG. 3 and Table 3. The mean values shown in FIG. 3 were also obtained through the above formula.

TABLE 3

Detection on the binding capacities of anti-CD137 proteins

| Sample Name | $EC_{50}$ | $R^2$ | Parameters | Estimated value | Standard deviation | Confidence interval |
|---|---|---|---|---|---|---|
| C2-7B-Fc | 26.20 | 0.989 | A | 0.145 | 0.072 | [−0.021, 0.311] |
| | | | B | 1.288 | 0.231 | [0.755, 1.822] |
| | | | C | 26.20 | 4.164 | [16.60, 35.80] |
| | | | D | 2.511 | 0.074 | [2.341, 2.682] |
| C2-7BN78K-Fc | 30.54 | 0.982 | A | 0.122 | 0.091 | [−0.087, 0.332] |
| | | | B | 1.138 | 0.251 | [0.559, 1.717] |
| | | | C | 30.54 | 6.663 | [15.17, 45.90] |
| | | | D | 2.461 | 0.098 | [2.234, 2.687] |

The results showed that, the antigen binding capacities of C2-7BN78K-Fc and C2-7B-Fc were comparable.

Figure 4:
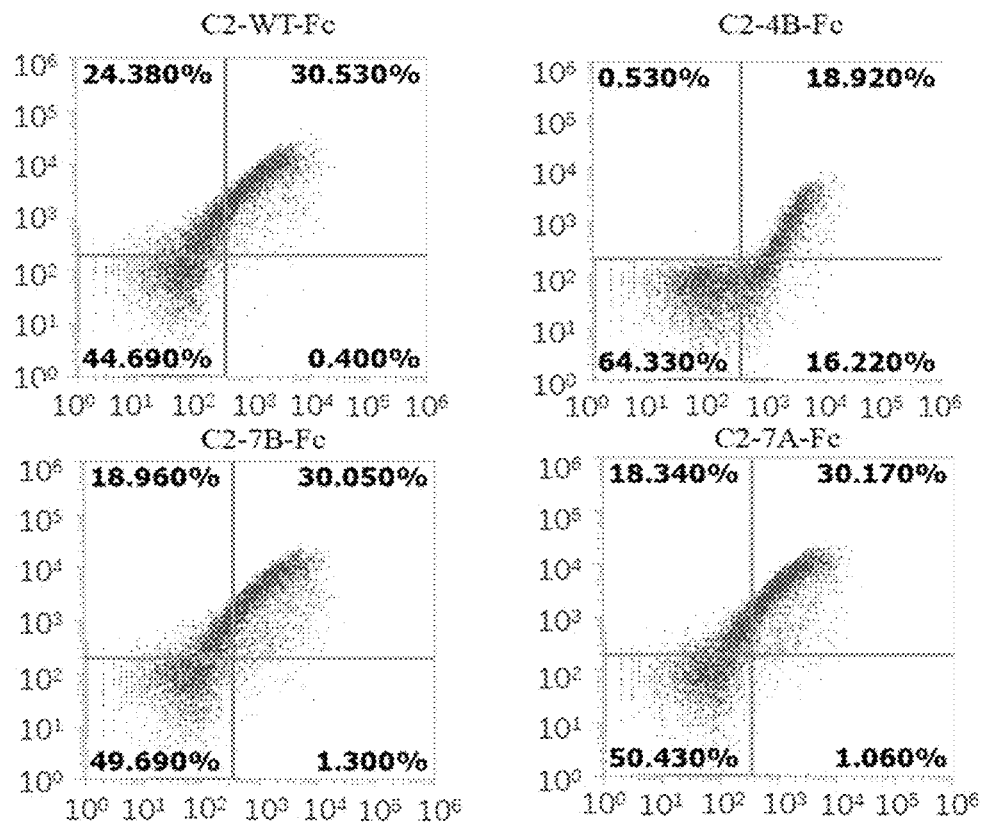
FIG. 4 shows the FACS binding test results of the anti-CD137 antibody molecule of the present application.

2.2 Detection on the Binding Capacity with CD137 Expressed on the Cell Surface (ELISA Method):

HEK 293 cells expressing hCD137-EGFP constructed in the examples were resuspended in a 0.5% PBS-BSA buffer, into which were added C2-WT-Fc, C2-4B-Fc, C2-7A-Fc and C2-7B-Fc proteins of anti-human CD137, with hIgG Fc protein as the negative control, and incubated on ice for 20 minutes. After washing, an eBioscience secondary antibody anti-hIg-PE was added and incubated on ice for 20 minutes. After washing, the cells were resuspended in 500 µL 0.5% PBS-BSA Buffer, and detected by a flow cytometry. The results were shown in FIG. 4, in which horizontal coordinates indicate the expression intensity of EGFP, and vertical coordinates indicate the intensity of a-hIg-PE.

The testing results of FACS method were consistent with those of ELISA method, in which the antigen binding capacities of C2-7B-Fc, C2-7A-Fc and C2-WT-Fc were at the same level, and the binding capacity of C2-4B-Fc was relatively weaker.

Example 3

Detection on the Agonist Activities of Anti-CD137 Antibody Molecules

Figure 5:
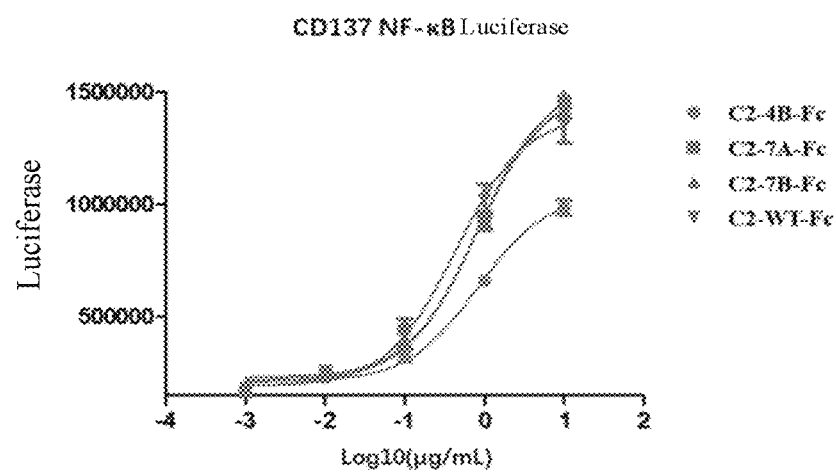
FIG. 5 shows the luciferase test results of the anti-CD137 antibody molecule of the present application.

293T-CD137-NF-kB stable cell lines from the laboratory were digested by adding pancreatin for 2-3 minutes, then DMEM complete medium was added to terminate the digestion. The cells were blown gently and the cell suspension was transferred and inoculated into a 96-well plate at 100 µL per well. The C2-WT-Fc, C2-4B-Fc, C2-7A-Fc and C2-7B-Fc antibodies were diluted 10-fold starting from 10 µg/ml. The diluted antibodies were mixed with anti-human crosslinking antibodies (Jackson ImmunoResearch Laboratories: 109-006-008) and added into a 96-well plate. Into the control group was added the complete medium, and 30 hours later, the lysed cells were detected by a luciferase assay system (Promega: E1501), with the results shown in FIG. 5 and Table 4.

TABLE 4

| | $EC_{50}$ values detected by luciferase | | | |
|---|---|---|---|---|
| | C2-4B-Fc | C2-7A-Fc | C2-7B-Fc | C2-WT-Fc |
| $EC_{50}$ (M) | 0.8196 | 0.8347 | 0.7821 | 0.4355 |

It may be seen from the results that, the agonist activity of C2-4B-Fc was lower, and the activities of C2-7A-Fc and C2-7B-Fc were close to that of C2-WT-Fc without mutations, which were all capable of activating downstream signaling.

Figure 6:
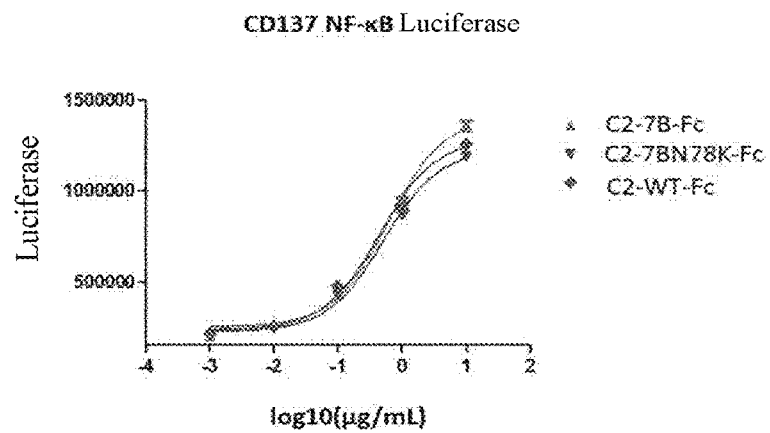
FIG. 6 shows the luciferase test results of the anti-CD137 antibody molecule of the present application.

In addition, 293T-CD137-NFκB stable cell lines from the laboratory were digested by adding pancreatin for 2-3 minutes, then DMEM complete medium was added to terminate the digestion. The cells were blown gently and the cell suspension was transferred and inoculated into a 96-well plate at 100 µL per well. The C2-WT-Fc, C2-7B-Fc and C2-7BN78K-Fc antibodies of scFv-Fc fusion protein forms were diluted 10-fold starting from 10 µg/ml. The diluted antibodies were mixed with anti-human crosslinking antibodies (Jackson ImmunoResearch Laboratories: 109-006-008) and added into a 96-well plate. Into the control group was added the complete medium, and 30 hours later, the lysed cells were detected by a luciferase assay system (Promega: E1501), with the results shown in FIG. 6 and Tables 5 and 6.

TABLE 5

| | $EC_{50}$ values detected by luciferase | | |
|---|---|---|---|
| | C2-7B-Fc | C2-7BN78K-Fc | C2-WT-Fc |
| $EC_{50}$ (M) | 0.6044 | 0.5110 | 0.4441 |

TABLE 6

Luciferase activities at different concentrations of anti-CD137 antibody molecules

| Concentration | Luciferase Activities | | | | | |
|---|---|---|---|---|---|---|
| (Hg/mL) | C2-7B-Fc | | C2-7BN78K-Fc | | C2-WT-Fc | |
| 10.000 | 1381994.000 | 1327616.000 | 1172492.000 | 1198311.000 | 1278156.000 | 1232526.000 |
| 1.000 | 891295.100 | 963131.300 | 873169.300 | 857256.400 | 958951.100 | 886658.300 |
| 0.100 | 481179.200 | 497724.400 | 418019.600 | 426485.400 | 477315.200 | 475312.900 |
| 0.010 | 270061.800 | 282391.600 | 244664.400 | 250144.300 | 269640.200 | 232826.400 |
| 0.001 | 198541.800 | 199209.200 | 199876.600 | 213471.000 | 216456.900 | 210344.700 |

The results showed that, the capabilities of C2-7BN78K-Fc, C2-7B-Fc and C2-WT-Fc in activating downstream signaling were comparable, and their agonist activities were also comparable.

Example 4

Anti-CD137 Antibodies Improve the Proliferation Ability of T Cells

Figure 7:
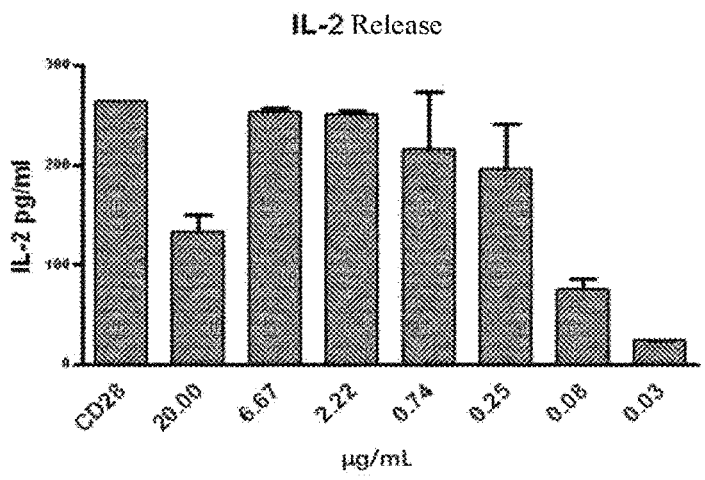
FIG. 7 shows the test results of the anti-CD137 antibody molecule promoting the release of cytokines IL-2 of T cells of the present application.

Peripheral blood mononuclear cells (PBMCs) were separated from leukocyte concentrate in the peripheral blood from healthy donors by means of density gradient centrifugation of human lymphocyte separation medium (Tianjin Haoyang), and inoculated into a RPMI complete medium. CD8 T cells were separated from PBMCs using a magnetic bead isolation kit (Miltenyi Biotec: 130-096-533) according to the instruction, counted and resuspended in the RPMI complete medium at a concentration of $2\times10^6$/mL. The isolated CD8$^+$ T cells were stimulated with 1 μg/mL of anti-CD3 and 0.2 μg/mL of anti-CD28 for activation. The C2-7B antibody was diluted 3-fold starting from 20 μg/ml, the diluted antibody was mixed with anti-human crosslinking antibody (Jackson Immuno Research Laboratories: 109-006-008) and added into the activated CD8$^+$ T cells, with the RPMI complete medium as the negative control. They were cultured for five days and the supernatants were collected. The level of IL-2 in the CD8$^+$ T cell supernatants was detected with a IL-2 ELISA Detection kit (ebioscience), with the results shown in FIG. 7. It may be seen from the results that, the anti-CD137 antibody C2-7B-Fc may improve the ability of CD8' T cells to secrete IL-2.

Example 5

Detection on the Stability of Anti-CD137 Antibodies 5.1 Purity Determination on Anti-CD137 Antibodies Through Accelerated Stabilization Experiment at 37° C.

Figure 8:
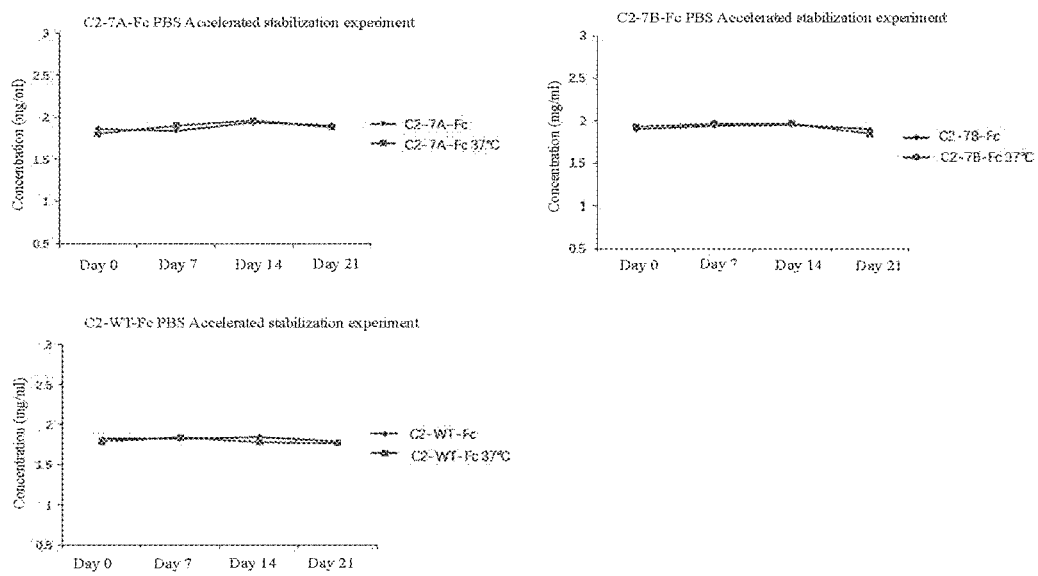
FIG. 8 shows the results of the accelerated stability experiment on the anti-CD137 antibody molecule of the present application.

An accelerated stabilization experiment at 37° C. was performed on the anti-CD137 antibodies, the specific experimental processes were as below: The anti-CD137 antibodies C2-WT-Fc, C2-7A-Fc and C2-7B-Fc which have been purified in one step through Protein A were dissolved in PBS (pH 7.4) and concentrated to 2 mg/mL. 100 μg of the antibodies were placed into a 200 μL PCR tube in a water bath at 37° C., and samples were collected on days 0, 7, 14 and 21 respectively and subjected to 280 detection and SEC-HPLC analysis, with the results shown in Table 7 and FIG. 8.

It may be seen from the results that, for the antibodies C2-WT-Fc, C2-7A-Fc and C2-7B-Fc, in terms of the concentrations of samples, the concentrations of samples collected at different time points had no significant changes; while in terms of the purities of samples, the protein purity of C2-WT-Fc decreased significantly over time, the protein purity of C2-7A-Fc decreased but not significantly, and the protein purity of C2-7B-Fc remained unchanged. It may be obviously seen from the results that, compared with C2-WT-Fc without stability mutations, the protein stabilities of C2-7A-Fc and C2-7B-Fc with stability mutations have been improved significantly.

TABLE 7

Accelerated stability detection at 37° C. on anti-CD137 antibodies

| Sample Name | Period in water bath at 37° C. (days) | Initial Purities (%) | Purities after water bath (%) |
|---|---|---|---|
| C2-WT-Fc | 0 | 94.6055 | 90.9139 |
|  | 7 |  | 79.1843 |
|  | 14 |  | 68.4941 |
|  | 21 |  | 60.1744 |
| C2-7A-Fc | 0 | 95.6959 | 97.1904 |
|  | 7 |  | 91.6468 |
|  | 14 |  | 91.6920 |
|  | 21 |  | 90.5082 |
| C2-7B-Fc | 0 | 95.0666 | 91.5778 |
|  | 7 |  | 93.2345 |
|  | 14 |  | 93.4088 |
|  | 21 |  | 92.6703 |

Figure 9A:
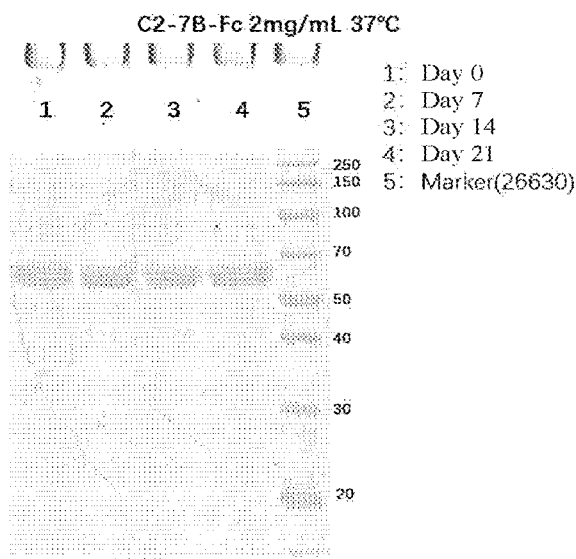
FIG. 9A-9B show the results of SDS-PAGE electrophoresis for testing the stability of the anti-CD137 antibody molecule at 37° C. of the present application.
Figure 9B:
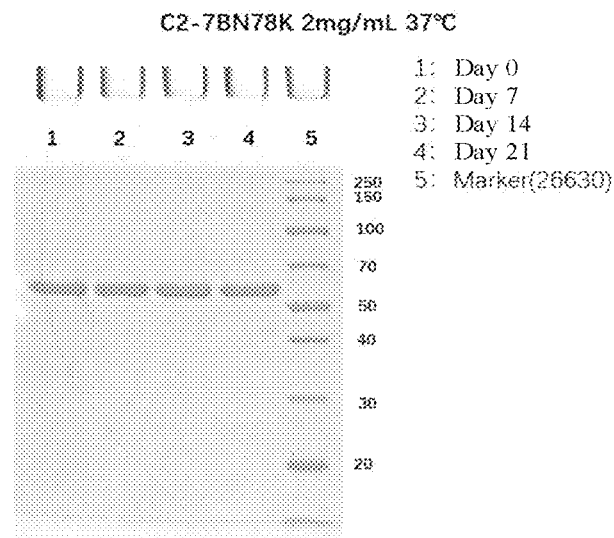
Figure 10A:
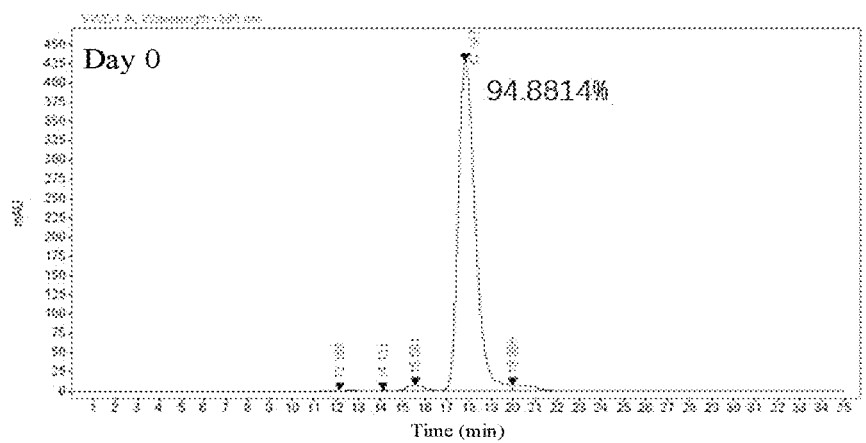
FIG. 10A-10D show the SEC-HPLC assay results of the anti-CD137 antibody molecule C2-7B-Fc of the present application.
Figure 10B:
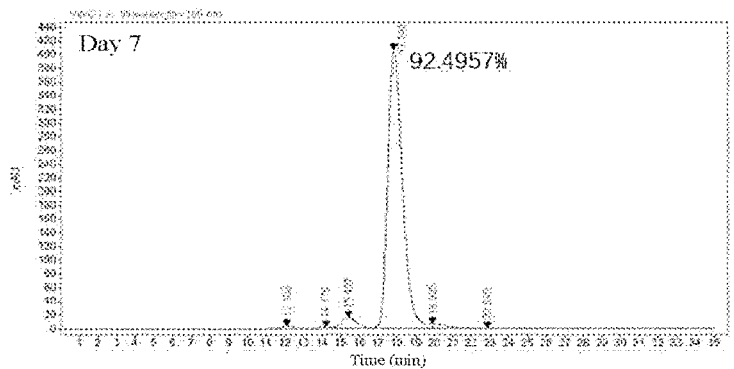
Figure 10C:
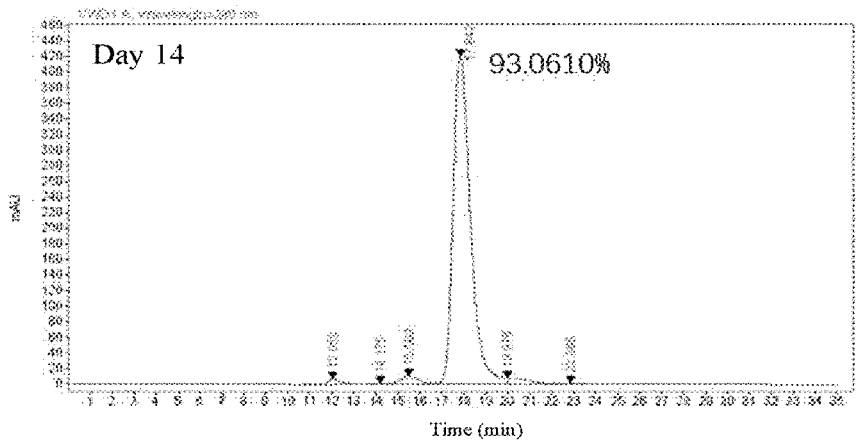
Figure 10D:
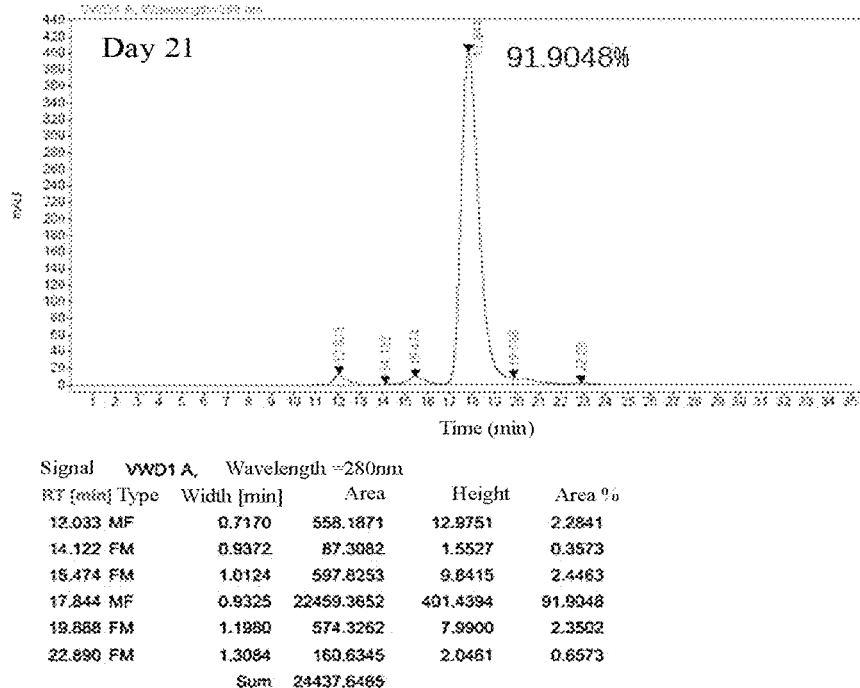
Figure 11A:
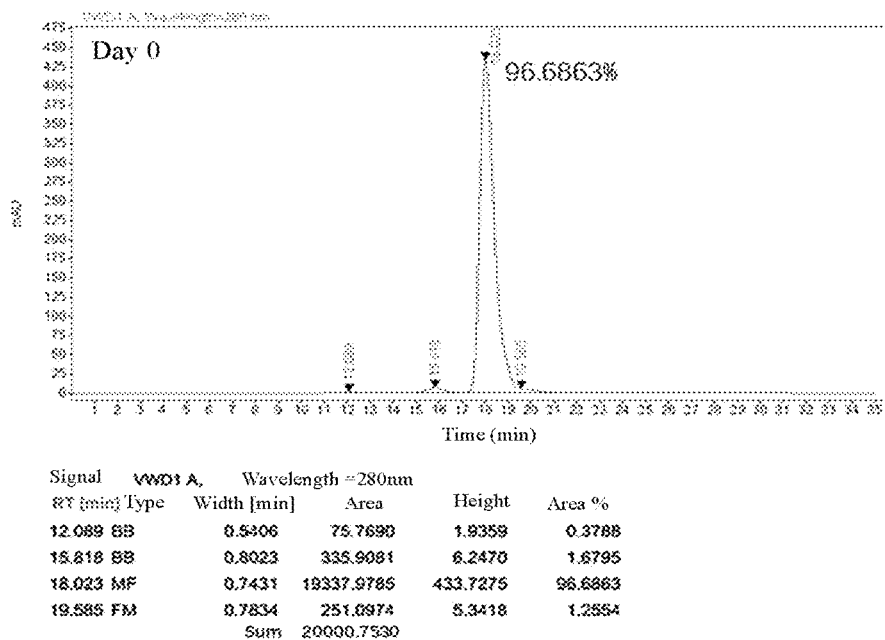
FIG. 11A-11D show the SEC-HPLC assay results of the anti-CD137 antibody molecule C2-7BN78K-Fc of the present application.
Figure 11B:
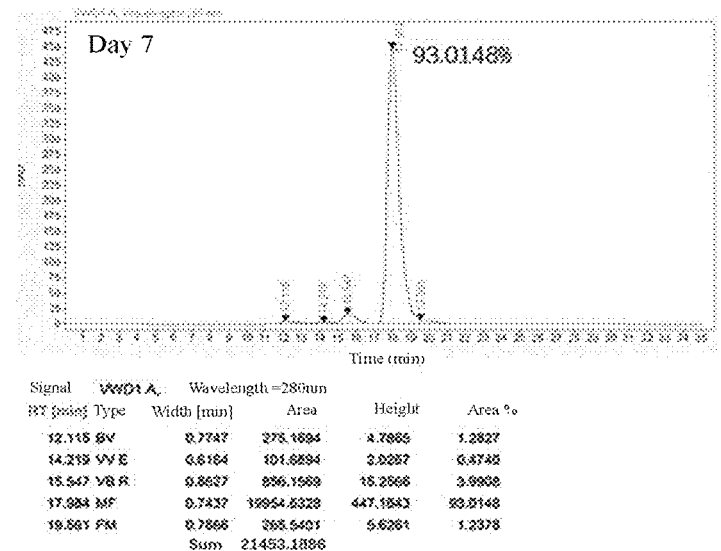
Figure 11C:
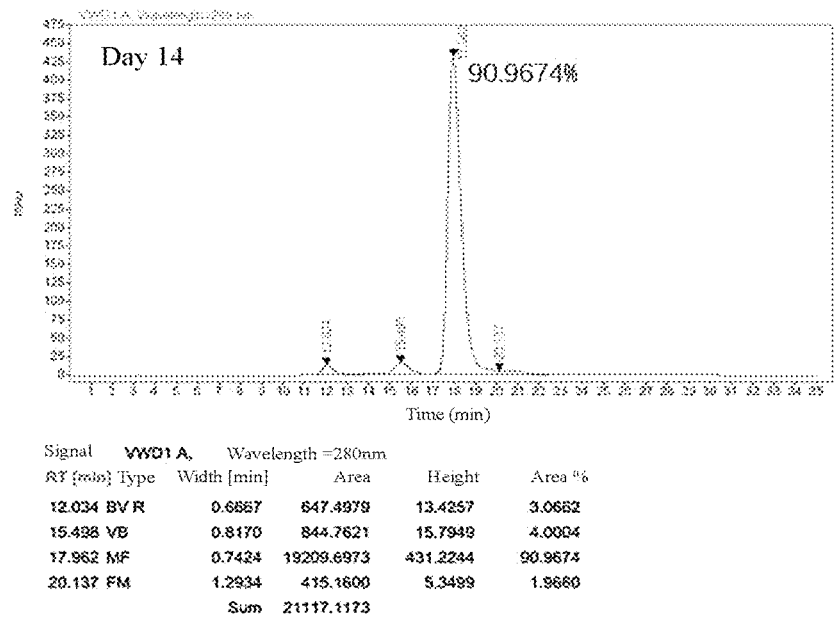
Figure 11D:
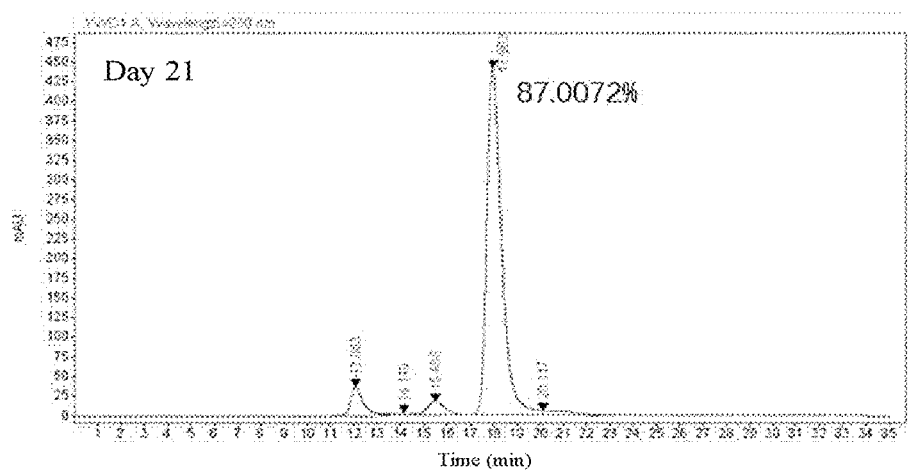

In addition, the sample C2-7B-Fc and C2-7BN78K-Fc proteins were concentrated to 2 mg/mL. They were sampled and the protein purities were detected. Then they were placed in a water bath at 37° C., sampled on days 0, 7, 14 and 21 respectively and subjected to SDS electrophoresis, with the detection results shown in FIGS. 9A and 9B. The purity analysis results of C2-7B-Fc and C2-7BN78K-Fc proteins were shown in FIGS. 10A-10D and FIGS. 11A-11D, respectively.

The results showed that, both C2-7B-Fc and C2-7BN78K-Fc had higher stability.

5.2 Detection on the Stability of Anti-CD137 Antibodies by Differential Scanning Calorimeter (DSC)

The thermal stability of anti-CD137 antibodies was detected by a process of DSC. To complete the test correctly by DSC, the scanning results of a separate buffer and a buffer comprising proteins were collected.

Figure 12:
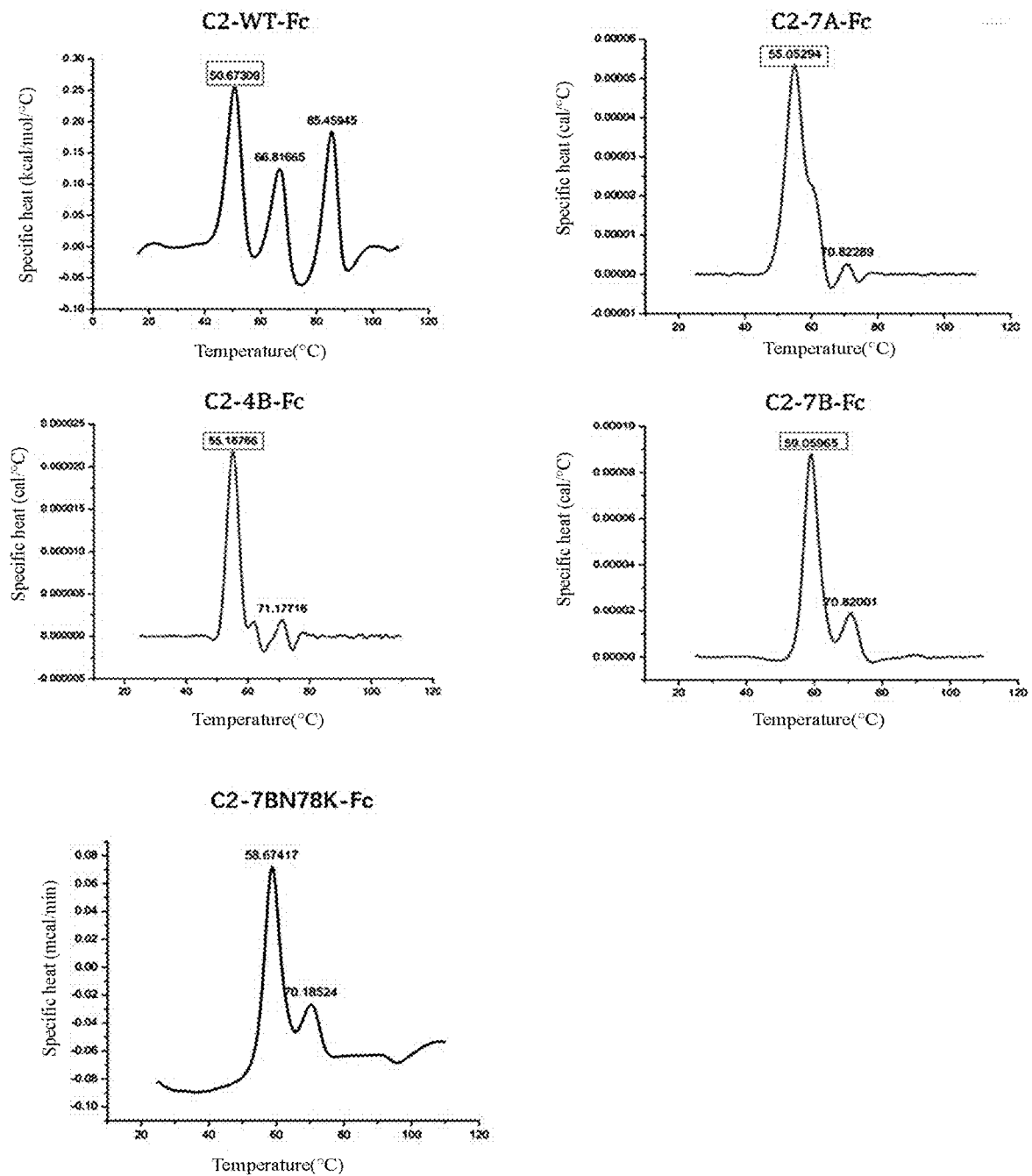
FIG. 12 shows the DSC thermal stability test results of the anti-CD137 antibody molecule of the present application.

The anti-CD137 antibody proteins were diluted to 1 mg/mL (PBS buffering solution). The data was collected according to the following conditions: DSC was set as scanning at 10-110° C., the scanning rate was 100° C./hour, and there was an equilibrium of 15 minutes before each scanning. The DSC sample chamber had a volume of 0.5 mL. After collecting the scanning results of the buffer and proteins, the scanning result of the buffer may be subtracted from that of proteins. The concentrations of protein samples were obtained to correct the concentrations in various scanning, thus obtaining the Tm values of anti-CD137 antibodies, with the results shown in FIG. 12. It may be seen from the results that, the Tm value of C2-7B-Fc was 59.05965° C., which is the highest in C2-WT-Fc C2-4B-Fc, C2-7A-Fc and C2-7B-Fc, hence C2-7B-Fc is the most stable.

In addition, the thermal stability of anti-CD137 antibodies was detected by a process of DSC. To complete the test correctly by DSC, the scanning results of a separate buffer and a buffer comprising proteins were collected.

The anti-CD137 antibody proteins were diluted to 1 mg/mL (PBS buffering solution). The data was collected according to the following conditions: DSC was set as scanning at 10-110° C., the scanning rate was 100° C./hour, and there was an equilibrium of 15 minutes before each scanning. The DSC sample chamber had a volume of 0.5 mL. After collecting the scanning results of the buffer and proteins, the scanning result of the buffer may be subtracted from that of proteins. The concentrations of protein samples were obtained to correct the concentrations in various scannings, thus obtaining the Tm values of anti-CD137 antibodies, with the results shown in FIG. 12. It may be seen from the results that, the transition midpoint value (Tm) of C2-7B-Fc is similar to that of C2-7BN78K-Fc, and they had similar thermal stability.

Example 6

Detection on the Pharmacokinetics of Anti-CD137 Antibodies in Rats

Figure 13:
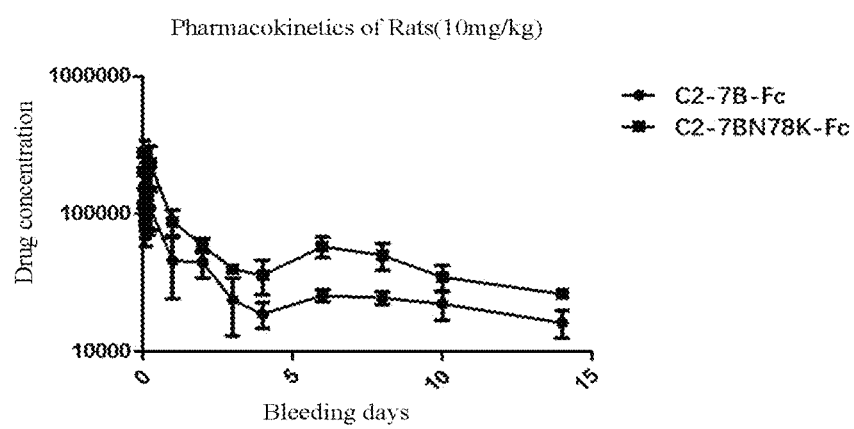
FIG. 13 shows the pharmacokinetic test results of the anti-CD137 antibody molecule of the present application.

Using SD, female rats at an age of 2-3 months, six rats were divided into two groups evenly, with three rats per group. All the rats were injected with 2.2 mg (10 mg/kg) C2-7B-Fc and C2-7BN78K-Fc proteins intravenously. After administration, 100 μl blood was sampled respectively at 13 time points. The concentrations of target proteins in sera were detected by ELISA process: hCD137-muFc was coated, into which was added serum samples of an appropriate dilution and then added Goat anti-Human IgG HRP (Sigma CatNO:A0170), and developed with TMB. A standard curve was plotted using C2-7B-Fc or C2-7BN78K-Fc protein as the standard protein in corresponding groups. Pharmacokinetic parameters were calculated with the use of a software WinNolin. The average C-T curve was set forth in FIG. 13 and Table 8. It was detected that the half life of C2-7B-Fc was 170.8 hours, C2-7BN78K-Fc is more stable, the half life in vivo of which was 173.52 hours on average, so both of them had comparable levels.

TABLE 8

Pharmacokinetic test of anti-CD137 antibodies

| Groups | Drug Name | Half life (h) | $CO_2$ (ng/ml) | AUC(0-t) (h*ng/ml) | AUC(0-inf) (h · ng/ml) | Vz_obs (ml/kg) | Cl_obs (ml/h/kg) | MRT (h) |
|---|---|---|---|---|---|---|---|---|
| 1 | C2-7B-Fc | 125.16 | 334681.34 | 9791512.60 | 11973771.00 | 150.80 | 0.84 | 126.02 |
| 2 | C2-7B-Fc | 219.33 | 295830.19 | 11290420.00 | 16758281.00 | 188.82 | 0.60 | 123.54 |
| 3 | C2-7B-Fc | 167.91 | 183159.55 | 8047911.60 | 12720952.00 | 190.43 | 0.79 | 134.92 |
| 4 | C2-7BN78K-Fc | 136.19 | 352765.18 | 18445374.00 | 23635924.00 | 83.13 | 0.42 | 128.80 |
| 5 | C2-7BN78K-Fc | 236.41 | 249434.85 | 17615969.00 | 26390155.00 | 129.24 | 0.38 | 120.77 |
| 6 | C2-7BN78K-Fc | 147.96 | 233357.13 | 16444026.00 | 22145195.00 | 96.39 | 0.45 | 130.06 |

Example 7

Inhibition of Anti-CD137 Antibodies on Tumors

Figure 14:
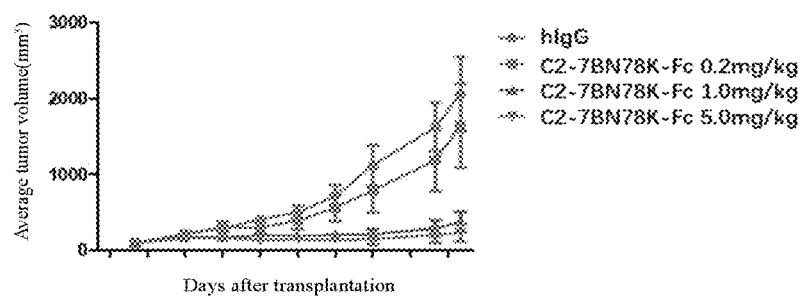
FIG. 14 shows the inhibition effects of the anti-CD137 antibody molecule on tumors of the present application.

Tumor models of MC38 and CD137 humanized mice (Biocytogen) in which the tumor cells had implanted were utilized to evaluate the pharmaceutical effects of complete anti-CD137 antibodies in vivo. The mice were divided into four groups, with ten mice per group. On day 0, CD137 humanized mice were inoculated with $1\times10^6$ MC38 cells subcutaneously. And on day 7, the mice were grouped and administrated at dosages of 0.2 mg/kg, 1 mg/kg and 5 mg/kg respectively twice a week, totally for 6 times. The formation of tumors was observed twice a week, and a vernier caliper was used to measure the long and short diameters of tumors, thereby calculating the tumor volumes and plotting the tumor growth curve, with the results shown in FIG. 14.

The results showed that, in mice which had been injected with C2-7BN78K-Fc, there was one mouse in the group of 0.2 mg/kg showing delayed tumor growth, and there were three mice in the group of 1 mg/kg and five mice in the group of 5 mg/kg showing the arrest of tumor growth. It may be seen from the results that, C2-7BN78K-Fc protein significantly inhibited the tumor growth.

The foregoing detailed description is provided by means of explanations and examples, but not intended to limit the scope of the attached claims. Various changes made to currently listed implementations herein are apparent to those with ordinary skills in the art, and are reserved within the scope of the attached claims and their equivalent schemes.

The invention claimed is:

1. An antibody specifically binding CD137 or an antigen binding fragment thereof, comprising a light chain variable region VL and a heavy chain variable region VH, wherein compared to a sequence as shown in SEQ ID NO: 103, the VL comprises one or more VL amino acid mutations, and the VL amino acid mutation occurs at one or more positions selected from a group consisting of: V3, A10, K44, D71 and V77;

wherein compared to a sequence as shown in SEQ ID NO: 127, the VH comprises one or more VH amino acid mutations, and the VH amino acid mutation occurs at one or more positions selected from a group consisting of: Q13, N78, H84, D86, A90 and F97.

2. The antibody or the antigen binding fragment thereof according to claim 1, wherein the VL amino acid mutation comprises VL amino acid mutations occurring at positions A10 and V77;

wherein the VH amino acid mutation comprises a VH amino acid mutation occurring at position Q13; and/or, wherein the VH amino acid mutation further comprises a VH amino acid mutation occurring at position N78.

3. The antibody or the antigen binding fragment thereof according to claim 1, wherein the VL amino acid mutation comprises VL amino acid mutations at positions of any one group below:
1) V3, D71 and V77;
2) A10 and V77;
3) D71;
4) A10, D71 and V77;
5) D71 and V77;
6) A10 and D71; or
7) V3, A10, K44, D71 and V77; and/or,
the VH amino acid mutation comprises VH amino acid mutations at positions of any one group below:
1) N78;
2) N78, H84, and D86;
3) Q13, N78, H84 and D86;
4) Q13 and N78;
5) Q13, H84, D86, A90 and F97; or
6) Q13, N78, H84, D86, A90 and F97.

4. The antibody or the antigen binding fragment thereof according to claim 1, wherein the VL amino acid mutation and the VH amino acid mutation comprise amino acid mutations at positions of any one of the following groups, respectively:
1) VL: V3, D71 and V77, and VH: N78;
2) VL: D71, and VH: N78, H84 and D86;
3) VL: D71 and V77, and VH: N78, H84 and D86;
4) VL: A10, D71 and V77, and VH: N78, H84 and D86;
5) VL: A10 and D71, and VH: Q13, N78, H84 and D86;
6) VL: V3, A10, K44, D71 and V77, and VH: Q13 and N78;
7) VL: A10 and V77, and VH: Q13, H84, D86, A90 and F97; or
8) VL: A10 and V77, and VH: Q13, N78, H84, D86, A90 and F97.

5. The antibody or the antigen binding fragment thereof according to claim 1, wherein the VL amino acid mutation at V3 is selected from: V3A, V3M, V3G;
wherein the VL amino acid mutation at A10 is selected from: A10V, A10L, A10I;
wherein the VL amino acid mutation at K44 is selected from: K44T, K44G;
wherein the VL amino acid mutation at D71 is selected from: D71N, D71Q;
wherein the VL amino acid mutation at V77 is selected from: V77I;
wherein the VH amino acid mutation at Q13 is selected from: Q13K, Q13R;
wherein the VH amino acid mutation at N78 is selected from: N78K, N78D, N78Q;
wherein the VH amino acid mutation at H84 is selected from: H84Q, H84E;
wherein the VH amino acid mutation at D86 is selected from: D86N, D86E;
wherein the VH amino acid mutation at A90 is selected from: A90T, A90S; and/or,
wherein the VH amino acid mutation at F97 is selected from: F97Y, F97W.

6. The antibody or the antigen binding fragment thereof according to claim 1, wherein the VL amino acid mutation comprises VL amino acid mutations of any one group below:
1) V3A, D71N and V77I;
2) A10V and V77I;
3) D71N;
4) A10V, D71N and V77I;
5) D71N and V77I;
6) A10V and D71N; or
7) V3A, A10V, K44T, D71N and V77I; and/or,
the VH amino acid mutation comprises VH amino acid mutations of any one group below:
1) N78K;
2) N78K, H84Q and D86N;
3) Q13K, N78K, H84Q and D86N;
4) Q13K and N78K;
5) Q13K, H84Q, D86N, A90T and F97Y; or
6) Q13K, N78K, H84Q, D86N, A90T and F97Y.

7. The antibody or the antigen binding fragment thereof according to claim 1, wherein the VL amino acid mutation and the VH amino acid mutation comprise amino acid mutations of any one group below, respectively:
1) VL: V3A, D71N and V77I, and VH: N78K;
2) VL: D71N, and VH: N78K, H84Q and D86N;

3) VL: D71N and V77I, and VH: N78K, H84Q and D86N;
4) VL: A10V, D71N and V77I, and VH: N78K, H84Q and D86N;
5) VL: A10V and D71N, and VH: Q13K, N78K, H84Q and D86N;
6) VL: V3A, A10V, K44T, D71N and V77I, and VH: Q13K and N78K;
7) VL: A10V and V77I, and VH: Q13K, H84Q, D86N, A90T and F97Y; or
8) VL: A10V and V77I, and VH: Q13K, N78K, H84Q, D86N, A90T and F97Y.

8. The antibody or the antigen binding fragment thereof according to claim 1, wherein the VL comprises an amino acid sequence as set forth in any one of SEQ ID NOs: 104, 106, 108 and 110-114; and/or, wherein the VH comprises an amino acid sequence as set forth in any one of SEQ ID NOs: 128, 130, 132 and 134-138.

9. The antibody or the antigen binding fragment thereof according to claim 1, wherein:
1) The VL comprises an amino acid sequence as set forth in SEQ ID NO: 104, and the VH comprises an amino acid sequence as set forth in SEQ ID NO: 128;
2) the VL comprises an amino acid sequence as set forth in SEQ ID NO: 106, and the VH comprises an amino acid sequence as set forth in SEQ ID NO: 130;
3) The VL comprises an amino acid sequence as set forth in SEQ ID NO: 108, and the VH comprises an amino acid sequence as set forth in SEQ ID NO: 132;
4) the VL comprises an amino acid sequence as set forth in SEQ ID NO: 110, and the VH comprises an amino acid sequence as set forth in SEQ ID NO: 134;
5) the VL comprises an amino acid sequence as set forth in SEQ ID NO: 111, and the VH comprises an amino acid sequence as set forth in SEQ ID NO: 135;
6) The VL comprises an amino acid sequence as set forth in SEQ ID NO: 112, and the VH comprises an amino acid sequence as set forth in SEQ ID NO: 136;
7) the VL comprises an amino acid sequence as set forth in SEQ ID NO: 113, and the VH comprises an amino acid sequence as set forth in SEQ ID NO: 137;
8) The VL comprises an amino acid sequence as set forth in SEQ ID NO: 114, and the VH comprises an amino acid sequence as set forth in SEQ ID NO: 138.

10. The antibody or the antigen binding fragment thereof according to claim 1, wherein the antigen binding fragment is selected from: Fab, Fab', F(ab)$_2$, F(ab')$_2$, Fv and scFv.

11. The antibody or the antigen binding fragment thereof according to claim 1, further comprising a Fc domain, and the Fc domain comprises an amino acid sequence of a constant region of an immunoglobulin selected from: IgG1, IgG2, IgG3 and IgG4.

12. The antibody or the antigen binding fragment thereof according to claim 11, wherein the Fc domain is located at a C-terminal of the antibody or the antigen binding fragment thereof, and the Fc domain comprises an amino acid sequence as set forth in SEQ ID NO: 163 or SEQ ID NO: 164.

13. The antibody or the antigen binding fragment thereof according to claim 11, which is a homodimer protein consisting of two polypeptide chains, wherein each of the polypeptide chain comprises the light chain variable region VL, the heavy chain variable region VH and the Fc domain, wherein the Fc domain is located at a C-terminal of the VL.

14. The antibody or the antigen binding fragment thereof according to claim 13, wherein the polypeptide chain comprises an amino acid sequence as set forth in any one of SEQ ID NOs: 152, 154, 156 and 158-162.

15. A multispecific antibody or an antigen binding fragment thereof, comprising a first binding domain specifically binding CD137 and a second binding domain specifically binding a second target other than CD137, wherein the first binding domain is the antibody or the antigen binding fragment thereof according to claim 1, and the second target is selected from a tumor associated antigen.

16. An immunoconjugate, comprising the antibody or the antigen binding fragment thereof according to claim 1.

17. An isolated nucleic acid molecule, encoding the antibody or the antigen binding fragment thereof according to claim 1, or the immunoconjugate according to claim 16.

18. A vector, comprising the nucleic acid molecule according to claim 17.

19. A pharmaceutical composition, comprising:
the antibody or fragment of claim 1,
an immunoconjugate comprising the antibody or fragment, or an immunoconjugate comprising the antibody or fragment,
an isolated nucleic acid molecule encoding the antibody or fragment, and/or a vector comprising the nucleic acid molecule; and
a pharmaceutically acceptable adjuvant.

20. A method of treating cancer, the method comprising:
administering an effective amount of the antibody or fragment of claim 1 to a subject in need thereof,
wherein the cancer is colorectal cancer.

* * * * *

SEQUENCE LISTING

<160> NUMBER OF SEQ ID NOS: 167

<210> SEQ ID NO 1
<211> LENGTH: 14
<212> TYPE: PRT
<213> ORGANISM: Artificial Sequence
<220> FEATURE:
<223> OTHER INFORMATION: C2-WT LCDR1

<400> SEQUENCE: 1

Thr Gly Ile Ser Ser Asp Val Gly Ala Tyr Asp Tyr Val Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: C2-WT LCDR2

<400> SEQUENCE: 2

Glu Val Ser Lys Arg Pro Ser
1               5

<210> SEQ ID NO 3
<211> LENGTH: 11
<212> TYPE: PRT
<213> ORGANISM: Artificial Sequence
<220> FEATURE:
<223> OTHER INFORMATION: C2-WT LCDR3

<400> SEQUENCE: 3

Ser Ser His Ala Gly Ser Asn Asn Phe Tyr Val
1               5                   10

<210> SEQ ID NO 4
<211> LENGTH: 5
<212> TYPE: PRT
<213> ORGANISM: Artificial Sequence
<220> FEATURE:
<223> OTHER INFORMATION: C2-WT HCDR1

<400> SEQUENCE: 4

Asp Tyr Tyr Met Asn
1               5

<210> SEQ ID NO 5
<211> LENGTH: 19
<212> TYPE: PRT
<213> ORGANISM: Artificial Sequence
<220> FEATURE:
<223> OTHER INFORMATION: C2-WT HCDR2

<400> SEQUENCE: 5

Tyr Ile Ser Ser Ser Ala Ser Gly Ser Thr Ile Tyr Tyr Ala Asp Ser
1               5                   10                  15

Val Lys Gly

<210> SEQ ID NO 6
<211> LENGTH: 13
<212> TYPE: PRT
<213> ORGANISM: Artificial Sequence
<220> FEATURE:
<223> OTHER INFORMATION: C2-WT HCDR3

<400> SEQUENCE: 6

Val Val Pro Ala Gly Ser Gly Trp Arg Trp Phe Asp Pro
1               5                   10

<210> SEQ ID NO 7
<211> LENGTH: 30
<212> TYPE: PRT
<213> ORGANISM: Artificial Sequence
<220> FEATURE:
<223> OTHER INFORMATION: C2-WT HFR1

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: C2-WT HFR2

<400> SEQUENCE: 8

Trp Ile Arg Gln Ala Pro Gly Lys Gly Leu Glu Trp Val Ser
1               5                   10

<210> SEQ ID NO 9
<211> LENGTH: 32
<212> TYPE: PRT
<213> ORGANISM: Artificial Sequence
<220> FEATURE:
<223> OTHER INFORMATION: C2-WT HFR3

<400> SEQUENCE: 9

Arg Phe Thr Ile Ser Arg Asp Asn Ala Asn Asn Ser Leu Tyr Leu His
1               5                   10                  15

Met Asp Ser Leu Arg Ala Glu Asp Thr Ala Ile Tyr Phe Cys Ala Arg
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: C2-WT HFR4

<400> SEQUENCE: 10

Trp Gly Gln Gly Thr Leu Val Thr Val Ser Ser
1               5                   10

<210> SEQ ID NO 11
<211> LENGTH: 22
<212> TYPE: PRT
<213> ORGANISM: Artificial Sequence
<220> FEATURE:
<223> OTHER INFORMATION: C2-WT LFR1

<400> SEQUENCE: 11

Gln Ser Val Leu Ile Gln Pro Pro Ser Ala Ser Gly Ser Pro Gly Gln
1               5                   10                  15

Ser Val Thr Ile Ser Cys
            20

<210> SEQ ID NO 12
<211> LENGTH: 15
<212> TYPE: PRT
<213> ORGANISM: Artificial Sequence
<220> FEATURE:
<223> OTHER INFORMATION: C2-WT LFR2

<400> SEQUENCE: 12

```
<210> SEQ ID NO 13
<211> LENGTH: 32
<212> TYPE: PRT
<213> ORGANISM: Artificial Sequence
<220> FEATURE:
<223> OTHER INFORMATION: C2-WT LFR3

<400> SEQUENCE: 13

Gly Val Pro Asp Arg Phe Ser Gly Ser Lys Ser Gly Asp Thr Ala Ser
1               5                   10                  15

Leu Thr Val Ser Gly Leu Gln Ala Glu Asp Glu Ala Asp Tyr Tyr Cys
            20                  25                  30

<210> SEQ ID NO 14
<211> LENGTH: 10
<212> TYPE: PRT
<213> ORGANISM: Artificial Sequence
<220> FEATURE:
<223> OTHER INFORMATION: C2-WT LFR4

<400> SEQUENCE: 14

Phe Gly Thr Gly Thr Lys Leu Thr Val Leu
1               5                   10

<210> SEQ ID NO 15
<211> LENGTH: 30
<212> TYPE: PRT
<213> ORGANISM: Artificial Sequence
<220> FEATURE:
<223> OTHER INFORMATION: C2-4A HFR1

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 16
<211> LENGTH: 14
<212> TYPE: PRT
<213> ORGANISM: Artificial Sequence
<220> FEATURE:
<223> OTHER INFORMATION: C2-4A HFR2

<400> SEQUENCE: 16

Trp Ile Arg Gln Ala Pro Gly Lys Gly Leu Glu Trp Val Ser
1               5                   10

<210> SEQ ID NO 17
<211> LENGTH: 32
<212> TYPE: PRT
<213> ORGANISM: Artificial Sequence
<220> FEATURE:
<223> OTHER INFORMATION: C2-4A HFR3

<400> SEQUENCE: 17

Arg Phe Thr Ile Ser Arg Asp Asn Ala Lys Asn Ser Leu Tyr Leu His
1               5                   10                  15

Met Asp Ser Leu Arg Ala Glu Asp Thr Ala Ile Tyr Phe Cys Ala Arg
            20                  25                  30

<210> SEQ ID NO 18
<211> LENGTH: 11
<212> TYPE: PRT
<213> ORGANISM: Artificial Sequence
<220> FEATURE:
```

```
<223> OTHER INFORMATION: C2-4A HFR4

<400> SEQUENCE: 18

Trp Gly Gln Gly Thr Leu Val Thr Val Ser Ser
1               5                   10

<210> SEQ ID NO 19
<211> LENGTH: 22
<212> TYPE: PRT
<213> ORGANISM: Artificial Sequence
<220> FEATURE:
<223> OTHER INFORMATION: C2-4A LFR1

<400> SEQUENCE: 19

Gln Ser Ala Leu Ile Gln Pro Pro Ser Ala Ser Gly Ser Pro Gly Gln
1               5                   10                  15

Ser Val Thr Ile Ser Cys
            20

<210> SEQ ID NO 20
<211> LENGTH: 15
<212> TYPE: PRT
<213> ORGANISM: Artificial Sequence
<220> FEATURE:
<223> OTHER INFORMATION: C2-4A LFR2

<400> SEQUENCE: 20

Trp Tyr Gln Gln His Pro Gly Lys Val Pro Lys Leu Met Ile Tyr
1               5                   10                  15

<210> SEQ ID NO 21
<211> LENGTH: 32
<212> TYPE: PRT
<213> ORGANISM: Artificial Sequence
<220> FEATURE:
<223> OTHER INFORMATION: C2-4A LFR3

<400> SEQUENCE: 21

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 22
<211> LENGTH: 10
<212> TYPE: PRT
<213> ORGANISM: Artificial Sequence
<220> FEATURE:
<223> OTHER INFORMATION: C2-4A LFR4

<400> SEQUENCE: 22

Phe Gly Thr Gly Thr Lys Leu Thr Val Leu
1               5                   10

<210> SEQ ID NO 23
<211> LENGTH: 30
<212> TYPE: PRT
<213> ORGANISM: Artificial Sequence
<220> FEATURE:
<223> OTHER INFORMATION: C2-4B HFR1

<400> SEQUENCE: 23

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser
```

20                  25                  30

<210> SEQ ID NO 24
<211> LENGTH: 14
<212> TYPE: PRT
<213> ORGANISM: Artificial Sequence
<220> FEATURE:
<223> OTHER INFORMATION: C2-4B HFR2

<400> SEQUENCE: 24

Trp Phe Arg Gln Ala Pro Gly Lys Gly Leu Glu Trp Val Ser
1               5                   10

<210> SEQ ID NO 25
<211> LENGTH: 32
<212> TYPE: PRT
<213> ORGANISM: Artificial Sequence
<220> FEATURE:
<223> OTHER INFORMATION: C2-4B HFR3

<400> SEQUENCE: 25

Arg Phe Thr Ile Ser Arg Asp Asn Ala Lys Asn Ser Leu Tyr Leu His
1               5                   10                  15

Met Asp Ser Leu Arg Ala Glu Asp Thr Ala Ile Tyr Phe Cys Ala Arg
            20                  25                  30

<210> SEQ ID NO 26
<211> LENGTH: 11
<212> TYPE: PRT
<213> ORGANISM: Artificial Sequence
<220> FEATURE:
<223> OTHER INFORMATION: C2-4B HFR4

<400> SEQUENCE: 26

Trp Gly Gln Gly Thr Leu Val Thr Val Ser Ser
1               5                   10

<210> SEQ ID NO 27
<211> LENGTH: 22
<212> TYPE: PRT
<213> ORGANISM: Artificial Sequence
<220> FEATURE:
<223> OTHER INFORMATION: C2-4B LFR1

<400> SEQUENCE: 27

Gln Ser Val Leu Ile Gln Pro Pro Ser Val Ser Gly Ser Pro Gly Gln
1               5                   10                  15

Ser Val Thr Ile Ser Cys
            20

<210> SEQ ID NO 28
<211> LENGTH: 15
<212> TYPE: PRT
<213> ORGANISM: Artificial Sequence
<220> FEATURE:
<223> OTHER INFORMATION: C2-4B LFR2

<400> SEQUENCE: 28

Trp Tyr Gln Gln His Pro Gly Lys Val Pro Lys Leu Met Ile Tyr
1               5                   10                  15

<210> SEQ ID NO 29
<211> LENGTH: 32
<212> TYPE: PRT
<213> ORGANISM: Artificial Sequence
<220> FEATURE:

```
<223> OTHER INFORMATION: C2-4B LFR3

<400> SEQUENCE: 29

Gly Val Pro Asp Arg Phe Ser Gly Ser Lys Ser Gly Asp Thr Ala Ser
1               5                   10                  15

Leu Thr Ile Ser Gly Leu Gln Ala Glu Asp Glu Ala Tyr Tyr Cys
            20                  25                  30

<210> SEQ ID NO 30
<211> LENGTH: 10
<212> TYPE: PRT
<213> ORGANISM: Artificial Sequence
<220> FEATURE:
<223> OTHER INFORMATION: C2-4B LFR4

<400> SEQUENCE: 30

Phe Gly Thr Gly Thr Lys Leu Thr Val Leu
1               5                   10

<210> SEQ ID NO 31
<211> LENGTH: 30
<212> TYPE: PRT
<213> ORGANISM: Artificial Sequence
<220> FEATURE:
<223> OTHER INFORMATION: C2-4C HFR1

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 32
<211> LENGTH: 14
<212> TYPE: PRT
<213> ORGANISM: Artificial Sequence
<220> FEATURE:
<223> OTHER INFORMATION: C2-4C HFR2

<400> SEQUENCE: 32

Trp Ile Arg Gln Ala Pro Gly Lys Gly Leu Glu Trp Val Ser
1               5                   10

<210> SEQ ID NO 33
<211> LENGTH: 32
<212> TYPE: PRT
<213> ORGANISM: Artificial Sequence
<220> FEATURE:
<223> OTHER INFORMATION: C2-4C HFR3

<400> SEQUENCE: 33

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Ile Tyr Phe Cys Ala Arg
            20                  25                  30

<210> SEQ ID NO 34
<211> LENGTH: 11
<212> TYPE: PRT
<213> ORGANISM: Artificial Sequence
<220> FEATURE:
<223> OTHER INFORMATION: C2-4C HFR4

<400> SEQUENCE: 34

Trp Gly Gln Gly Thr Leu Val Thr Val Ser Ser
```

```
<210> SEQ ID NO 35
<211> LENGTH: 22
<212> TYPE: PRT
<213> ORGANISM: Artificial Sequence
<220> FEATURE:
<223> OTHER INFORMATION: C2-4C LFR1

<400> SEQUENCE: 35

Gln Ser Val Leu Ile Gln Pro Pro Ser Ala Ser Gly Ser Pro Gly Gln
1               5                   10                  15

Ser Val Thr Ile Ser Cys
            20

<210> SEQ ID NO 36
<211> LENGTH: 15
<212> TYPE: PRT
<213> ORGANISM: Artificial Sequence
<220> FEATURE:
<223> OTHER INFORMATION: C2-4C LFR2

<400> SEQUENCE: 36

Trp Tyr Gln Gln His Pro Gly Lys Val Pro Lys Leu Met Ile Tyr
1               5                   10                  15

<210> SEQ ID NO 37
<211> LENGTH: 32
<212> TYPE: PRT
<213> ORGANISM: Artificial Sequence
<220> FEATURE:
<223> OTHER INFORMATION: C2-4C LFR3

<400> SEQUENCE: 37

Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Tyr Cys
            20                  25                  30

<210> SEQ ID NO 38
<211> LENGTH: 10
<212> TYPE: PRT
<213> ORGANISM: Artificial Sequence
<220> FEATURE:
<223> OTHER INFORMATION: C2-4C LFR4

<400> SEQUENCE: 38

Phe Gly Thr Gly Thr Lys Leu Thr Val Leu
1               5                   10

<210> SEQ ID NO 39
<211> LENGTH: 30
<212> TYPE: PRT
<213> ORGANISM: Artificial Sequence
<220> FEATURE:
<223> OTHER INFORMATION: C2-5A HFR1

<400> SEQUENCE: 39

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser
            20                  25                  30

<210> SEQ ID NO 40
<211> LENGTH: 14
```

-continued

```
<212> TYPE: PRT
<213> ORGANISM: Artificial Sequence
<220> FEATURE:
<223> OTHER INFORMATION: C2-5A HFR2

<400> SEQUENCE: 40

Trp Ile Arg Gln Ala Pro Gly Lys Gly Leu Glu Trp Val Ser
1               5                   10

<210> SEQ ID NO 41
<211> LENGTH: 32
<212> TYPE: PRT
<213> ORGANISM: Artificial Sequence
<220> FEATURE:
<223> OTHER INFORMATION: C2-5A HFR3

<400> SEQUENCE: 41

Arg Phe Thr Ile Ser Arg Asp Asn Ala Lys Asn Ser Leu Tyr Leu His
1               5                   10                  15

Met Asp Ser Leu Arg Ala Glu Asp Thr Ala Ile Tyr Phe Cys Ala Arg
                20                  25                  30

<210> SEQ ID NO 42
<211> LENGTH: 11
<212> TYPE: PRT
<213> ORGANISM: Artificial Sequence
<220> FEATURE:
<223> OTHER INFORMATION: C2-5A HFR4

<400> SEQUENCE: 42

Trp Gly Gln Gly Thr Leu Val Thr Val Ser Ser
1               5                   10

<210> SEQ ID NO 43
<211> LENGTH: 22
<212> TYPE: PRT
<213> ORGANISM: Artificial Sequence
<220> FEATURE:
<223> OTHER INFORMATION: C2-5A LFR1

<400> SEQUENCE: 43

Gln Ser Val Leu Ile Gln Pro Pro Ser Val Ser Gly Ser Pro Gly Gln
1               5                   10                  15

Ser Val Thr Ile Ser Cys
                20

<210> SEQ ID NO 44
<211> LENGTH: 15
<212> TYPE: PRT
<213> ORGANISM: Artificial Sequence
<220> FEATURE:
<223> OTHER INFORMATION: C2-5A LFR2

<400> SEQUENCE: 44

Trp Tyr Gln Gln His Pro Gly Lys Val Pro Lys Leu Met Ile Tyr
1               5                   10                  15

<210> SEQ ID NO 45
<211> LENGTH: 32
<212> TYPE: PRT
<213> ORGANISM: Artificial Sequence
<220> FEATURE:
<223> OTHER INFORMATION: C2-5A LFR3

<400> SEQUENCE: 45

Gly Val Pro Asp Arg Phe Ser Gly Ser Lys Ser Gly Asn Thr Ala Ser
```

```
1               5                   10                  15
Leu Thr Ile Ser Gly Leu Gln Ala Glu Asp Glu Ala Asp Tyr Tyr Cys
            20                  25                  30

<210> SEQ ID NO 46
<211> LENGTH: 10
<212> TYPE: PRT
<213> ORGANISM: Artificial Sequence
<220> FEATURE:
<223> OTHER INFORMATION: C2-5A LFR4

<400> SEQUENCE: 46

Phe Gly Thr Gly Thr Lys Leu Thr Val Leu
1               5                   10

<210> SEQ ID NO 47
<211> LENGTH: 30
<212> TYPE: PRT
<213> ORGANISM: Artificial Sequence
<220> FEATURE:
<223> OTHER INFORMATION: C2-5B HFR1

<400> SEQUENCE: 47

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Ser
            20                  25                  30

<210> SEQ ID NO 48
<211> LENGTH: 14
<212> TYPE: PRT
<213> ORGANISM: Artificial Sequence
<220> FEATURE:
<223> OTHER INFORMATION: C2-5B HFR2

<400> SEQUENCE: 48

Trp Ile Arg Gln Ala Pro Gly Lys Gly Leu Glu Trp Val Ser
1               5                   10

<210> SEQ ID NO 49
<211> LENGTH: 32
<212> TYPE: PRT
<213> ORGANISM: Artificial Sequence
<220> FEATURE:
<223> OTHER INFORMATION: C2-5B HFR3

<400> SEQUENCE: 49

Arg Phe Thr Ile Ser Arg Asp Asn Ala Lys Asn Ser Leu Tyr Leu Gln
1               5                   10                  15
Met Asn Ser Leu Arg Ala Glu Asp Thr Ala Ile Tyr Phe Cys Ala Arg
            20                  25                  30

<210> SEQ ID NO 50
<211> LENGTH: 11
<212> TYPE: PRT
<213> ORGANISM: Artificial Sequence
<220> FEATURE:
<223> OTHER INFORMATION: C2-5B HFR4

<400> SEQUENCE: 50

Trp Gly Gln Gly Thr Leu Val Thr Val Ser Ser
1               5                   10

<210> SEQ ID NO 51
<211> LENGTH: 22
```

<212> TYPE: PRT
<213> ORGANISM: Artificial Sequence
<220> FEATURE:
<223> OTHER INFORMATION: C2-5B LFR1

<400> SEQUENCE: 51

Gln Ser Val Leu Ile Gln Pro Pro Ser Ala Ser Gly Ser Pro Gly Gln
1               5                   10                  15

Ser Val Thr Ile Ser Cys
            20

<210> SEQ ID NO 52
<211> LENGTH: 15
<212> TYPE: PRT
<213> ORGANISM: Artificial Sequence
<220> FEATURE:
<223> OTHER INFORMATION: C2-5B LFR2

<400> SEQUENCE: 52

Trp Tyr Gln Gln His Pro Gly Lys Val Pro Lys Leu Met Ile Tyr
1               5                   10                  15

<210> SEQ ID NO 53
<211> LENGTH: 32
<212> TYPE: PRT
<213> ORGANISM: Artificial Sequence
<220> FEATURE:
<223> OTHER INFORMATION: C2-5B LFR3

<400> SEQUENCE: 53

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 54
<211> LENGTH: 10
<212> TYPE: PRT
<213> ORGANISM: Artificial Sequence
<220> FEATURE:
<223> OTHER INFORMATION: C2-5B LFR4

<400> SEQUENCE: 54

Phe Gly Thr Gly Thr Lys Leu Thr Val Leu
1               5                   10

<210> SEQ ID NO 55
<211> LENGTH: 30
<212> TYPE: PRT
<213> ORGANISM: Artificial Sequence
<220> FEATURE:
<223> OTHER INFORMATION: C2-5C HFR1

<400> SEQUENCE: 55

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser
            20                  25                  30

<210> SEQ ID NO 56
<211> LENGTH: 14
<212> TYPE: PRT
<213> ORGANISM: Artificial Sequence
<220> FEATURE:
<223> OTHER INFORMATION: C2-5C HFR2

<400> SEQUENCE: 56

Trp Phe Arg Gln Ala Pro Gly Lys Gly Leu Glu Trp Val Ser
1               5                   10

<210> SEQ ID NO 57
<211> LENGTH: 32
<212> TYPE: PRT
<213> ORGANISM: Artificial Sequence
<220> FEATURE:
<223> OTHER INFORMATION: C2-5C HFR3

<400> SEQUENCE: 57

Arg Phe Thr Ile Ser Arg Asp Asn Ala Asn Asn Ser Leu Tyr Leu His
1               5                   10                  15

Met Asp Ser Leu Arg Ala Glu Asp Thr Ala Ile Tyr Tyr Cys Ala Arg
            20                  25                  30

<210> SEQ ID NO 58
<211> LENGTH: 11
<212> TYPE: PRT
<213> ORGANISM: Artificial Sequence
<220> FEATURE:
<223> OTHER INFORMATION: C2-5C HFR4

<400> SEQUENCE: 58

Trp Gly Gln Gly Thr Leu Val Thr Val Ser Ser
1               5                   10

<210> SEQ ID NO 59
<211> LENGTH: 22
<212> TYPE: PRT
<213> ORGANISM: Artificial Sequence
<220> FEATURE:
<223> OTHER INFORMATION: C2-5C LFR1

<400> SEQUENCE: 59

Gln Ser Val Leu Ile Gln Pro Pro Ser Val Ser Gly Ser Pro Gly Gln
1               5                   10                  15

Ser Val Thr Ile Ser Cys
            20

<210> SEQ ID NO 60
<211> LENGTH: 15
<212> TYPE: PRT
<213> ORGANISM: Artificial Sequence
<220> FEATURE:
<223> OTHER INFORMATION: C2-5C LFR2

<400> SEQUENCE: 60

Trp Tyr Gln Gln His Pro Gly Lys Val Pro Lys Leu Met Ile Tyr
1               5                   10                  15

<210> SEQ ID NO 61
<211> LENGTH: 32
<212> TYPE: PRT

```
<213> ORGANISM: Artificial Sequence
<220> FEATURE:
<223> OTHER INFORMATION: C2-5C LFR3

<400> SEQUENCE: 61

Gly Val Pro Asp Arg Phe Ser Gly Ser Lys Ser Gly Asp Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 62
<211> LENGTH: 10
<212> TYPE: PRT
<213> ORGANISM: Artificial Sequence
<220> FEATURE:
<223> OTHER INFORMATION: C2-5C LFR4

<400> SEQUENCE: 62

Phe Gly Thr Gly Thr Lys Leu Thr Val Leu
1               5                   10

<210> SEQ ID NO 63
<211> LENGTH: 30
<212> TYPE: PRT
<213> ORGANISM: Artificial Sequence
<220> FEATURE:
<223> OTHER INFORMATION: C2-6A HFR1

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 64
<211> LENGTH: 14
<212> TYPE: PRT
<213> ORGANISM: Artificial Sequence
<220> FEATURE:
<223> OTHER INFORMATION: C2-6A HFR2

<400> SEQUENCE: 64

Trp Ile Arg Gln Ala Pro Gly Lys Gly Leu Glu Trp Val Ser
1               5                   10

<210> SEQ ID NO 65
<211> LENGTH: 32
<212> TYPE: PRT
<213> ORGANISM: Artificial Sequence
<220> FEATURE:
<223> OTHER INFORMATION: C2-6A HFR3

<400> SEQUENCE: 65

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Ile Tyr Phe Cys Ala Arg
            20                  25                  30

<210> SEQ ID NO 66
<211> LENGTH: 11
<212> TYPE: PRT
<213> ORGANISM: Artificial Sequence
<220> FEATURE:
<223> OTHER INFORMATION: C2-6A HFR4

<400> SEQUENCE: 66
```

```
Trp Gly Gln Gly Thr Leu Val Thr Val Ser Ser
1               5                   10

<210> SEQ ID NO 67
<211> LENGTH: 22
<212> TYPE: PRT
<213> ORGANISM: Artificial Sequence
<220> FEATURE:
<223> OTHER INFORMATION: C2-6A LFR1

<400> SEQUENCE: 67

Gln Ser Val Leu Ile Gln Pro Pro Ser Val Gly Ser Pro Gly Gln
1               5                   10                  15

Ser Val Thr Ile Ser Cys
                20

<210> SEQ ID NO 68
<211> LENGTH: 15
<212> TYPE: PRT
<213> ORGANISM: Artificial Sequence
<220> FEATURE:
<223> OTHER INFORMATION: C2-6A LFR2

<400> SEQUENCE: 68

Trp Tyr Gln Gln His Pro Gly Lys Val Pro Lys Leu Met Ile Tyr
1               5                   10                  15

<210> SEQ ID NO 69
<211> LENGTH: 32
<212> TYPE: PRT
<213> ORGANISM: Artificial Sequence
<220> FEATURE:
<223> OTHER INFORMATION: C2-6A LFR3

<400> SEQUENCE: 69

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
                20                  25                  30

<210> SEQ ID NO 70
<211> LENGTH: 10
<212> TYPE: PRT
<213> ORGANISM: Artificial Sequence
<220> FEATURE:
<223> OTHER INFORMATION: C2-6A LFR4

<400> SEQUENCE: 70

Phe Gly Thr Gly Thr Lys Leu Thr Val Leu
1               5                   10

<210> SEQ ID NO 71
<211> LENGTH: 30
<212> TYPE: PRT
<213> ORGANISM: Artificial Sequence
<220> FEATURE:
<223> OTHER INFORMATION: C2-6B HFR1

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser
                20                  25                  30
```

<210> SEQ ID NO 72
<211> LENGTH: 14
<212> TYPE: PRT
<213> ORGANISM: Artificial Sequence
<220> FEATURE:
<223> OTHER INFORMATION: C2-6B HFR2

<400> SEQUENCE: 72

Trp Ile Arg Gln Ala Pro Gly Lys Gly Leu Glu Trp Val Ser
1               5                   10

<210> SEQ ID NO 73
<211> LENGTH: 32
<212> TYPE: PRT
<213> ORGANISM: Artificial Sequence
<220> FEATURE:
<223> OTHER INFORMATION: C2-6B HFR3

<400> SEQUENCE: 73

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Ile Tyr Phe Cys Ala Arg
            20                  25                  30

<210> SEQ ID NO 74
<211> LENGTH: 11
<212> TYPE: PRT
<213> ORGANISM: Artificial Sequence
<220> FEATURE:
<223> OTHER INFORMATION: C2-6B HFR4

<400> SEQUENCE: 74

Trp Gly Gln Gly Thr Leu Val Thr Val Ser Ser
1               5                   10

<210> SEQ ID NO 75
<211> LENGTH: 22
<212> TYPE: PRT
<213> ORGANISM: Artificial Sequence
<220> FEATURE:
<223> OTHER INFORMATION: C2-6B LFR1

<400> SEQUENCE: 75

Gln Ser Val Leu Ile Gln Pro Pro Ser Val Ser Gly Ser Pro Gly Gln
1               5                   10                  15

Ser Val Thr Ile Ser Cys
            20

<210> SEQ ID NO 76
<211> LENGTH: 15
<212> TYPE: PRT
<213> ORGANISM: Artificial Sequence
<220> FEATURE:
<223> OTHER INFORMATION: C2-6B LFR2

<400> SEQUENCE: 76

Trp Tyr Gln Gln His Pro Gly Lys Val Pro Lys Leu Met Ile Tyr
1               5                   10                  15

<210> SEQ ID NO 77
<211> LENGTH: 32
<212> TYPE: PRT
<213> ORGANISM: Artificial Sequence
<220> FEATURE:
<223> OTHER INFORMATION: C2-6B LFR3

<400> SEQUENCE: 77

```
Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Tyr Cys
                20                  25                  30

<210> SEQ ID NO 78
<211> LENGTH: 10
<212> TYPE: PRT
<213> ORGANISM: Artificial Sequence
<220> FEATURE:
<223> OTHER INFORMATION: C2-6B LFR4

<400> SEQUENCE: 78

Phe Gly Thr Gly Thr Lys Leu Thr Val Leu
1               5                   10

<210> SEQ ID NO 79
<211> LENGTH: 30
<212> TYPE: PRT
<213> ORGANISM: Artificial Sequence
<220> FEATURE:
<223> OTHER INFORMATION: C2-7A HFR1

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser
                20                  25                  30

<210> SEQ ID NO 80
<211> LENGTH: 14
<212> TYPE: PRT
<213> ORGANISM: Artificial Sequence
<220> FEATURE:
<223> OTHER INFORMATION: C2-7A HFR2

<400> SEQUENCE: 80

Trp Ile Arg Gln Ala Pro Gly Lys Gly Leu Glu Trp Val Ser
1               5                   10

<210> SEQ ID NO 81
<211> LENGTH: 32
<212> TYPE: PRT
<213> ORGANISM: Artificial Sequence
<220> FEATURE:
<223> OTHER INFORMATION: C2-7A HFR3

<400> SEQUENCE: 81

Arg Phe Thr Ile Ser Arg Asp Asn Ala Lys Asn Ser Leu Tyr Leu His
1               5                   10                  15

Met Asp Ser Leu Arg Ala Glu Asp Thr Ala Ile Tyr Phe Cys Ala Arg
                20                  25                  30

<210> SEQ ID NO 82
<211> LENGTH: 11
<212> TYPE: PRT
<213> ORGANISM: Artificial Sequence
<220> FEATURE:
<223> OTHER INFORMATION: C2-7A HFR4

<400> SEQUENCE: 82

Trp Gly Gln Gly Thr Leu Val Thr Val Ser Ser
1               5                   10
```

```
<210> SEQ ID NO 83
<211> LENGTH: 22
<212> TYPE: PRT
<213> ORGANISM: Artificial Sequence
<220> FEATURE:
<223> OTHER INFORMATION: C2-7A LFR1

<400> SEQUENCE: 83

Gln Ser Ala Leu Ile Gln Pro Pro Ser Val Ser Gly Ser Pro Gly Gln
1               5                   10                  15

Ser Val Thr Ile Ser Cys
            20

<210> SEQ ID NO 84
<211> LENGTH: 15
<212> TYPE: PRT
<213> ORGANISM: Artificial Sequence
<220> FEATURE:
<223> OTHER INFORMATION: C2-7A LFR2

<400> SEQUENCE: 84

Trp Tyr Gln Gln His Pro Gly Thr Val Pro Lys Leu Met Ile Tyr
1               5                   10                  15

<210> SEQ ID NO 85
<211> LENGTH: 32
<212> TYPE: PRT
<213> ORGANISM: Artificial Sequence
<220> FEATURE:
<223> OTHER INFORMATION: C2-7A LFR3

<400> SEQUENCE: 85

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 86
<211> LENGTH: 10
<212> TYPE: PRT
<213> ORGANISM: Artificial Sequence
<220> FEATURE:
<223> OTHER INFORMATION: C2-7A LFR4

<400> SEQUENCE: 86

Phe Gly Thr Gly Thr Lys Leu Thr Val Leu
1               5                   10

<210> SEQ ID NO 87
<211> LENGTH: 30
<212> TYPE: PRT
<213> ORGANISM: Artificial Sequence
<220> FEATURE:
<223> OTHER INFORMATION: C2-7B HFR1

<400> SEQUENCE: 87

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser
            20                  25                  30

<210> SEQ ID NO 88
<211> LENGTH: 14
<212> TYPE: PRT
<213> ORGANISM: Artificial Sequence
<220> FEATURE:
```

<223> OTHER INFORMATION: C2-7B HFR2

<400> SEQUENCE: 88

Trp Ile Arg Gln Ala Pro Gly Lys Gly Leu Glu Trp Val Ser
1               5                   10

<210> SEQ ID NO 89
<211> LENGTH: 32
<212> TYPE: PRT
<213> ORGANISM: Artificial Sequence
<220> FEATURE:
<223> OTHER INFORMATION: C2-7B HFR3

<400> SEQUENCE: 89

Arg Phe Thr Ile Ser Arg Asp Asn Ala Asn Asn Ser Leu Tyr Leu Gln
1               5                   10                  15

Met Asn Ser Leu Arg Thr Glu Asp Thr Ala Ile Tyr Tyr Cys Ala Arg
            20                  25                  30

<210> SEQ ID NO 90
<211> LENGTH: 11
<212> TYPE: PRT
<213> ORGANISM: Artificial Sequence
<220> FEATURE:
<223> OTHER INFORMATION: C2-7B HFR4

<400> SEQUENCE: 90

Trp Gly Gln Gly Thr Leu Val Thr Val Ser Ser
1               5                   10

<210> SEQ ID NO 91
<211> LENGTH: 22
<212> TYPE: PRT
<213> ORGANISM: Artificial Sequence
<220> FEATURE:
<223> OTHER INFORMATION: C2-7B LFR1

<400> SEQUENCE: 91

Gln Ser Val Leu Ile Gln Pro Pro Ser Val Ser Gly Ser Pro Gly Gln
1               5                   10                  15

Ser Val Thr Ile Ser Cys
            20

<210> SEQ ID NO 92
<211> LENGTH: 15
<212> TYPE: PRT
<213> ORGANISM: Artificial Sequence
<220> FEATURE:
<223> OTHER INFORMATION: C2-7B LFR2

<400> SEQUENCE: 92

Trp Tyr Gln Gln His Pro Gly Lys Val Pro Lys Leu Met Ile Tyr
1               5                   10                  15

<210> SEQ ID NO 93
<211> LENGTH: 32
<212> TYPE: PRT
<213> ORGANISM: Artificial Sequence
<220> FEATURE:
<223> OTHER INFORMATION: C2-7B LFR3

<400> SEQUENCE: 93

Gly Val Pro Asp Arg Phe Ser Gly Ser Lys Ser Gly Asp Thr Ala Ser
1               5                   10                  15

Leu Thr Ile Ser Gly Leu Gln Ala Glu Asp Glu Ala Asp Tyr Tyr Cys 20                  25                  30

<210> SEQ ID NO 94
<211> LENGTH: 10
<212> TYPE: PRT
<213> ORGANISM: Artificial Sequence
<220> FEATURE:
<223> OTHER INFORMATION: C2-7B LFR4

<400> SEQUENCE: 94

Phe Gly Thr Gly Thr Lys Leu Thr Val Leu
1               5                   10

<210> SEQ ID NO 95
<211> LENGTH: 30
<212> TYPE: PRT
<213> ORGANISM: Artificial Sequence
<220> FEATURE:
<223> OTHER INFORMATION: C2-7BN78K HFR1

<400> SEQUENCE: 95

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser
            20                  25                  30

<210> SEQ ID NO 96
<211> LENGTH: 14
<212> TYPE: PRT
<213> ORGANISM: Artificial Sequence
<220> FEATURE:
<223> OTHER INFORMATION: C2-7BN78K HFR2

<400> SEQUENCE: 96

Trp Ile Arg Gln Ala Pro Gly Lys Gly Leu Glu Trp Val Ser
1               5                   10

<210> SEQ ID NO 97
<211> LENGTH: 32
<212> TYPE: PRT
<213> ORGANISM: Artificial Sequence
<220> FEATURE:
<223> OTHER INFORMATION: C2-7BN78K HFR3

<400> SEQUENCE: 97

Arg Phe Thr Ile Ser Arg Asp Asn Ala Lys Asn Ser Leu Tyr Leu Gln
1               5                   10                  15

Met Asn Ser Leu Arg Thr Glu Asp Thr Ala Ile Tyr Tyr Cys Ala Arg
            20                  25                  30

<210> SEQ ID NO 98
<211> LENGTH: 11
<212> TYPE: PRT
<213> ORGANISM: Artificial Sequence
<220> FEATURE:
<223> OTHER INFORMATION: C2-7BN78K HFR4

<400> SEQUENCE: 98

Trp Gly Gln Gly Thr Leu Val Thr Val Ser Ser
1               5                   10

<210> SEQ ID NO 99
<211> LENGTH: 22
<212> TYPE: PRT
<213> ORGANISM: Artificial Sequence
<220> FEATURE:

```
<223> OTHER INFORMATION: C2-7BN78K LFR1

<400> SEQUENCE: 99

Gln Ser Val Leu Ile Gln Pro Pro Ser Val Ser Gly Ser Pro Gly Gln
1               5                   10                  15

Ser Val Thr Ile Ser Cys
            20

<210> SEQ ID NO 100
<211> LENGTH: 15
<212> TYPE: PRT
<213> ORGANISM: Artificial Sequence
<220> FEATURE:
<223> OTHER INFORMATION: C2-7BN78K LFR2

<400> SEQUENCE: 100

Trp Tyr Gln Gln His Pro Gly Lys Val Pro Lys Leu Met Ile Tyr
1               5                   10                  15

<210> SEQ ID NO 101
<211> LENGTH: 32
<212> TYPE: PRT
<213> ORGANISM: Artificial Sequence
<220> FEATURE:
<223> OTHER INFORMATION: C2-7BN78K LFR3

<400> SEQUENCE: 101

Gly Val Pro Asp Arg Phe Ser Gly Ser Lys Ser Gly Asp Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 102
<211> LENGTH: 10
<212> TYPE: PRT
<213> ORGANISM: Artificial Sequence
<220> FEATURE:
<223> OTHER INFORMATION: C2-7BN78K LFR4

<400> SEQUENCE: 102

Phe Gly Thr Gly Thr Lys Leu Thr Val Leu
1               5                   10

<210> SEQ ID NO 103
<211> LENGTH: 111
<212> TYPE: PRT
<213> ORGANISM: Artificial Sequence
<220> FEATURE:
<223> OTHER INFORMATION: C2-WT VL

<400> SEQUENCE: 103

Gln Ser Val Leu Ile Gln Pro Pro Ser Ala Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asp Thr Ala Ser Leu Thr Val Ser Gly Leu
65                  70                  75                  80

Gln Ala Glu Asp Glu Ala Asp Tyr Tyr Cys Ser Ser His Ala Gly Ser
                85                  90                  95
```

```
Asn Asn Phe Tyr Val Phe Gly Thr Gly Thr Lys Leu Thr Val Leu
            100                 105                 110
```

<210> SEQ ID NO 104
<211> LENGTH: 111
<212> TYPE: PRT
<213> ORGANISM: Artificial Sequence
<220> FEATURE:
<223> OTHER INFORMATION: C2-4A VL

<400> SEQUENCE: 104

```
Gln Ser Ala Leu Ile Gln Pro Pro Ser Ala Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110
```

<210> SEQ ID NO 105
<211> LENGTH: 111
<212> TYPE: PRT
<213> ORGANISM: Artificial Sequence
<220> FEATURE:
<223> OTHER INFORMATION: C2-4B VL

<400> SEQUENCE: 105

```
Gln Ser Val Leu Ile Gln Pro Pro Ser Val Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110
```

<210> SEQ ID NO 106
<211> LENGTH: 111
<212> TYPE: PRT
<213> ORGANISM: Artificial Sequence
<220> FEATURE:
<223> OTHER INFORMATION: C2-4C VL

<400> SEQUENCE: 106

```
Gln Ser Val Leu Ile Gln Pro Pro Ser Ala Ser Gly Ser Pro Gly Gln
1               5                   10                  15
```

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110

<210> SEQ ID NO 107
<211> LENGTH: 111
<212> TYPE: PRT
<213> ORGANISM: Artificial Sequence
<220> FEATURE:
<223> OTHER INFORMATION: C2-5A VL

<400> SEQUENCE: 107

Gln Ser Val Leu Ile Gln Pro Pro Ser Val Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110

<210> SEQ ID NO 108
<211> LENGTH: 111
<212> TYPE: PRT
<213> ORGANISM: Artificial Sequence
<220> FEATURE:
<223> OTHER INFORMATION: C2-5B VL

<400> SEQUENCE: 108

Gln Ser Val Leu Ile Gln Pro Pro Ser Ala Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110

```
<210> SEQ ID NO 109
<211> LENGTH: 111
<212> TYPE: PRT
<213> ORGANISM: Artificial Sequence
<220> FEATURE:
<223> OTHER INFORMATION: C2-5C VL

<400> SEQUENCE: 109
```

Gln Ser Val Leu Ile Gln Pro Pro Ser Val Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110

```
<210> SEQ ID NO 110
<211> LENGTH: 111
<212> TYPE: PRT
<213> ORGANISM: Artificial Sequence
<220> FEATURE:
<223> OTHER INFORMATION: C2-6A VL

<400> SEQUENCE: 110
```

Gln Ser Val Leu Ile Gln Pro Pro Ser Val Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110

```
<210> SEQ ID NO 111
<211> LENGTH: 111
<212> TYPE: PRT
<213> ORGANISM: Artificial Sequence
<220> FEATURE:
<223> OTHER INFORMATION: C2-6B VL

<400> SEQUENCE: 111
```

Gln Ser Val Leu Ile Gln Pro Pro Ser Val Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser His Ala Gly Ser
                 85                  90                  95

Asn Asn Phe Tyr Val Phe Gly Thr Gly Thr Lys Leu Thr Val Leu
            100                 105                 110

<210> SEQ ID NO 112
<211> LENGTH: 111
<212> TYPE: PRT
<213> ORGANISM: Artificial Sequence
<220> FEATURE:
<223> OTHER INFORMATION: C2-7A VL

<400> SEQUENCE: 112

Gln Ser Ala Leu Ile Gln Pro Pro Ser Val Ser Gly Ser Pro Gly Gln
 1               5                   10                  15

Ser Val Thr Ile Ser Cys Thr Gly Ile Ser Ser Asp Val Gly Ala Tyr
                 20                  25                  30

Asp Tyr Val Ser Trp Tyr Gln Gln His Pro Gly Thr Val Pro Lys Leu
        35                  40                  45

Met Ile Tyr Glu Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser His Ala Gly Ser
                 85                  90                  95

Asn Asn Phe Tyr Val Phe Gly Thr Gly Thr Lys Leu Thr Val Leu
            100                 105                 110

<210> SEQ ID NO 113
<211> LENGTH: 111
<212> TYPE: PRT
<213> ORGANISM: Artificial Sequence
<220> FEATURE:
<223> OTHER INFORMATION: C2-7B VL

<400> SEQUENCE: 113

Gln Ser Val Leu Ile Gln Pro Pro Ser Val Ser Gly Ser Pro Gly Gln
 1               5                   10                  15

Ser Val Thr Ile Ser Cys Thr Gly Ile Ser Ser Asp Val Gly Ala Tyr
                 20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
 50                  55                  60

Ser Gly Ser Lys Ser Gly Asp Thr Ala Ser Leu Thr Ile Ser Gly Leu
 65                  70                  75                  80

Gln Ala Glu Asp Glu Ala Asp Tyr Tyr Cys Ser Ser His Ala Gly Ser
                 85                  90                  95

Asn Asn Phe Tyr Val Phe Gly Thr Gly Thr Lys Leu Thr Val Leu
            100                 105                 110

<210> SEQ ID NO 114

<211> LENGTH: 111
<212> TYPE: PRT
<213> ORGANISM: Artificial Sequence
<220> FEATURE:
<223> OTHER INFORMATION: C2-7BN78K VL

<400> SEQUENCE: 114

```
Gln Ser Val Leu Ile Gln Pro Pro Ser Val Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110
```

<210> SEQ ID NO 115
<211> LENGTH: 333
<212> TYPE: DNA
<213> ORGANISM: Artificial Sequence
<220> FEATURE:
<223> OTHER INFORMATION: C2-WT VL Nucleotide

<400> SEQUENCE: 115

```
cagtctgttc tgattcagcc tcccteegeg teegggtete etggacagte agteaccate      60
tcctgcactg gaatcagcag tgacgttggt gcttatgact atgtctcctg gtaccaacag    120
cacccaggca aagtccccaa actcatgatt tatgaggtca gtaagcggcc ctcaggggtc    180
cctgatcgct tctctggctc caagtctggc gacacggcct ccctgaccgt ctctgggctc    240
caggctgagg atgaggctga ttactactgc agctcacatg caggcagcaa caatttttat    300
gtcttcggaa ctgggaccaa gctgaccgtc cta                                 333
```

<210> SEQ ID NO 116
<211> LENGTH: 333
<212> TYPE: DNA
<213> ORGANISM: Artificial Sequence
<220> FEATURE:
<223> OTHER INFORMATION: C2-4A VL Nucleotide

<400> SEQUENCE: 116

```
cagagcgccc tgatccagcc ccccagcgcc agcggcagcc ccggccagag cgtgaccatc      60
agctgcaccg gcatcagcag cgacgtgggc gcctacgact acgtgagctg gtaccagcag    120
caccccggca aggtgcccaa gctgatgatc tacgaggtga gcaagagggcc agcggcgtg    180
cccgacaggt tcagcggcag caagagcggc aacaccgcca gcctgaccat cagcggcctg    240
caggccgagg acgaggccga ctactactgc agcagccacg ccggcagcaa caacttctac    300
gtgttcggca ccggcaccaa gctgaccgtg ctg                                 333
```

<210> SEQ ID NO 117
<211> LENGTH: 333
<212> TYPE: DNA
<213> ORGANISM: Artificial Sequence
<220> FEATURE:

<223> OTHER INFORMATION: C2-4B VL Nucleotide

<400> SEQUENCE: 117

| | |
|---|---|
| cagtccgtgc tgatccagcc tccttccgtg agcggaagcc ctggccagtc cgtcaccatc | 60 |
| agctgcaccg gaatcagctc cgacgtgggc gcctacgact acgtgagctg gtatcaacag | 120 |
| caccccggca aggtgcccaa gctgatgatc tacgaggtga gcaagaggcc tagcggcgtg | 180 |
| cccgacaggt ttagcggcag caagtctggt gacaccgcca gcctgaccat cagcggactg | 240 |
| caggccgaag acgaggccga ctactactgc agctcccatg ccggctccaa caacttttac | 300 |
| gtgttcggca ccggcaccaa gctgacagtg ctg | 333 |

<210> SEQ ID NO 118
<211> LENGTH: 333
<212> TYPE: DNA
<213> ORGANISM: Artificial Sequence
<220> FEATURE:
<223> OTHER INFORMATION: C2-4C VL Nucleotide

<400> SEQUENCE: 118

| | |
|---|---|
| cagagcgtgc tgatccagcc ccccagcgcc agcggcagcc ccggccagag cgtgaccatc | 60 |
| agctgcaccg gcatcagcag cgacgtgggc gcctacgact acgtgagctg gtaccagcag | 120 |
| caccccggca aggtgcccaa gctgatgatc tacgaggtga gcaagaggcc cagcggcgtg | 180 |
| cccgacaggt tcagcggcag caagagcggc aacaccgcca gcctgaccgt gagcggcctg | 240 |
| caggccgagg acgaggccga ctactactgc agcagccacg ccggcagcaa caacttctac | 300 |
| gtgttcggca ccggcaccaa gctgaccgtg ctg | 333 |

<210> SEQ ID NO 119
<211> LENGTH: 333
<212> TYPE: PRT
<213> ORGANISM: Artificial Sequence
<220> FEATURE:
<223> OTHER INFORMATION: C2-5A VL Nucleotide

<400> SEQUENCE: 119

Cys Ala Gly Ala Gly Cys Gly Thr Gly Cys Thr Gly Ala Thr Cys Cys
1               5                   10                  15

Ala Gly Cys Cys Cys Cys Cys Cys Ala Gly Cys Gly Thr Gly Ala Gly
            20                  25                  30

Cys Gly Gly Cys Ala Gly Cys Cys Cys Cys Gly Gly Cys Cys Ala Gly
        35                  40                  45

Ala Gly Cys Gly Thr Gly Ala Cys Cys Ala Thr Cys Ala Gly Cys Thr
    50                  55                  60

Gly Cys Ala Cys Cys Gly Gly Cys Ala Thr Cys Ala Gly Cys Ala Gly
65                  70                  75                  80

Cys Gly Ala Cys Gly Thr Gly Gly Gly Cys Gly Cys Cys Thr Ala Cys
                85                  90                  95

Gly Ala Cys Thr Ala Cys Gly Thr Gly Ala Gly Cys Thr Gly Gly Thr
            100                 105                 110

Ala Cys Cys Ala Gly Cys Ala Gly Cys Ala Cys Cys Cys Cys Gly Gly
        115                 120                 125

Cys Ala Ala Gly Gly Thr Gly Cys Cys Cys Ala Ala Gly Cys Thr Gly
    130                 135                 140

Ala Thr Gly Ala Thr Cys Thr Ala Cys Gly Ala Gly Gly Thr Gly Ala
145                 150                 155                 160

Gly Cys Ala Ala Gly Ala Gly Gly Cys Cys Cys Ala Gly Cys Gly Gly

```
                165                 170                 175
Cys Gly Thr Gly Cys Cys Gly Ala Cys Ala Gly Thr Thr Cys
                180                 185                 190
Ala Gly Cys Gly Gly Cys Ala Gly Cys Ala Gly Ala Gly Cys Gly
                195                 200                 205
Gly Cys Ala Ala Cys Ala Cys Cys Gly Cys Cys Ala Gly Cys Cys Thr
            210                 215                 220
Gly Ala Cys Cys Ala Thr Cys Ala Gly Cys Gly Gly Cys Cys Thr Gly
225                 230                 235                 240
Cys Ala Gly Gly Cys Cys Gly Ala Gly Gly Ala Cys Gly Ala Gly Gly
                245                 250                 255
Cys Cys Gly Ala Cys Thr Ala Cys Thr Ala Cys Thr Gly Cys Ala Gly
                260                 265                 270
Cys Ala Gly Cys Ala Cys Gly Cys Cys Gly Gly Cys Ala Gly Cys
                275                 280                 285
Ala Ala Cys Ala Ala Cys Thr Thr Cys Thr Ala Cys Gly Thr Gly Thr
            290                 295                 300
Thr Cys Gly Gly Cys Ala Cys Cys Gly Gly Cys Ala Cys Cys Ala Ala
305                 310                 315                 320
Gly Cys Thr Gly Ala Cys Cys Gly Thr Gly Cys Thr Gly
                325                 330

<210> SEQ ID NO 120
<211> LENGTH: 333
<212> TYPE: DNA
<213> ORGANISM: Artificial Sequence
<220> FEATURE:
<223> OTHER INFORMATION: C2-5B VL Nucleotide

<400> SEQUENCE: 120
cagagcgtgc tgatccagcc ccccagcgcc agcggcagcc ccggccagag cgtgaccatc    60
agctgcaccg gcatcagcag cgacgtgggc gcctacgact acgtgagctg gtaccagcag   120
caccccggca aggtgcccaa gctgatgatc tacgaggtga gcaagaggcc agcggcgtg   180 cccgacaggt tcagcggcag caagagcggc aacaccgcca gcctgaccat cagcggcctg   240
caggccgagg acgaggccga ctactactgc agcagccacg ccggcagcaa caacttctac   300
gtgttcggca ccggcaccaa gctgaccgtg ctg                                333

<210> SEQ ID NO 121
<211> LENGTH: 333
<212> TYPE: DNA
<213> ORGANISM: Artificial Sequence
<220> FEATURE:
<223> OTHER INFORMATION: C2-5C VL Nucleotide

<400> SEQUENCE: 121
cagagcgtgc tgatccagcc ccccagcgtg agcggcagcc ccggccagag cgtgaccatc    60
agctgcaccg gcatcagcag cgacgtgggc gcctacgact acgtgagctg gtaccagcag   120
caccccggca aggtgcccaa gctgatgatc tacgaggtga gcaagaggcc agcggcgtg   180 cccgacaggt tcagcggcag caagagcggc gacaccgcca gcctgaccat cagcggcctg   240
caggccgagg acgaggccga ctactactgc agcagccacg ccggcagcaa caacttctac   300
gtgttcggca ccggcaccaa gctgaccgtg ctg                                333

<210> SEQ ID NO 122
<211> LENGTH: 333
```

```
<212> TYPE: DNA
<213> ORGANISM: Artificial Sequence
<220> FEATURE:
<223> OTHER INFORMATION: C2-6A VL Nucleotide

<400> SEQUENCE: 122
cagagcgtgc tgatccagcc ccccagcgtg agcggcagcc ccggccagag cgtgaccatc    60
agctgcaccg gcatcagcag cgacgtgggc gcctacgact acgtgagctg gtaccagcag   120
caccccggca aggtgcccaa gctgatgatc tacgaggtga gcaagaggcc cagcggcgtg   180
cccgacaggt tcagcggcag caagagcggc aacaccgcca gcctgaccat cagcggcctg   240
caggccgagg acgaggccga ctactactgc agcagccacg ccggcagcaa caacttctac   300
gtgttcggca ccggcaccaa gctgaccgtg ctg                                333

<210> SEQ ID NO 123
<211> LENGTH: 333
<212> TYPE: DNA
<213> ORGANISM: Artificial Sequence
<220> FEATURE:
<223> OTHER INFORMATION: C2-6B VL Nucleotide

<400> SEQUENCE: 123
cagagcgtgc tgatccagcc ccccagcgtg agcggcagcc ccggccagag cgtgaccatc    60
agctgcaccg gcatcagcag cgacgtgggc gcctacgact acgtgagctg gtaccagcag   120
caccccggca aggtgcccaa gctgatgatc tacgaggtga gcaagaggcc cagcggcgtg   180
cccgacaggt tcagcggcag caagagcggc aacaccgcca gcctgaccgt gagcggcctg   240
caggccgagg acgaggccga ctactactgc agcagccacg ccggcagcaa caacttctac   300
gtgttcggca ccggcaccaa gctgaccgtg ctg                                333

<210> SEQ ID NO 124
<211> LENGTH: 333
<212> TYPE: DNA
<213> ORGANISM: Artificial Sequence
<220> FEATURE:
<223> OTHER INFORMATION: C2-7A VL Nucleotide

<400> SEQUENCE: 124
cagagcgccc tgatccagcc tccttccgtg agcggcagcc ctggacagag cgtgaccatc    60
tcctgcaccg gaatcagcag cgacgtgggc gcctacgact atgtgagctg gtatcaacag   120
caccccggaa ccgtccccaa gctcatgatc tacgaggtga gcaagaggcc cagcggagtg   180
cccgataggt tctccggcag caaaagcggc aataccgcta gcctgaccat tagcggcctg   240
caggccgagg atgaggccga ctactactgc agcagccacg ccggctccaa caacttctat   300
gtgttcggca ccggcaccaa actgaccgtg ctg                                333

<210> SEQ ID NO 125
<211> LENGTH: 333
<212> TYPE: DNA
<213> ORGANISM: Artificial Sequence
<220> FEATURE:
<223> OTHER INFORMATION: C2-7B VL Nucleotide

<400> SEQUENCE: 125
cagagcgtgc tgattcagcc tcccagcgtg agcggaagcc ctggacagag cgtgaccatc    60
agctgcaccg gcatcagctc cgatgtgggc gcctacgact acgtgagctg gtatcaacag   120
caccctggca aggtgcccaa gctgatgatc tacgaggtgt ccaaaaggcc cagcggcgtg   180
```

```
cccgataggt ttagcggctc caagtccggc gacacagcct ccctgaccat cagcggcctc    240
caggctgagg atgaggccga ctactactgc agcagccatg ccggcagcaa caactttac     300 gtgttcggca ccggcacaaa gctgaccgtg ctg                                  333
```

<210> SEQ ID NO 126
<211> LENGTH: 333
<212> TYPE: DNA
<213> ORGANISM: Artificial Sequence
<220> FEATURE:
<223> OTHER INFORMATION: C2-7BN78K VL Nucleotide

<400> SEQUENCE: 126

```
cagagcgtgc tgattcagcc tcccagcgtg agcggaagcc tggacagag cgtgaccatc      60 agctgcaccg gcatcagctc cgatgtgggc gcctacgact acgtgagctg gtatcaacag    120
caccctggca aggtgcccaa gctgatgatc tacgaggtgt ccaaaaggcc cagcggcgtg    180
cccgataggt ttagcggctc caagtccggc gacacagcct ccctgaccat cagcggcctc    240
caggctgagg atgaggccga ctactactgc agcagccatg ccggcagcaa caactttac     300 gtgttcggca ccggcacaaa gctgaccgtg ctg                                  333
```

<210> SEQ ID NO 127
<211> LENGTH: 124
<212> TYPE: PRT
<213> ORGANISM: Artificial Sequence
<220> FEATURE:
<223> OTHER INFORMATION: C2-WT VH

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Asn Asn Ser
65                  70                  75                  80

Leu Tyr Leu His Met Asp Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120

<210> SEQ ID NO 128
<211> LENGTH: 124
<212> TYPE: PRT
<213> ORGANISM: Artificial Sequence
<220> FEATURE:
<223> OTHER INFORMATION: C2-4A VH

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val

```
                35                  40                  45
Ser Tyr Ile Ser Ser Ser Ala Ser Gly Ser Thr Ile Tyr Tyr Ala Asp
    50                  55                  60
Ser Val Lys Gly Arg Phe Thr Ile Ser Arg Asp Asn Ala Lys Asn Ser
65                  70                  75                  80
Leu Tyr Leu His Met Asp Ser Leu Arg Ala Glu Asp Thr Ala Ile Tyr
                85                  90                  95
Phe Cys Ala Arg Val Val Pro Ala Gly Ser Gly Trp Arg Trp Phe Asp
            100                 105                 110
Pro Trp Gly Gln Gly Thr Leu Val Thr Val Ser Ser
            115                 120
```

<210> SEQ ID NO 129
<211> LENGTH: 124
<212> TYPE: PRT
<213> ORGANISM: Artificial Sequence
<220> FEATURE:
<223> OTHER INFORMATION: C2-4B VH

<400> SEQUENCE: 129

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Val Ser Asp Tyr
            20                  25                  30
Tyr Met Asn Trp Phe Arg Gln Ala Pro Gly Lys Gly Leu Glu Trp Val
                35                  40                  45
Ser Tyr Ile Ser Ser Ser Ala Ser Gly Ser Thr Ile Tyr Tyr Ala Asp
    50                  55                  60
Ser Val Lys Gly Arg Phe Thr Ile Ser Arg Asp Asn Ala Asn Asn Ser
65                  70                  75                  80
Leu Tyr Leu His Met Asp Ser Leu Arg Ala Glu Asp Thr Ala Ile Tyr
                85                  90                  95
Phe Cys Ala Arg Val Val Pro Ala Gly Ser Gly Trp Arg Trp Phe Asp
            100                 105                 110
Pro Trp Gly Gln Gly Thr Leu Val Thr Val Ser Ser
            115                 120
```

<210> SEQ ID NO 130
<211> LENGTH: 124
<212> TYPE: PRT
<213> ORGANISM: Artificial Sequence
<220> FEATURE:
<223> OTHER INFORMATION: C2-4C VH

<400> SEQUENCE: 130

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Ser Asp Tyr
            20                  25                  30
Tyr Met Asn Trp Ile Arg Gln Ala Pro Gly Lys Gly Leu Glu Trp Val
                35                  40                  45
Ser Tyr Ile Ser Ser Ser Ala Ser Gly Ser Thr Ile Tyr Tyr Ala Asp
    50                  55                  60
Ser Val Lys Gly Arg Phe Thr Ile Ser Arg Asp Asn Ala Lys Asn Ser
65                  70                  75                  80
Leu Tyr Leu Gln Met Asn Ser Leu Arg Ala Glu Asp Thr Ala Ile Tyr
                85                  90                  95
```

```
Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120
```

<210> SEQ ID NO 131
<211> LENGTH: 124
<212> TYPE: PRT
<213> ORGANISM: Artificial Sequence
<220> FEATURE:
<223> OTHER INFORMATION: C2-5A VH

<400> SEQUENCE: 131

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu His Met Asp Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120
```

<210> SEQ ID NO 132
<211> LENGTH: 124
<212> TYPE: PRT
<213> ORGANISM: Artificial Sequence
<220> FEATURE:
<223> OTHER INFORMATION: C2-5B VH

<400> SEQUENCE: 132

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120
```

<210> SEQ ID NO 133
<211> LENGTH: 124
<212> TYPE: PRT
<213> ORGANISM: Artificial Sequence

<220> FEATURE:
<223> OTHER INFORMATION: C2-5C VH

<400> SEQUENCE: 133

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Asp Tyr
            20                  25                  30

Tyr Met Asn Trp Phe Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Asn Asn Ser
65                  70                  75                  80

Leu Tyr Leu His Met Asp Ser Leu Arg Ala Glu Asp Thr Ala Ile Tyr
                85                  90                  95

Tyr Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120

<210> SEQ ID NO 134
<211> LENGTH: 124
<212> TYPE: PRT
<213> ORGANISM: Artificial Sequence
<220> FEATURE:
<223> OTHER INFORMATION: C2-6A VH

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120

<210> SEQ ID NO 135
<211> LENGTH: 124
<212> TYPE: PRT
<213> ORGANISM: Artificial Sequence
<220> FEATURE:
<223> OTHER INFORMATION: C2-6B VH

<400> SEQUENCE: 135

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser Asp Tyr
            20                  25                  30

```
Tyr Met Asn Trp Ile Arg Gln Ala Pro Gly Lys Gly Leu Glu Trp Val
            35                  40                  45

Ser Tyr Ile Ser Ser Ser Ala Ser Gly Ser Thr Ile Tyr Tyr Ala Asp
     50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Ile Tyr
                 85                  90                  95

Phe Cys Ala Arg Val Val Pro Ala Gly Ser Gly Trp Arg Trp Phe Asp
                100                 105                 110

Pro Trp Gly Gln Gly Thr Leu Val Thr Val Ser Ser
         115                 120
```

<210> SEQ ID NO 136
<211> LENGTH: 124
<212> TYPE: PRT
<213> ORGANISM: Artificial Sequence
<220> FEATURE:
<223> OTHER INFORMATION: C2-7A VH

<400> SEQUENCE: 136

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Val Ser Asp Tyr
                20                  25                  30

Tyr Met Asn Trp Ile Arg Gln Ala Pro Gly Lys Gly Leu Glu Trp Val
            35                  40                  45

Ser Tyr Ile Ser Ser Ser Ala Ser Gly Ser Thr Ile Tyr Tyr Ala Asp
     50                  55                  60

Ser Val Lys Gly Arg Phe Thr Ile Ser Arg Asp Asn Ala Lys Asn Ser
 65                  70                  75                  80

Leu Tyr Leu His Met Asp Ser Leu Arg Ala Glu Asp Thr Ala Ile Tyr
                 85                  90                  95

Phe Cys Ala Arg Val Val Pro Ala Gly Ser Gly Trp Arg Trp Phe Asp
                100                 105                 110

Pro Trp Gly Gln Gly Thr Leu Val Thr Val Ser Ser
         115                 120
```

<210> SEQ ID NO 137
<211> LENGTH: 124
<212> TYPE: PRT
<213> ORGANISM: Artificial Sequence
<220> FEATURE:
<223> OTHER INFORMATION: C2-7B VH

<400> SEQUENCE: 137

```
Glu Val Gln Leu Val Glu Ser Gly Gly Gly Leu Val Lys Pro Gly Gly
 1               5                  10                  15

Ser Leu Arg Leu Ser Cys Ala Ser Gly Phe Thr Val Ser Asp Tyr
                20                  25                  30

Tyr Met Asn Trp Ile Arg Gln Ala Pro Gly Lys Gly Leu Glu Trp Val
            35                  40                  45

Ser Tyr Ile Ser Ser Ser Ala Ser Gly Ser Thr Ile Tyr Tyr Ala Asp
     50                  55                  60

Ser Val Lys Gly Arg Phe Thr Ile Ser Arg Asp Asn Ala Asn Asn Ser
 65                  70                  75                  80

Leu Tyr Leu Gln Met Asn Ser Leu Arg Thr Glu Asp Thr Ala Ile Tyr
                 85                  90                  95
```

Tyr Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120

```
<210> SEQ ID NO 138
<211> LENGTH: 124
<212> TYPE: PRT
<213> ORGANISM: Artificial Sequence
<220> FEATURE:
<223> OTHER INFORMATION: C2-7BN78K VH

<400> SEQUENCE: 138
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
            35                  40                  45

Ser Tyr Ile Ser Ser Ser Ala Ser Gly Ser Thr Ile Tyr Tyr Ala Asp
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Thr Glu Asp Thr Ala Ile Tyr
                85                  90                  95

Tyr Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120

```
<210> SEQ ID NO 139
<211> LENGTH: 372
<212> TYPE: DNA
<213> ORGANISM: Artificial Sequence
<220> FEATURE:
<223> OTHER INFORMATION: C2-WT VH Nucleotide

<400> SEQUENCE: 139
gaggtgcagc tggtggagtc tgggggaggc ttggtacagc ctggagggtc cctgagactc      60
tcctgtgcag cctctggatt caccgtcagt gactactaca tgaactggat ccgccaggct     120
ccagggaagg gcctggagtg ggtttcatac attagtagta gtgctagtgg tagtaccata     180
tactacgcag actctgtgaa gggccgattc accatctcca gggacaacgc caacaactca     240
ctgtatctgc acatggacag cctgagagcc gaggacacgg ccatatactt ctgtgcgaga     300
gtcgtcccag ctggaagtgg gtggaggtgg ttcgacccct ggggccaggg taccctggtc     360
actgtctcct ca                                                         372

<210> SEQ ID NO 140
<211> LENGTH: 372
<212> TYPE: DNA
<213> ORGANISM: Artificial Sequence
<220> FEATURE:
<223> OTHER INFORMATION: C2-4A VH Nucleotide

<400> SEQUENCE: 140
gaggtgcagc tggtggagag cggcggcggc ctggtgcagc ccggcggcag cctgaggctg      60
agctgcgccg ccagcggctt caccgtgagc gactactaca tgaactggat caggcaggcc     120
```

| | |
|---|---|
| cccggcaagg gcctggagtg ggtgagctac atcagcagca gcgccagcgg cagcaccatc | 180 |
| tactacgccg acagcgtgaa gggcaggttc accatcagca gggacaacgc caagaacagc | 240 |
| ctgtacctgc acatggacag cctgagggcc gaggacaccg ccatctactt ctgcgccagg | 300 |
| gtggtgcccg ccggcagcgg ctggaggtgg ttcgaccctc ggggccaggg caccctggtg | 360 |
| accgtgagca gc | 372 |

<210> SEQ ID NO 141
<211> LENGTH: 372
<212> TYPE: DNA
<213> ORGANISM: Artificial Sequence
<220> FEATURE:
<223> OTHER INFORMATION: C2-4B VH Nucleotide

<400> SEQUENCE: 141

| | |
|---|---|
| gaggtgcagc tggtggagtc cggcggagga ctggtgcaac tggcagaag cctgagactg | 60 |
| agctgtgccg ccagcggctt caccgtgtcc gactactaca tgaactggtt caggcaggct | 120 |
| cccggcaagg gcctggaatg ggtgagctac atcagcagca gcgctagcgg aagcaccatc | 180 |
| tactatgccg acagcgtgaa gggcaggttc accatcagca gggacaacgc caacaactcc | 240 |
| ctgtacctgc acatggacag cctgagggcc gaagacaccg ccatctactt ctgtgccaga | 300 |
| gtggtgcctg ctggctccgg ctggaggtgg ttcgatccct ggggacaggg caccctggtg | 360 |
| accgtgagct ct | 372 |

<210> SEQ ID NO 142
<211> LENGTH: 372
<212> TYPE: DNA
<213> ORGANISM: Artificial Sequence
<220> FEATURE:
<223> OTHER INFORMATION: C2-4C VH Nucleotide

<400> SEQUENCE: 142

| | |
|---|---|
| gaggtgcagc tggtggagag cggcggcggc ctggtgcagc ccggcggcag cctgaggctg | 60 |
| agctgcgccg ccagcggctt caccgtgagc gactactaca tgaactggat caggcaggcc | 120 |
| cccggcaagg gcctggagtg ggtgagctac atcagcagca gcgccagcgg cagcaccatc | 180 |
| tactacgccg acagcgtgaa gggcaggttc accatcagca gggacaacgc caagaacagc | 240 |
| ctgtacctgc agatgaacag cctgagggcc gaggacaccg ccatctactt ctgcgccagg | 300 |
| gtggtgcccg ccggcagcgg ctggaggtgg ttcgaccct ggggccaggg caccctggtg | 360 |
| accgtgagca gc | 372 |

<210> SEQ ID NO 143
<211> LENGTH: 372
<212> TYPE: DNA
<213> ORGANISM: Artificial Sequence
<220> FEATURE:
<223> OTHER INFORMATION: C2-5A VH Nucleotide

<400> SEQUENCE: 143

| | |
|---|---|
| gaggtgcagc tggtggagag cggcggcggc ctggtgcagc ccggcaggag cctgaggctg | 60 |
| agctgcgccg ccagcggctt caccgtgagc gactactaca tgaactggat caggcaggcc | 120 |
| cccggcaagg gcctggagtg ggtgagctac atcagcagca gcgccagcgg cagcaccatc | 180 |
| tactacgccg acagcgtgaa gggcaggttc accatcagca gggacaacgc caagaacagc | 240 |
| ctgtacctgc acatggacag cctgagggcc gaggacaccg ccatctactt ctgcgccagg | 300 |
| gtggtgcccg ccggcagcgg ctggaggtgg ttcgaccct ggggccaggg caccctggtg | 360 | accgtgagca gc					372

<210> SEQ ID NO 144
<211> LENGTH: 372
<212> TYPE: DNA
<213> ORGANISM: Artificial Sequence
<220> FEATURE:
<223> OTHER INFORMATION: C2-5B VH Nucleotide

<400> SEQUENCE: 144
gaggtgcagc tggtggagag cggcggcggc ctggtgcagc ccggcggcag cctgaggctg		60 agctgcgccg ccagcggctt caccgtgagc gactactaca tgaactggat caggcaggcc		120 cccggcaagg gcctggagtg ggtgagctac atcagcagca gcgccagcgg cagcaccatc		180 tactacgccg acagcgtgaa gggcaggttc accatcagca gggacaacgc caagaacagc		240 ctgtacctgc agatgaacag cctgagggcc gaggacaccg ccatctactt ctgcgccagg		300 gtggtgcccg ccggcagcgg ctggaggtgg ttcgacccct ggggccaggg caccctggtg		360 accgtgagca gc					372

<210> SEQ ID NO 145
<211> LENGTH: 372
<212> TYPE: DNA
<213> ORGANISM: Artificial Sequence
<220> FEATURE:
<223> OTHER INFORMATION: C2-5C VH Nucleotide

<400> SEQUENCE: 145
gaggtgcagc tggtggagag cggcggcggc ctggtgcagc ccggcaggag cctgaggctg		60 agctgcgccg ccagcggctt caccgtgagc gactactaca tgaactggtt caggcaggcc		120 cccggcaagg gcctggagtg ggtgagctac atcagcagca gcgccagcgg cagcaccatc		180 tactacgccg acagcgtgaa gggcaggttc accatcagca gggacaacgc caacaacagc		240 ctgtacctgc acatggacag cctgagggcc gaggacaccg ccatctacta ctgcgccagg		300 gtggtgcccg ccggcagcgg ctggaggtgg ttcgacccct ggggccaggg caccctggtg		360 accgtgagca gc					372

<210> SEQ ID NO 146
<211> LENGTH: 372
<212> TYPE: DNA
<213> ORGANISM: Artificial Sequence
<220> FEATURE:
<223> OTHER INFORMATION: C2-6A VH Nucleotide

<400> SEQUENCE: 146
gaggtgcagc tggtggagag cggcggcggc ctggtgcagc ccggcggcag cctgaggctg		60 agctgcgccg ccagcggctt caccgtgagc gactactaca tgaactggat caggcaggcc		120 cccggcaagg gcctggagtg ggtgagctac atcagcagca gcgccagcgg cagcaccatc		180 tactacgccg acagcgtgaa gggcaggttc accatcagca gggacaacgc caagaacagc		240 ctgtacctgc agatgaacag cctgagggcc gaggacaccg ccatctactt ctgcgccagg		300 gtggtgcccg ccggcagcgg ctggaggtgg ttcgacccct ggggccaggg caccctggtg		360 accgtgagca gc					372

<210> SEQ ID NO 147
<211> LENGTH: 372
<212> TYPE: DNA

<213> ORGANISM: Artificial Sequence
<220> FEATURE:
<223> OTHER INFORMATION: C2-6B VH Nucleotide

<400> SEQUENCE: 147

| | |
|---|---|
| gaggtgcagc tggtggagag cggcggcggc ctggtgaagc ccggcggcag cctgaggctg | 60 |
| agctgcgccg ccagcggctt caccgtgagc gactactaca tgaactggat caggcaggcc | 120 |
| cccggcaagg gcctggagtg ggtgagctac atcagcagca cgccagcgg cagcaccatc | 180 |
| tactacgccg acagcgtgaa gggcaggttc accatcagca gggacaacgc caagaacagc | 240 |
| ctgtacctgc agatgaacag cctgagggcc gaggacaccg ccatctactt ctgcgccagg | 300 |
| gtggtgcccg ccggcagcgg ctggaggtgg ttcgacccct ggggccaggg caccctggtg | 360 |
| accgtgagca gc | 372 |

<210> SEQ ID NO 148
<211> LENGTH: 372
<212> TYPE: DNA
<213> ORGANISM: Artificial Sequence
<220> FEATURE:
<223> OTHER INFORMATION: C2-7A VH Nucleotide

<400> SEQUENCE: 148

| | |
|---|---|
| gaggtgcagc tggtggaatc tggtggcgga ctggtgaagc ctggcggttc tctgagactg | 60 |
| agctgtgccg ccagcggctt caccgtgagc gactactaca tgaactggat caggcaggcc | 120 |
| cccggcaaag gcctggaatg ggtgagctac atcagctcct ccgcctctgg ttctaccatc | 180 |
| tactacgccg acagcgtgaa gggcaggttc accatcagca gggacaacgc caagaacagc | 240 |
| ctctacctgc acatggacag cctgagggcc gaggacaccg ctatctactt ctgcgccaga | 300 |
| gtggtgcctg ctggttctgg ctggagatgg ttcgatcctt ggggccaggg caccctggtg | 360 |
| acagtgagca gc | 372 |

<210> SEQ ID NO 149
<211> LENGTH: 372
<212> TYPE: DNA
<213> ORGANISM: Artificial Sequence
<220> FEATURE:
<223> OTHER INFORMATION: C2-7B VH Nucleotide

<400> SEQUENCE: 149

| | |
|---|---|
| gaggtgcagc tggtggaaag cggcggcgga ctggtgaagc ctggaggttc tctgaggctg | 60 |
| agctgtgccg cctccggctt caccgtgagc gactactaca tgaactggat caggcaggcc | 120 |
| cccggcaaag gactggagtg ggtgagctac atctcctcct ccgcctccgg cagcaccatc | 180 |
| tactacgccg actccgtgaa gggcaggttc accatctcca gggataacgc caacaacagc | 240 |
| ctgtacctgc agatgaactc cctgaggacc gaggacaccg ccatctacta ctgtgccagg | 300 |
| gtggtgcccg ctggaagcgg atggaggtgg ttcgacccct ggggccaggg aacactggtg | 360 |
| accgtgagca gc | 372 |

<210> SEQ ID NO 150
<211> LENGTH: 372
<212> TYPE: DNA
<213> ORGANISM: Artificial Sequence
<220> FEATURE:
<223> OTHER INFORMATION: C2-7BN78K VH Nucleotide

<400> SEQUENCE: 150

| | |
|---|---|
| gaggtgcagc tggtggaaag cggcggcgga ctggtgaagc ctggaggttc tctgaggctg | 60 |

-continued

```
agctgtgccg cctccggctt caccgtgagc gactactaca tgaactggat caggcaggcc    120
cccggcaaag gactggagtg ggtgagctac atctcctcct ccgcctccgg cagcaccatc    180
tactacgccg actccgtgaa gggcaggttc accatctcca gggataacgc caagaacagc    240
ctgtacctgc agatgaactc cctgaggacc gaggacaccg ccatctacta ctgtgccagg    300
gtggtgcccg ctggaagcgg atggaggtgg ttcgacccct ggggccaggg aacactggtg    360
accgtgagca gc                                                        372
```

<210> SEQ ID NO 151
<211> LENGTH: 489
<212> TYPE: PRT
<213> ORGANISM: Artificial Sequence
<220> FEATURE:
<223> OTHER INFORMATION: C2-WT-Fc

<400> SEQUENCE: 151

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Asn Asn Ser
65                  70                  75                  80

Leu Tyr Leu His Met Asp Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser Gly Ile Leu Gly
        115                 120                 125

Ser Gly Gly Gly Gly Ser Gly Gly Gly Ser Gly Gly Gly Gly Ser
    130                 135                 140

Gln Ser Val Leu Ile Gln Pro Pro Ser Ala Ser Gly Ser Pro Gly Gln
145                 150                 155                 160

Ser Val Thr Ile Ser Cys Thr Gly Ile Ser Ser Asp Val Gly Ala Tyr
                165                 170                 175

Asp Tyr Val Ser Trp Tyr Gln Gln His Pro Gly Lys Val Pro Lys Leu
            180                 185                 190

Met Ile Tyr Glu Val Ser Lys Arg Pro Ser Gly Val Pro Asp Arg Phe
        195                 200                 205

Ser Gly Ser Lys Ser Gly Asp Thr Ala Ser Leu Thr Val Ser Gly Leu
    210                 215                 220

Gln Ala Glu Asp Glu Ala Asp Tyr Tyr Cys Ser Ser His Ala Gly Ser
225                 230                 235                 240

Asn Asn Phe Tyr Val Phe Gly Thr Gly Thr Lys Leu Thr Val Leu Gly
                245                 250                 255

Gly Gly Gly Ser Glu Ser Lys Tyr Gly Pro Pro Cys Pro Pro Cys Pro
            260                 265                 270

Ala Pro Glu Phe Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300
```

```
Val Val Asp Val Ser Gln Glu Asp Pro Glu Val Gln Phe Asn Trp Tyr
305                 310                 315                 320

Val Asp Gly Val Glu Val His Asn Ala Lys Thr Lys Pro Arg Glu Glu
            325                 330                 335

Gln Phe Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Gly Leu Pro Ser Ser Ile Glu Lys Thr Ile Ser Lys Ala Lys Gly Gln
        370                 375                 380

Pro Arg Glu Pro Gln Val Tyr Thr Leu Pro Pro Ser Gln Glu Glu Met
385                 390                 395                 400

Thr Lys Asn Gln Val Ser Leu Thr Cys Leu Val Lys Gly Phe Tyr Pro
            405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Arg Leu Thr Val Asp Lys Ser Arg Trp Gln Glu Gly Asn Val
450                 455                 460

Phe Ser Cys Ser Val Met His Glu Ala Leu His Asn His Tyr Thr Gln
465                 470                 475                 480

Lys Ser Leu Ser Leu Ser Leu Gly Lys
                485

<210> SEQ ID NO 152
<211> LENGTH: 484
<212> TYPE: PRT
<213> ORGANISM: Artificial Sequence
<220> FEATURE:
<223> OTHER INFORMATION: C2-4A-Fc

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu His Met Asp Ser Leu Arg Ala Glu Asp Thr Ala Ile Tyr
            85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser Gly Gly Gly Gly
        115                 120                 125

Ser Gly Gly Gly Gly Ser Gly Gly Gly Ser Gln Ser Ala Leu Ile
    130                 135                 140

Gln Pro Pro Ser Ala Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
                165                 170                 175
```

Tyr Gln Gln His Pro Gly Lys Val Pro Lys Leu Met Ile Tyr Glu Val
                180                 185                 190

Ser Lys Arg Pro Ser Gly Val Pro Asp Arg Phe Ser Gly Ser Lys Ser
            195                 200                 205

Gly Asn Thr Ala Ser Leu Thr Ile Ser Gly Leu Gln Ala Glu Asp Glu
        210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Gly Leu Pro Ser Ser
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
        435                 440                 445

Val Asp Lys Ser Arg Trp Gln Glu Gly Asn Val Phe Ser Cys Ser Val
450                 455                 460

Met His Glu Ala Leu His Asn His Tyr Thr Gln Lys Ser Leu Ser Leu
                470                 475                 480

Ser Leu Gly Lys

<210> SEQ ID NO 153
<211> LENGTH: 484
<212> TYPE: PRT
<213> ORGANISM: Artificial Sequence
<220> FEATURE:
<223> OTHER INFORMATION: C2-4B-Fc

<400> SEQUENCE: 153

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Asp Tyr
            20                  25                  30

Tyr Met Asn Trp Phe Arg Gln Ala Pro Gly Lys Gly Leu Glu Trp Val
        35                  40                  45

```
Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Asn Asn Ser
65                  70                  75                  80

Leu Tyr Leu His Met Asp Ser Leu Arg Ala Glu Asp Thr Ala Ile Tyr
                85                  90                  95

Phe Cys Ala Arg Val Val Pro Ala Gly Ser Gly Trp Arg Trp Phe Asp
                100                 105                 110

Pro Trp Gly Gln Gly Thr Leu Val Thr Val Ser Ser Gly Gly Gly Gly
            115                 120                 125

Ser Gly Gly Gly Gly Ser Gly Gly Gly Gly Ser Gln Ser Val Leu Ile
130                 135                 140

Gln Pro Pro Ser Val Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
                165                 170                 175

Tyr Gln Gln His Pro Gly Lys Val Pro Lys Leu Met Ile Tyr Glu Val
                180                 185                 190

Ser Lys Arg Pro Ser Gly Val Pro Asp Arg Phe Ser Gly Ser Lys Ser
            195                 200                 205

Gly Asp Thr Ala Ser Leu Thr Ile Ser Gly Leu Gln Ala Glu Asp Glu
            210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Gly Ser Glu
                245                 250                 255

Ser Lys Tyr Gly Pro Pro Cys Pro Pro Cys Pro Ala Pro Glu Phe Leu
                260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
            290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335

Tyr Arg Val Val Ser Val Leu Thr Val Leu His Gln Asp Trp Leu Asn
                340                 345                 350

Gly Lys Glu Tyr Lys Cys Lys Val Ser Asn Lys Gly Leu Pro Ser Ser
            355                 360                 365

Ile Glu Lys Thr Ile Ser Lys Ala Lys Gly Gln Pro Arg Glu Pro Gln
            370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
                420                 425                 430

Pro Val Leu Asp Ser Asp Gly Ser Phe Phe Leu Tyr Ser Arg Leu Thr
            435                 440                 445

Val Asp Lys Ser Arg Trp Gln Glu Gly Asn Val Phe Ser Cys Ser Val
450                 455                 460

Met His Glu Ala Leu His Asn His Tyr Thr Gln Lys Ser Leu Ser Leu
```

<210> SEQ ID NO 154
<211> LENGTH: 484
<212> TYPE: PRT
<213> ORGANISM: Artificial Sequence
<220> FEATURE:
<223> OTHER INFORMATION: C2-4C-Fc

<400> SEQUENCE: 154

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser Gly Gly Gly Gly
        115                 120                 125

Ser Gly Gly Gly Gly Ser Gly Gly Gly Gly Ser Gln Ser Val Leu Ile
    130                 135                 140

Gln Pro Pro Ser Ala Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
                165                 170                 175

Tyr Gln Gln His Pro Gly Lys Val Pro Lys Leu Met Ile Tyr Glu Val
            180                 185                 190

Ser Lys Arg Pro Ser Gly Val Pro Asp Arg Phe Ser Gly Ser Lys Ser
        195                 200                 205

Gly Asn Thr Ala Ser Leu Thr Val Ser Gly Leu Gln Ala Glu Asp Glu
    210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335

Tyr Arg Val Val Ser Val Leu Thr Val Leu His Gln Asp Trp Leu Asn
            340                 345                 350
```

```
Gly Lys Glu Tyr Lys Cys Lys Val Ser Asn Lys Gly Leu Pro Ser Ser
            355                 360                 365

Ile Glu Lys Thr Ile Ser Lys Ala Lys Gly Gln Pro Arg Glu Pro Gln
    370                 375                 380

Val Tyr Thr Leu Pro Pro Ser Gln Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
                435                 440                 445

Val Asp Lys Ser Arg Trp Gln Glu Gly Asn Val Phe Ser Cys Ser Val
450                 455                 460

Met His Glu Ala Leu His Asn His Tyr Thr Gln Lys Ser Leu Ser Leu
465                 470                 475                 480

Ser Leu Gly Lys

<210> SEQ ID NO 155
<211> LENGTH: 484
<212> TYPE: PRT
<213> ORGANISM: Artificial Sequence
<220> FEATURE:
<223> OTHER INFORMATION: C2-5A-Fc

<400> SEQUENCE: 155

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu His Met Asp Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser Gly Gly Gly Gly
        115                 120                 125

Ser Gly Gly Gly Gly Ser Gly Gly Gly Gly Ser Gln Ser Val Leu Ile
    130                 135                 140

Gln Pro Pro Ser Val Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
                165                 170                 175

Tyr Gln Gln His Pro Gly Lys Val Pro Lys Leu Met Ile Tyr Glu Val
            180                 185                 190

Ser Lys Arg Pro Ser Gly Val Pro Asp Arg Phe Ser Gly Ser Lys Ser
        195                 200                 205

Gly Asn Thr Ala Ser Leu Thr Ile Ser Gly Leu Gln Ala Glu Asp Glu
    210                 215                 220
```

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Gly Ser Glu
            245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
            290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
            325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Gly Leu Pro Ser Ser
            355                 360                 365

Ile Glu Lys Thr Ile Ser Lys Ala Lys Gly Gln Pro Arg Glu Pro Gln
            370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
            405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
            435                 440                 445

Val Asp Lys Ser Arg Trp Gln Glu Gly Asn Val Phe Ser Cys Ser Val
            450                 455                 460

Met His Glu Ala Leu His Asn His Tyr Thr Gln Lys Ser Leu Ser Leu
465                 470                 475                 480

Ser Leu Gly Lys

<210> SEQ ID NO 156
<211> LENGTH: 484
<212> TYPE: PRT
<213> ORGANISM: Artificial Sequence
<220> FEATURE:
<223> OTHER INFORMATION: C2-5B-Fc

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
            35                  40                  45

Ser Tyr Ile Ser Ser Ser Ala Ser Gly Ser Thr Ile Tyr Tyr Ala Asp
            50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Ile Tyr
            85                  90                  95

Phe Cys Ala Arg Val Val Pro Ala Gly Ser Gly Trp Arg Trp Phe Asp

```
                100             105             110
Pro Trp Gly Gln Gly Thr Leu Val Thr Val Ser Ser Gly Gly Gly
            115             120             125

Ser Gly Gly Gly Gly Ser Gly Gly Gly Gly Ser Gln Ser Val Leu Ile
            130             135             140

Gln Pro Pro Ser Ala Ser Gly Ser Pro Gly Gln Ser Val Thr Ile Ser
145             150             155             160

Cys Thr Gly Ile Ser Ser Asp Val Gly Ala Tyr Asp Tyr Val Ser Trp
                165             170             175

Tyr Gln Gln His Pro Gly Lys Val Pro Lys Leu Met Ile Tyr Glu Val
                180             185             190

Ser Lys Arg Pro Ser Gly Val Pro Asp Arg Phe Ser Gly Ser Lys Ser
            195             200             205

Gly Asn Thr Ala Ser Leu Thr Ile Ser Gly Leu Gln Ala Glu Asp Glu
            210             215             220

Ala Asp Tyr Tyr Cys Ser Ser His Ala Gly Ser Asn Asn Phe Tyr Val
225             230             235             240

Phe Gly Thr Gly Thr Lys Leu Thr Val Leu Gly Gly Gly Ser Glu
                245             250             255

Ser Lys Tyr Gly Pro Pro Cys Pro Pro Cys Pro Ala Pro Glu Phe Leu
            260             265             270

Gly Gly Pro Ser Val Phe Leu Phe Pro Pro Lys Pro Lys Asp Thr Leu
            275             280             285

Met Ile Ser Arg Thr Pro Glu Val Thr Cys Val Val Val Asp Val Ser
290             295             300

Gln Glu Asp Pro Glu Val Gln Phe Asn Trp Tyr Val Asp Gly Val Glu
305             310             315             320

Val His Asn Ala Lys Thr Lys Pro Arg Glu Glu Gln Phe Asn Ser Thr
                325             330             335

Tyr Arg Val Val Ser Val Leu Thr Val Leu His Gln Asp Trp Leu Asn
                340             345             350

Gly Lys Glu Tyr Lys Cys Lys Val Ser Asn Lys Gly Leu Pro Ser Ser
            355             360             365

Ile Glu Lys Thr Ile Ser Lys Ala Lys Gly Gln Pro Arg Glu Pro Gln
            370             375             380

Val Tyr Thr Leu Pro Pro Ser Gln Glu Glu Met Thr Lys Asn Gln Val
385             390             395             400

Ser Leu Thr Cys Leu Val Lys Gly Phe Tyr Pro Ser Asp Ile Ala Val
                405             410             415

Glu Trp Glu Ser Asn Gly Gln Pro Glu Asn Asn Tyr Lys Thr Thr Pro
                420             425             430

Pro Val Leu Asp Ser Asp Gly Ser Phe Phe Leu Tyr Ser Arg Leu Thr
            435             440             445

Val Asp Lys Ser Arg Trp Gln Glu Gly Asn Val Phe Ser Cys Ser Val
            450             455             460

Met His Glu Ala Leu His Asn His Tyr Thr Gln Lys Ser Leu Ser Leu
465             470             475             480

Ser Leu Gly Lys

<210> SEQ ID NO 157
<211> LENGTH: 484
<212> TYPE: PRT
<213> ORGANISM: Artificial Sequence
<220> FEATURE:
```

<223> OTHER INFORMATION: C2-5C-Fc

<400> SEQUENCE: 157

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Asp Tyr
            20                  25                  30

Tyr Met Asn Trp Phe Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Asn Asn Ser
65                  70                  75                  80

Leu Tyr Leu His Met Asp Ser Leu Arg Ala Glu Asp Thr Ala Ile Tyr
                85                  90                  95

Tyr Cys Ala Arg Val Val Pro Ala Gly Ser Gly Trp Arg Trp Phe Asp
            100                 105                 110

Pro Trp Gly Gln Gly Thr Leu Val Thr Val Ser Ser Gly Gly Gly Gly
        115                 120                 125

Ser Gly Gly Gly Gly Ser Gly Gly Gly Gly Ser Gln Ser Val Leu Ile
130                 135                 140

Gln Pro Pro Ser Val Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
                165                 170                 175

Tyr Gln Gln His Pro Gly Lys Val Pro Lys Leu Met Ile Tyr Glu Val
            180                 185                 190

Ser Lys Arg Pro Ser Gly Val Pro Asp Arg Phe Ser Gly Ser Lys Ser
        195                 200                 205

Gly Asp Thr Ala Ser Leu Thr Ile Ser Gly Leu Gln Ala Glu Asp Glu
    210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Gly Leu Pro Ser Ser
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Gln Glu Glu Met Thr Lys Asn Gln Val
385                 390                 395                 400
```

```
Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
            435                 440                 445

Val Asp Lys Ser Arg Trp Gln Glu Gly Asn Val Phe Ser Cys Ser Val
450                 455                 460

Met His Glu Ala Leu His Asn His Tyr Thr Gln Lys Ser Leu Ser Leu
465                 470                 475                 480

Ser Leu Gly Lys

<210> SEQ ID NO 158
<211> LENGTH: 484
<212> TYPE: PRT
<213> ORGANISM: Artificial Sequence
<220> FEATURE:
<223> OTHER INFORMATION: C2-6A-Fc

<400> SEQUENCE: 158

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
            35                  40                  45

Ser Tyr Ile Ser Ser Ser Ala Ser Gly Ser Thr Ile Tyr Tyr Ala Asp
50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser Gly Gly Gly Gly
            115                 120                 125

Ser Gly Gly Gly Gly Ser Gly Gly Gly Ser Gln Ser Val Leu Ile
            130                 135                 140

Gln Pro Pro Ser Val Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
                165                 170                 175

Tyr Gln Gln His Pro Gly Lys Val Pro Lys Leu Met Ile Tyr Glu Val
            180                 185                 190

Ser Lys Arg Pro Ser Gly Val Pro Asp Arg Phe Ser Gly Ser Lys Ser
            195                 200                 205

Gly Asn Thr Ala Ser Leu Thr Ile Ser Gly Leu Gln Ala Glu Asp Glu
210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
```

-continued

```
                275                 280                 285
Met Ile Ser Arg Thr Pro Glu Val Thr Cys Val Val Val Asp Val Ser
290                 295                 300
Gln Glu Asp Pro Glu Val Gln Phe Asn Trp Tyr Val Asp Gly Val Glu
305                 310                 315                 320
Val His Asn Ala Lys Thr Lys Pro Arg Glu Glu Gln Phe Asn Ser Thr
                325                 330                 335
Tyr Arg Val Val Ser Val Leu Thr Val Leu His Gln Asp Trp Leu Asn
                340                 345                 350
Gly Lys Glu Tyr Lys Cys Lys Val Ser Asn Lys Gly Leu Pro Ser Ser
                355                 360                 365
Ile Glu Lys Thr Ile Ser Lys Ala Lys Gly Gln Pro Arg Glu Pro Gln
370                 375                 380
Val Tyr Thr Leu Pro Pro Ser Gln Glu Glu Met Thr Lys Asn Gln Val
385                 390                 395                 400
Ser Leu Thr Cys Leu Val Lys Gly Phe Tyr Pro Ser Asp Ile Ala Val
                405                 410                 415
Glu Trp Glu Ser Asn Gly Gln Pro Glu Asn Asn Tyr Lys Thr Thr Pro
                420                 425                 430
Pro Val Leu Asp Ser Asp Gly Ser Phe Phe Leu Tyr Ser Arg Leu Thr
                435                 440                 445
Val Asp Lys Ser Arg Trp Gln Glu Gly Asn Val Phe Ser Cys Ser Val
                450                 455                 460
Met His Glu Ala Leu His Asn His Tyr Thr Gln Lys Ser Leu Ser Leu
465                 470                 475                 480
Ser Leu Gly Lys

<210> SEQ ID NO 159
<211> LENGTH: 484
<212> TYPE: PRT
<213> ORGANISM: Artificial Sequence
<220> FEATURE:
<223> OTHER INFORMATION: C2-6B-Fc

<400> SEQUENCE: 159

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Val Ser Asp Tyr
                20                  25                  30
Tyr Met Asn Trp Ile Arg Gln Ala Pro Gly Lys Gly Leu Glu Trp Val
                35                  40                  45
Ser Tyr Ile Ser Ser Ser Ala Ser Gly Ser Thr Ile Tyr Tyr Ala Asp
                50                  55                  60
Ser Val Lys Gly Arg Phe Thr Ile Ser Arg Asp Asn Ala Lys Asn Ser
65                  70                  75                  80
Leu Tyr Leu Gln Met Asn Ser Leu Arg Ala Glu Asp Thr Ala Ile Tyr
                85                  90                  95
Phe Cys Ala Arg Val Val Pro Ala Gly Ser Gly Trp Arg Trp Phe Asp
                100                 105                 110
Pro Trp Gly Gln Gly Thr Leu Val Thr Val Ser Ser Gly Gly Gly Gly
                115                 120                 125
Ser Gly Gly Gly Gly Ser Gly Gly Gly Ser Gln Ser Val Leu Ile
                130                 135                 140
Gln Pro Pro Ser Val Ser Gly Ser Pro Gly Gln Ser Val Thr Ile Ser
145                 150                 155                 160
```

```
Cys Thr Gly Ile Ser Ser Asp Val Gly Ala Tyr Asp Tyr Val Ser Trp
                165                 170                 175

Tyr Gln Gln His Pro Gly Lys Val Pro Lys Leu Met Ile Tyr Glu Val
            180                 185                 190

Ser Lys Arg Pro Ser Gly Val Pro Asp Arg Phe Ser Gly Ser Lys Ser
        195                 200                 205

Gly Asn Thr Ala Ser Leu Thr Val Ser Gly Leu Gln Ala Glu Asp Glu
    210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Gly Leu Pro Ser Ser
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
        435                 440                 445

Val Asp Lys Ser Arg Trp Gln Glu Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Leu Gly Lys

<210> SEQ ID NO 160
<211> LENGTH: 484
<212> TYPE: PRT
<213> ORGANISM: Artificial Sequence
<220> FEATURE:
<223> OTHER INFORMATION: C2-7A-Fc

<400> SEQUENCE: 160

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser Asp Tyr
            20                  25                  30
```

```
Tyr Met Asn Trp Ile Arg Gln Ala Pro Gly Lys Gly Leu Glu Trp Val
         35                  40                  45

Ser Tyr Ile Ser Ser Ser Ala Ser Gly Ser Thr Ile Tyr Tyr Ala Asp
 50                  55                  60

Ser Val Lys Gly Arg Phe Thr Ile Ser Arg Asp Asn Ala Lys Asn Ser
 65                  70                  75                  80

Leu Tyr Leu His Met Asp Ser Leu Arg Ala Glu Asp Thr Ala Ile Tyr
                 85                  90                  95

Phe Cys Ala Arg Val Val Pro Ala Gly Ser Gly Trp Arg Trp Phe Asp
             100                 105                 110

Pro Trp Gly Gln Gly Thr Leu Val Thr Val Ser Ser Gly Gly Gly Gly
             115                 120                 125

Ser Gly Gly Gly Gly Ser Gly Gly Gly Ser Gln Ser Ala Leu Ile
         130                 135                 140

Gln Pro Pro Ser Val Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
                 165                 170                 175

Tyr Gln Gln His Pro Gly Thr Val Pro Lys Leu Met Ile Tyr Glu Val
             180                 185                 190

Ser Lys Arg Pro Ser Gly Val Pro Asp Arg Phe Ser Gly Ser Lys Ser
         195                 200                 205

Gly Asn Thr Ala Ser Leu Thr Ile Ser Gly Leu Gln Ala Glu Asp Glu
         210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Gly Ser Glu
                 245                 250                 255

Ser Lys Tyr Gly Pro Pro Cys Pro Pro Cys Pro Ala Pro Glu Phe Leu
             260                 265                 270

Gly Gly Pro Ser Val Phe Leu Phe Pro Pro Lys Pro Lys Asp Thr Leu
             275                 280                 285

Met Ile Ser Arg Thr Pro Glu Val Thr Cys Val Val Val Asp Val Ser
         290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                 325                 330                 335

Tyr Arg Val Val Ser Val Leu Thr Val Leu His Gln Asp Trp Leu Asn
                 340                 345                 350

Gly Lys Glu Tyr Lys Cys Lys Val Ser Asn Lys Gly Leu Pro Ser Ser
             355                 360                 365

Ile Glu Lys Thr Ile Ser Lys Ala Lys Gly Gln Pro Arg Glu Pro Gln
             370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                 405                 410                 415

Glu Trp Glu Ser Asn Gly Gln Pro Glu Asn Asn Tyr Lys Thr Thr Pro
             420                 425                 430

Pro Val Leu Asp Ser Asp Gly Ser Phe Phe Leu Tyr Ser Arg Leu Thr
             435                 440                 445

Val Asp Lys Ser Arg Trp Gln Glu Gly Asn Val Phe Ser Cys Ser Val
```

```
                    450                 455                 460
Met His Glu Ala Leu His Asn His Tyr Thr Gln Lys Ser Leu Ser Leu
465                 470                 475                 480

Ser Leu Gly Lys

<210> SEQ ID NO 161
<211> LENGTH: 484
<212> TYPE: PRT
<213> ORGANISM: Artificial Sequence
<220> FEATURE:
<223> OTHER INFORMATION: C2-7B-Fc

<400> SEQUENCE: 161

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Asn Asn Ser
65                  70                  75                  80

Leu Tyr Leu Gln Met Asn Ser Leu Arg Thr Glu Asp Thr Ala Ile Tyr
                85                  90                  95

Tyr Cys Ala Arg Val Val Pro Ala Gly Ser Gly Trp Arg Trp Phe Asp
            100                 105                 110

Pro Trp Gly Gln Gly Thr Leu Val Thr Val Ser Ser Gly Gly Gly Gly
        115                 120                 125

Ser Gly Gly Gly Gly Ser Gly Gly Gly Ser Gln Ser Val Leu Ile
    130                 135                 140

Gln Pro Pro Ser Val Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
                165                 170                 175

Tyr Gln Gln His Pro Gly Lys Val Pro Lys Leu Met Ile Tyr Glu Val
            180                 185                 190

Ser Lys Arg Pro Ser Gly Val Pro Asp Arg Phe Ser Gly Ser Lys Ser
        195                 200                 205

Gly Asp Thr Ala Ser Leu Thr Ile Ser Gly Leu Gln Ala Glu Asp Glu
    210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335
```

```
Tyr Arg Val Val Ser Val Leu Thr Val Leu His Gln Asp Trp Leu Asn
            340                 345                 350

Gly Lys Glu Tyr Lys Cys Lys Val Ser Asn Lys Gly Leu Pro Ser Ser
            355                 360                 365

Ile Glu Lys Thr Ile Ser Lys Ala Lys Gly Gln Pro Arg Glu Pro Gln
370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
            405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
            435                 440                 445

Val Asp Lys Ser Arg Trp Gln Glu Gly Asn Val Phe Ser Cys Ser Val
            450                 455                 460

Met His Glu Ala Leu His Asn His Tyr Thr Gln Lys Ser Leu Ser Leu
465                 470                 475                 480

Ser Leu Gly Lys

<210> SEQ ID NO 162
<211> LENGTH: 484
<212> TYPE: PRT
<213> ORGANISM: Artificial Sequence
<220> FEATURE:
<223> OTHER INFORMATION: C2-7BN78K-Fc

<400> SEQUENCE: 162

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
            35                  40                  45

Ser Tyr Ile Ser Ser Ser Ala Ser Gly Ser Thr Ile Tyr Tyr Ala Asp
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Thr Glu Asp Thr Ala Ile Tyr
            85                  90                  95

Tyr Cys Ala Arg Val Val Pro Ala Gly Ser Gly Trp Arg Trp Phe Asp
            100                 105                 110

Pro Trp Gly Gln Gly Thr Leu Val Thr Val Ser Ser Gly Gly Gly Gly
            115                 120                 125

Ser Gly Gly Gly Gly Ser Gly Gly Gly Ser Gln Ser Val Leu Ile
        130                 135                 140

Gln Pro Pro Ser Val Ser Gly Ser Pro Gly Gln Ser Val Thr Ile Ser
145                 150                 155                 160

Cys Thr Gly Ile Ser Ser Asp Val Gly Ala Tyr Asp Tyr Val Ser Trp
            165                 170                 175

Tyr Gln Gln His Pro Gly Lys Val Pro Lys Leu Met Ile Tyr Glu Val
            180                 185                 190

Ser Lys Arg Pro Ser Gly Val Pro Asp Arg Phe Ser Gly Ser Lys Ser
            195                 200                 205
```

```
Gly Asp Thr Ala Ser Leu Thr Ile Ser Gly Leu Gln Ala Glu Asp Glu
    210                 215                 220

Ala Asp Tyr Tyr Cys Ser Ser His Ala Gly Ser Asn Asn Phe Tyr Val
225                 230                 235                 240

Phe Gly Thr Gly Thr Lys Leu Thr Val Leu Gly Gly Gly Gly Ser Glu
                245                 250                 255

Ser Lys Tyr Gly Pro Pro Cys Pro Pro Cys Pro Ala Pro Glu Phe Leu
                260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Gly Leu Pro Ser Ser
        355                 360                 365

Ile Glu Lys Thr Ile Ser Lys Ala Lys Gly Gln Pro Arg Glu Pro Gln
370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
        435                 440                 445

Val Asp Lys Ser Arg Trp Gln Glu Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Leu Gly Lys

<210> SEQ ID NO 163
<211> LENGTH: 229
<212> TYPE: PRT
<213> ORGANISM: Artificial Sequence
<220> FEATURE:
<223> OTHER INFORMATION: Fc

<400> SEQUENCE: 163

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
```

```
            85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
            115                 120                 125
Gln Val Tyr Thr Leu Pro Pro Ser Gln Glu Glu Met Thr Lys Asn Gln
            130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                    165                 170                 175
Pro Pro Val Leu Asp Ser Asp Gly Ser Phe Phe Leu Tyr Ser Arg Leu
                    180                 185                 190
Thr Val Asp Lys Ser Arg Trp Gln Glu Gly Asn Val Phe Ser Cys Ser
                    195                 200                 205
Val Met His Glu Ala Leu His Asn His Tyr Thr Gln Lys Ser Leu Ser
                    210                 215                 220
Leu Ser Leu Gly Lys
225

<210> SEQ ID NO 164
<211> LENGTH: 229
<212> TYPE: PRT
<213> ORGANISM: Artificial Sequence
<220> FEATURE:
<223> OTHER INFORMATION: Fc-WT

<400> SEQUENCE: 164

Glu Ser Lys Tyr Gly Pro Pro Cys Pro Ser Cys Pro Ala Pro Glu Phe
1               5                   10                  15
Leu Gly Gly Pro Ser Val Phe Leu Phe Pro Pro Lys Pro Lys Asp Thr
                    20                  25                  30
Leu Met Ile Ser Arg Thr Pro Glu Val Thr Cys Val Val Val Asp Val
            35                  40                  45
Ser Gln Glu Asp Pro Glu Val Gln Phe Asn Trp Tyr Val Asp Gly Val
50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
            115                 120                 125
Gln Val Tyr Thr Leu Pro Pro Ser Gln Glu Glu Met Thr Lys Asn Gln
            130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                    165                 170                 175
Pro Pro Val Leu Asp Ser Asp Gly Ser Phe Phe Leu Tyr Ser Arg Leu
                    180                 185                 190
Thr Val Asp Lys Ser Arg Trp Gln Glu Gly Asn Val Phe Ser Cys Ser
                    195                 200                 205
Val Met His Glu Ala Leu His Asn His Tyr Thr Gln Lys Ser Leu Ser
```

Leu Ser Leu Gly Lys
225

<210> SEQ ID NO 165
<211> LENGTH: 15
<212> TYPE: PRT
<213> ORGANISM: Artificial Sequence
<220> FEATURE:
<223> OTHER INFORMATION: (G4S)3

<400> SEQUENCE: 165

Gly Gly Gly Gly Ser Gly Gly Gly Gly Ser Gly Gly Gly Gly Ser
1               5                   10                  15

<210> SEQ ID NO 166
<211> LENGTH: 5
<212> TYPE: PRT
<213> ORGANISM: Artificial Sequence
<220> FEATURE:
<223> OTHER INFORMATION: G4S

<400> SEQUENCE: 166

Gly Gly Gly Gly Ser
1               5

<210> SEQ ID NO 167
<211> LENGTH: 1452
<212> TYPE: DNA
<213> ORGANISM: Artificial Sequence
<220> FEATURE:
<223> OTHER INFORMATION: C2-7BN78K-Fc Nucleotide

<400> SEQUENCE: 167

| | | | | | |
|---|---|---|---|---|---|
| gaggtgcagc | tggtggaaag | cggcggcgga | ctggtgaagc | tggaggttc | tctgaggctg | 60 |
| agctgtgccg | cctccggctt | caccgtgagc | gactactaca | tgaactggat | caggcaggcc | 120 |
| cccggcaaag | gactggagtg | ggtgagctac | atctcctcct | ccgcctccgg | cagcaccatc | 180 |
| tactacgccg | actccgtgaa | gggcaggttc | accatctcca | gggataacgc | caagaacagc | 240 |
| ctgtacctgc | agatgaactc | cctgaggacc | gaggacaccg | ccatctacta | ctgtgccagg | 300 |
| gtggtgcccg | ctggaagcgg | atggaggtgg | ttcgaccct | ggggccaggg | aacactggtg | 360 |
| accgtgagca | gcggaggagg | aggaagcgga | ggaggaggaa | gcggaggagg | cggcagccag | 420 |
| agcgtgctga | ttcagcctcc | cagcgtgagc | ggaagccctg | gacagagcgt | gaccatcagc | 480 |
| tgcaccggca | tcagctccga | tgtgggcgcc | tacgactacg | tgagctggta | tcaacagcac | 540 |
| cctggcaagg | tgcccaagct | gatgatctac | gaggtgtcca | aaggcccag | cggcgtgccc | 600 |
| gataggttta | gcggctccaa | gtccggcgac | acagcctccc | tgaccatcag | cggcctccag | 660 |
| gctgaggatg | aggccgacta | ctactgcagc | agccatgccg | gcagcaacaa | cttttacgtg | 720 |
| ttcggcaccg | gcacaaagct | gaccgtgctg | ggcggaggcg | gcagcgagtc | caaatatggt | 780 |
| cccccatgcc | caccatgccc | agctccggag | ttcctggggg | gaccatcagt | cttcctgttc | 840 |
| ccccaaaac | ccaaggacac | tctcatgatc | tcccggaccc | ctgaggtcac | gtgcgtggtg | 900 |
| gtggacgtga | gccaggaaga | ccccgaggtc | cagttcaact | ggtacgtgga | tggcgtggag | 960 |
| gtgcataatg | ccaagacaaa | gccgcgggag | gagcagttca | acagcacgta | ccgtgtggtc | 1020 |
| agcgtcctca | ccgtcctgca | ccaggactgg | ctgaacggca | aggagtacaa | gtgcaaggtc | 1080 |
| tccaacaaag | gcctcccgtc | ctccatcgag | aaaaccatct | ccaaagccaa | agggcagccc | 1140 |

-continued

```
cgagagccac aggtgtacac cctgccccca tcccaggagg agatgaccaa gaaccaggtc    1200
agcctgacct gcctggtcaa aggcttctac cccagcgaca tcgccgtgga gtgggagagc    1260
aatgggcagc cggagaacaa ctacaagacc acgcctccg  tgctggactc cgacggctcc    1320
ttcttcctct acagcaggct aaccgtggac aagagcaggt ggcaggaggg gaatgtcttc    1380
tcatgctccg tgatgcatga ggctctgcac aaccactaca cacagaagag cctctccctg    1440
tctctgggta aa                                                        1452
```